(12) United States Patent
Altaba et al.

(10) Patent No.: US 7,741,298 B2
(45) Date of Patent: *Jun. 22, 2010

(54) METHOD AND COMPOSITIONS FOR INHIBITING TUMORIGENESIS

(75) Inventors: Ariel Ruiz i Altaba, New York, NY (US); Pilar Sanchez, Valencia (ES); William Rom, Rye, NY (US); Kam-Meng Tchou Wong, New York, NY (US)

(73) Assignee: New York University, New York, NY (US)

( * ) Notice: Subject to any disclaimer, the term of this patent is extended or adjusted under 35 U.S.C. 154(b) by 183 days.

This patent is subject to a terminal disclaimer.

(21) Appl. No.: 10/930,723

(22) Filed: Aug. 31, 2004

(65) Prior Publication Data

US 2005/0112707 A1 May 26, 2005

Related U.S. Application Data

(63) Continuation-in-part of application No. 10/456,954, filed on Jun. 6, 2003, now abandoned, which is a continuation-in-part of application No. 09/825,155, filed on Apr. 3, 2001, now abandoned, which is a continuation of application No. 09/102,491, filed on Jun. 22, 1998, now Pat. No. 6,238,876, said application No. 10/456,954 is a continuation-in-part of application No. 10/414,267, filed on Apr. 15, 2003, now abandoned, and a continuation-in-part of application No. 10/927,951, filed on Aug. 29, 2004, now abandoned, which is a continuation-in-part of application No. 10/456,954, filed on Jun. 6, 2003, now abandoned.

(60) Provisional application No. 60/050,286, filed on Jun. 20, 1997, provisional application No. 60/372,508, filed on Apr. 15, 2002.

(51) Int. Cl.
  *A01N 43/04* (2006.01)
  *A61K 31/70* (2006.01)
(52) U.S. Cl. .................................................... 514/44
(58) Field of Classification Search .................... 514/44
  See application file for complete search history.

(56) References Cited

U.S. PATENT DOCUMENTS 6,329,203 B1 * 12/2001 Bennett et al. ............... 435/377

FOREIGN PATENT DOCUMENTS

WO   WO 2004/020599   * 11/2004

OTHER PUBLICATIONS

Pai et al., Gene Therapy 2006; 464-477.*
Ryther et al., Gene Therapy 2005; 12: 5-11.*
Schiffelers et al., Nucleic Acids Research 2004; 32: e49.*
Wetmore, Curr Opin Genetics Dev, 2003, 13:34-42.*
Agrawal et al, Micro Mol Biol Rev, 2003, 67:657-685.*
MSN encarta on-line dictionary, "metastasis", Feb. 26, 2008.*
Hammond et al. (Nature, 2001, vol. 2, pp. 110-119).*
Ambion (Oct. 2002) TechNotes 9(5) Selecting siRNA Sequences to Incorporate into the pSilencer Vectors. [online], [retrieved on Nov. 5, 2008] using Internet /www.ambion.com>.*
Ackerman et al., *Neoplasm with follicular differentiation*. Philadelphia: Lea and Febiger. Philadelphia: Lea and Febiger (1993).
Alexandre et al., *Genes and Dev.* 10, 2003-2013 (1996).
Belloni et al., *Nature Genetics* 14, 353-356 (1996).
Blessing et al., *Genes Dev.* 7, 204-215 (1993).
Bitgood et al., *Dev. Biol.* 172, 126-138 (1995).
Byrne et al., *Development* 120, 2369-2383 (1994).
Cerroni et al., *J Cutan Pathol* 21, 398-403 (1994).
Chen et al., *Cell* 87, 553-563 (1996).
Chiang et al., *Nature* 383, 407-413 (1996).
Concordet et al., *Development* 122, 2835-2846 (1996).
Cotsarelis et al., *Cell* 61, 1329-1337 (1990).
Dahmane, et al., *Development & Disease*, 128, 5201-5212 (2001).
Domínguez et al., *Science* 272, 1621-1625 (1996).
Echelard et al., *Cell* 75, 1417-1430 (1993).
Ekker, et al., *Development* 121, 2337-2347 (1995).
Elder, D. Ed. in chief. *Lever's Histopatology of the Skin*. 8th Edition. Philadelphia, Lippincott-Raven (1997).
Epstein et al.,*Development* 122, 2885-2894 (1996).
Ericson et al., *Cell* 87, 661-673 (1996).
Forbes et al., *Development Supplement* 115-124 (1993).
Fuller et al., *Mutation Research* 276, 299-306 (1992).
Gailani et al., *Nature Genet.* 14, 78-81 (1996).
Goodrich et al., *Genes Dev.* 10,301-312 (1996).
Grimwood et al., *Society for Invest. Derm.* 86, 191-194 (1986).
Hahn et al., *Cell* 85, 841-851 (1996).
Hammerschmidt et al., *Genes and Dev.* 10, 647-658 (1996).
Hepker et al., *Development* 124, 549-558 (1997).
Hynes et al., *Neuron* 15, 35-45 (1995).
Iseki et al., *Biochem. Biophys. Res. Commun.* 218, 688-693 (1996).
Johnson et al., *Science* 272, 1668-1671 (1996).
Kelsey-Motzny et al., *Mechanisms of Development* 52, 137-150 (1995).

(Continued)

*Primary Examiner*—Brian Whiteman
(74) *Attorney, Agent, or Firm*—Klauber & Jackson, LLC

(57) ABSTRACT

The present invention relates to compounds, small interfering RNAs and compositions and methods of inhibiting tumorigenesis using agents that inhibit the sonic hedgehog and GLI signaling pathway, including agents that inhibit GLI expression, synthesis and/or function. The present invention also relates to particular biomarkers that can be used in the diagnosis and prognosis of cancer. Methods of treating cancer, including glioblastomas, medulloblastomas, basal cell carcinomas, prostate cancer and small cell and non-small cell lung cancer are also provided using small organic compounds, siRNAs and blocking antibodies that inhibit or block the SHH/GLI pathway.

4 Claims, 19 Drawing Sheets

OTHER PUBLICATIONS

Kinzler et al., *Mol. Cell Biol.* 10, 634-642 (1990).
Kinzler et al., *Science* 236, 70-73 (1987).
Krauss et al., *.Cell* 75, 1431-1444 (1993).
Lai et al., *Development* 121, 2349-2360 (1995).
Lee, Jeffrey et al., *Development* vol. 124: pp. 2537-2552 (1997).
Liem et al, . *Cell* 82, 969-979 (1995).
Marigo et al., *Dev. Biol.* 180, 273-283 (1996).
Marigo et al., *Proc. Natl. Acad. Sci. USA* 93, 9346-9351 (1996).
Martí et al.*Nature* 375, 322-325 (1995).
Mullor et al *Development* 124, 1227-1237 (1997).
Nohno et al., *Biophys Res Comm.* 206, 33-39 (1995).
Oro, et al., *Science* 276:817-21 (1997).
Palma, et al., *Development*, 131, 337-345 (2004).
Platt, et al., *Mech. Dev.* 62, 121-135 in press (1997).
Roberts, et al., *Cancer Research* 49, 5407-5413 (1989).
Roelink et al., *Cell* 76, 761-775 (1994).
Roessler et al., *Nature Genntics* 14, 357-360 (1996).
Riddle, et al.*Cell* 75, 1401-1416 (1993).
Ruppert, et al., *Molecular and Cellular Biology* 11, 1724-1728 (1991).
Ruppert, et al., *Mol. Cell Biol.* 10, 5408-5415 (1990).
Ruiz i Altaba, A., et al. *Molecular and Cellular Neuroscience* 6, 106-121 (1995).
Ruiz i Altaba, A., et al., *Nat Rev Cancer*, 2, 361-372 (2002).
Ruiz i Altaba, A., et al., *Cancer Letters*, 204, 145-157 (2004).
Ruiz i Altaba, et al.,*Natl. Acad. Sci. USA* 90, 8268-8272 (1993).
Ruiz i Altaba, et al., *Mech. Dev.* 44, 91-108 (1993).
Ruiz i Altaba, A. *In Essential Developmental Biology- A Practical Approach.* (C. Stern and P.W.H. Holland) IRL Press, Oxford (1993).
Salgaller, et al., *Cancer Letters* 57, 243-253 (1991).
Sanchez, P., et al., *Mech. Dev.* 122, 223-230 (2005).
Sanchez, P., et al., *Cancer Res.*, 65, 2990-2992 (2005).
Sanchez, et al., *PNAS*, 101, 12561-12566 (2004).
Schaeren-Wiemers, et al., *Histochemistry* 100, 431-440 (1993).
Stecca, B., et al., *J. Neurobiol.* 64, 476-490 (2005).
Stecca, B., et al., *Trends Mol Med.*, 11, 199-203 (2005).
Shimizu et al., *J. Dermatol* 14, 359-363 (1987).
St-Jacques, et al., 1998, Curr Biol, 8, 1058-68.
Stone, et al., *Nature* 384, 129-134 (1996).
Urano, et al., *Society for Invest. Derm.* 104, 928-932 (1995).
van der Schroeff, et al., *Society for Invest Derm* 94, 423-425 (1990).
von Ohnen, et al., *Proc. Natl. Acad. Sci. USA.* 94, 2404-2409 (1997).
Wallace, et al., *Arch. Pathol* 50, 199-208 (1950).
Walterhouse, et al., *Developental Dyn.* 196, 91-102 (1993).
Wilson, et al., *Nature* 376, 331-333 (1995).
Xiao et al., *Pediatr Neurosurg* 20, 178-182 (1994).

\* cited by examiner

U87 cell number

U87 cell death

BrdU U87

Clonal Assay (BT18)

Clonal Assay (BT22)

10T 1/2 (AlkPh in response to Shh)

A

SEQUENCE LISTING

```
<160> NUMBER OF SEQ ID NOS: 33

<210> SEQ ID NO 1
<211> LENGTH: 1575
<212> TYPE: DNA
<213> ORGANISM: Homo sapiens

<400> SEQUENCE: 1
gcgaggcagc cagcgaggga gagagcgagc gggcgagccg gagcgaggaa gggaaagcgc        60
```

-continued

| | |
|---|---|
| aagagagagc gcacacgcac acacccgccg cgcgcactcg cgcacggacc cgcacgggga | 120 |
| cagctcggaa gtcatcagtt ccatgggcga gatgctgctg ctggcgagat gtctgctgct | 180 |
| agtcctcgtc tcctcgctgc tggtatgctc gggactggcg tgcggaccgg cagggggtt | 240 |
| cgggaagagg aggcacccca aaaagctgac ccctttagcc tacaagcagt ttatcccaa | 300 |
| tgtggccgag aagaccctag cgccagcgg aaggtatgaa gggaagatct ccagaaactc | 360 |
| cgagcgattt aaggaactca ccccaatta caaccccgac atcatattta aggatgaaga | 420 |
| aaacaccgga gcggacaggc tgatgactca gaggtgtaag gacaagttga acgctttggc | 480 |
| catctcggtg atgaaccagt ggccaggagt gaaactgcgg gtgaccgagg ctgggacga | 540 |
| agatggccac cactcagagg agtctctgca ctacgagggc cgcgcagtgg acatcaccac | 600 |
| gtctgaccgc gaccgcagca agtacggcat gctggcccgc ctggcggtgg aggccggctt | 660 |
| cgactgggtg tactacgagt ccaaggcaca tatccactgc tcggtgaaag cagagaactc | 720 |
| ggtggcggcc aaatcgggag gctgcttccc gggctcggcc acgtgcacc tggagcaggg | 780 |
| cggcaccaag ctggtgaagg acctgagccc cggggaccgc gtgctggcgg cggacgacca | 840 |
| gggccggctg ctctacagcg acttcctcac tttcctggac cgcgacgacg cgccaagaa | 900 |
| ggtcttctac gtgatcgaga cgcgggagcc gcgcgagcgc ctgctgctca ccgccgcgca | 960 |
| cctgctcttt gtggcgccgc acaacgactc ggccaccggg gagcccgagg cgtcctcggg | 1020 |
| ctcggggccg ccttccgggg gcgcactggg gcctcgggcg ctgttcgcca gccgcgtgcg | 1080 |
| cccgggccag cgcgtgtacg tggtggccga gcgtgacggg gaccgccggc tcctgcccgc | 1140 |
| cgctgtgcac agcgtgaccc taagcgagga ggccgcgggc gcctacgcgc cgctcacggc | 1200 |
| ccagggcacc attctcatca accgggtgct ggcctcgtgc tacgcggtca tcgaggagca | 1260 |
| cagctgggcg caccgggcct cgcgcccctt ccgcctggcg cacgcgctcc tggctgcact | 1320 |
| ggcgcccgcg cgcacggacc gcggcgggga cagcggcggc ggggaccgcg ggggcggcgg | 1380 |
| cggcagagta gccctaaccg ctccaggtgc tgccgacgct ccgggtgcgg ggccaccgc | 1440 |
| gggcatccac tggtactcgc agctgctcta ccaaataggc acctggctcc tggacagcga | 1500 |
| ggccctgcac ccgctgggca tggcggtcaa gtccagctga agccgggggg ccggggagg | 1560 |
| ggcgcgggag ggggc | 1575 |

<210> SEQ ID NO 2
<211> LENGTH: 462
<212> TYPE: PRT
<213> ORGANISM: Homo sapiens

<400> SEQUENCE: 2

Met Leu Leu Leu Ala Arg Cys Leu Leu Leu Val Leu Val Ser Ser Leu
1               5                   10                  15

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser 100                 105                 110
Val Met Asn Gln Trp Pro Gly Val Lys Leu Arg Val Thr Glu Gly Trp
            115                 120                 125

Asp Glu Asp Gly His His Ser Glu Ser Leu His Tyr Glu Gly Arg
        130                 135                 140

Ala Val Asp Ile Thr Thr Ser Asp Arg Asp Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
        275                 280                 285

Ser Gly Ser Gly Pro Pro Ser Gly Gly Ala Leu Gly Pro Arg Ala Leu
    290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365

Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Arg Val Ala Leu Thr
                405                 410                 415

Ala Pro Gly Ala Ala Asp Ala Pro Gly Ala Gly Thr Ala Gly Ile
        420                 425                 430

His Trp Tyr Ser Gln Leu Leu Tyr Gln Ile Gly Thr Trp Leu Leu Asp
    435                 440                 445

Ser Glu Ala Leu His Pro Leu Gly Met Ala Val Lys Ser Ser
    450                 455                 460

<210> SEQ ID NO 3
<211> LENGTH: 1314
<212> TYPE: DNA
<213> ORGANISM: Mus musculus

<400> SEQUENCE: 3
atgctgctgc tgctggccag atgttttctg gtgatccttg cttcctcgct gctggtgtgc     60
cccgggctgg cctgtgggcc cggcaggggg tttggaaaga ggcggcaccc caaaaagctg    120

```
accccttag cctacaagca gtttattccc aacgtagccg agaagaccct aggggccagc      180
ggcagatatg aagggaagat cacaagaaac tccgaacgat ttaaggaact caccccaat      240 tacaaccccg acatcatatt taaggatgag gaaaacacgg gagcagaccg gctgatgact      300
cagaggtgca agacaagtt aaatgccttg gccatctctg tgatgaacca gtggcctgga      360
gtgaagctgc gagtgaccga gggctgggat gaggacggcc atcattcaga ggagtctcta      420
cactatgagg gtcgagcagt ggacatcacc acgtccgacc gggaccgcag caagtacggc      480
atgctggctc gcctggctgt ggaagcaggt ttcgactggg tctactatga atccaaagct      540
cacatccact gttctgtgaa agcagagaac tccgtggcgg ccaaatccgg cggctgtttc      600
ccgggatccg ccaccgtgca cctggagcag ggcggcacca gctggtgaa ggacttacgt       660 cccggagacc gcgtgctggc ggctgacgac cagggccggc tgctgtacag cgacttcctc      720
accttcctgg accgcgacga aggcgccaag aaggtcttct acgtgatcga gacgctggag      780
ccgcgcgagc gcctgctgct caccgccgcg cacctgctct cgtggcgcc gcacaacgac       840 tcggggccca cgcccgggcc aagcgcgctc tttgccagcc gcgtgcgccc cgggcagcgc      900
gtgtacgtgg tggctgaacg cggcggggac cgccggctgc tgcccgccgc ggtgcacagc      960
gtgacgctgc gagaggagga ggcgggcgcg tacgcgccgc tcacggcgca cggcaccatt     1020
ctcatcaacc gggtgctcgc ctcgtgctac gctgtcatcg aggagcacag ctgggcacac     1080
cgggccttcg cgcctttccg cctggcgcac gcgctgctgg ccgcgctggc acccgcccgc     1140
acggacggcg ggggcggggg cagcatccct gcagcgcaat ctgcaacgga agcgaggggc     1200
gcggagccga ctgcgggcat ccactggtac tcgcagctgc tctaccacat tggcacctgg     1260
ctgttggaca gcagagaccat gcatcccttg ggaatggcgg tcaagtccag ctga            1314
```

<210> SEQ ID NO 4
<211> LENGTH: 429
<212> TYPE: PRT
<213> ORGANISM: Mus musculus

<400> SEQUENCE: 4

```
Phe Leu Val Ile Leu Ala Ser Ser Leu Leu Val Cys Pro Gly Leu Ala
 1               5                  10                  15

Cys Gly Pro Gly Arg Gly Phe Gly Lys Arg His Pro Lys Lys Leu
            20                  25                  30

Thr Pro Leu Ala Tyr Lys Gln Phe Ile Pro Asn Val Ala Glu Lys Thr
        35                  40                  45

Leu Gly Ala Ser Gly Arg Tyr Glu Gly Lys Ile Thr Arg Asn Ser Glu
    50                  55                  60

Arg Phe Lys Glu Leu Thr Pro Asn Tyr Asn Pro Asp Ile Ile Phe Lys
65                  70                  75                  80

Asp Glu Glu Asn Thr Gly Ala Asp Arg Leu Met Thr Gln Arg Cys Lys
                85                  90                  95

Asp Lys Leu Asn Ala Leu Ala Ile Ser Val Met Asn Gln Trp Pro Gly
            100                 105                 110

Val Lys Leu Arg Val Thr Glu Gly Trp Asp Glu Asp Gly His His Ser
        115                 120                 125

Glu Glu Ser Leu His Tyr Glu Gly Arg Ala Val Asp Ile Thr Thr Ser
    130                 135                 140

Asp Arg Asp Arg Ser Lys Tyr Gly Met Leu Ala Arg Leu Ala Val Glu
145                 150                 155                 160
```

-continued

```
Ala Gly Phe Asp Trp Val Tyr Tyr Glu Ser Lys Ala His Ile His Cys
            165                 170                 175
Ser Val Lys Ala Glu Asn Ser Val Ala Ala Lys Ser Gly Gly Cys Phe
        180                 185                 190
Pro Gly Ser Ala Thr Val His Leu Glu Gln Gly Gly Thr Lys Leu Val
    195                 200                 205
Lys Asp Leu Arg Pro Gly Asp Arg Val Leu Ala Ala Asp Asp Gln Gly
210                 215                 220
Arg Leu Leu Tyr Ser Asp Phe Leu Thr Phe Leu Asp Arg Asp Glu Gly
225                 230                 235                 240
Ala Lys Lys Val Phe Tyr Val Ile Glu Thr Leu Glu Pro Arg Glu Arg
                245                 250                 255
Leu Leu Leu Thr Ala Ala His Leu Leu Phe Val Ala Pro His Asn Asp
            260                 265                 270
Ser Gly Pro Thr Pro Gly Pro Ser Ala Leu Phe Ala Ser Arg Val Arg
        275                 280                 285
Pro Gly Gln Arg Val Tyr Val Ala Glu Arg Gly Gly Asp Arg Arg
    290                 295                 300
Leu Leu Pro Ala Ala Val His Ser Val Thr Leu Arg Glu Glu Ala
305                 310                 315                 320
Gly Ala Tyr Ala Pro Leu Thr Ala His Gly Thr Ile Leu Ile Asn Arg
                325                 330                 335
Val Leu Ala Ser Cys Tyr Ala Val Ile Glu Glu His Ser Trp Ala His
            340                 345                 350
Arg Ala Phe Ala Pro Phe Arg Leu Ala His Ala Leu Leu Ala Ala Leu
        355                 360                 365
Ala Pro Ala Arg Thr Asp Gly Gly Gly Gly Ser Ile Pro Ala Ala
    370                 375                 380
Gln Ser Ala Thr Glu Ala Arg Gly Ala Glu Pro Thr Ala Gly Ile His
385                 390                 395                 400
Trp Tyr Ser Gln Leu Leu Tyr His Ile Gly Thr Trp Leu Leu Asp Ser
                405                 410                 415
Glu Thr Met His Pro Leu Gly Met Ala Val Lys Ser Ser
            420                 425

<210> SEQ ID NO 5
<211> LENGTH: 1714
<212> TYPE: DNA
<213> ORGANISM: Rattus norvegicus

<400> SEQUENCE: 5
ttaaaatcag gctcttttg tcttttaatt gccgtctcga gacccaactc cgatgtgttc      60
cgttaccagc gaccggcagc ctgccatcgc agccctgtc tgggtgggga tcggagacaa    120
gtcccctgca gcaacagcag gcaaggttat ataggaagag aaagagccag gcagcgccag    180
agggaacgaa cgagccgagc gaggaaggga gagccgagcg caaggaggag cgcacacgca    240
cacacccgcg cgtaccagct cgcgcacaga ccggcgcggg gacggctcgc aagtcctcag    300
gttccgcgga cgagatgctg ctgctgctgg ccagatgttt tctggtggcc cttgcttcct    360
cgctgctggt gtgccccgga ctggcctgtg ggccggcag ggggtttgga aagaggcagc    420
accccaaaaa gctgacccct ttagcctaca agcagtttat ccccaacgta gccgagaaga    480 ccctagggc cagcggccga tatgaaggga agatcacaag aaactccgaa cgatttaagg    540
aactcacccc caattacaac cccgacatca tatttaagga tgaggaaaac actggagcag    600
```

-continued

```
accggctgat gactcagagg tgcaaagaca agttaaatgc cttggccatc tccgtgatga    660
accagtggcc tggagtgaag cttcgagtga ctgagggctg ggatgaggac ggccatcatt    720
cagaggagtc tctacactat gagggtcgag cagtggacat caccacgtct gacagggacc    780
gcagcaagta tggcatgctg gctcgcctgg ctgtggaggc tggattcgac tgggtctact    840
atgaatccaa agctcgcatc cactgctctg tgaaagcaga gaactccgtg gcggccaaat    900
ctgacggctg cttcccggga tcagccacag tgcacctgga gcagggtggc accaagttag    960
tgaaggatct aagtcccggg gaccgcgtgc tggcggctga cgaccagggc cggctgctgt   1020
acagcgactt cctcaccttc ctggaccgcg acgaaggtgc caagaaggtc ttctacgtga   1080
tcgagacgcg ggagccgcgg gagcgtctgc tgctcactgc cgcgcacctg ctcttcgtgg   1140
cgccgcacaa cgactccggg cccactccgg gaccgagccc actcttcgcc agccgcgtgc   1200
gtccggggca gcgcgtgtac gtggtggctg aacgcggcgg ggaccgccgg ctgctgcccg   1260
ccgcggtgca cagcgtaacg ctacgagagg aggcggcggg tgcgtacgcg ccgctcacgg   1320
cggacggcac cattctcatc aaccgggtgc tcgcctcgtg ctacgcagtc atcgaggagc   1380
acagctgggc acaccgggcc ttcgcgccct tccgcctggc gcacgcgctg ctggccgcgc   1440
tggcacccgc ccgcacggac ggcgggggcg ggggcagcat ccctgccccg caatctgtag   1500
cggaagcgag gggcgcaggg ccgcctgcgg gcatccactg gtactcgcag ctgctgtacc   1560
acattggcac ctggctgttg gacagcgaga ccctgcatcc cttgggaatg cagtcaagt   1620
ccagctgaag tccgacggga ccgggcaggg ggcgtggggg cgggcgggcg ggaagcgact   1680
gccagataag caaccgggaa agcgcacgga agga                                1714
```

<210> SEQ ID NO 6
<211> LENGTH: 437
<212> TYPE: PRT
<213> ORGANISM: Rattus norvegicus

<400> SEQUENCE: 6

```
Met Leu Leu Leu Leu Ala Arg Cys Phe Leu Val Ala Leu Ala Ser Ser
 1               5                  10                  15

Leu Leu Val Cys Pro Gly Leu Ala Cys Gly Pro Gly Arg Gly Phe Gly
            20                  25                  30

Lys Arg Gln His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
    50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Lys Leu Arg Val Thr Glu Gly
        115                 120                 125

Trp Asp Glu Asp Gly His His Ser Glu Glu Ser Leu His Tyr Glu Gly
    130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175
```

```
Glu Ser Lys Ala Arg Ile His Cys Ser Val Lys Ala Glu Asn Ser Val
            180                 185                 190

Ala Ala Lys Ser Asp Gly Cys Phe Pro Gly Ser Ala Thr Val His Leu
        195                 200                 205

Glu Gln Gly Gly Thr Lys Leu Val Lys Asp Leu Ser Pro Gly Asp Arg
    210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Arg Glu Pro Arg Glu Arg Leu Leu Thr Ala Ala His Leu
            260                 265                 270

Leu Phe Val Ala Pro His Asn Asp Ser Gly Pro Thr Pro Gly Pro Ser
        275                 280                 285

Pro Leu Phe Ala Ser Arg Val Arg Pro Gly Gln Arg Val Tyr Val Val
    290                 295                 300

Ala Glu Arg Gly Gly Asp Arg Arg Leu Leu Pro Ala Ala Val His Ser
305                 310                 315                 320

Val Thr Leu Arg Glu Glu Ala Ala Gly Ala Tyr Ala Pro Leu Thr Ala
                325                 330                 335

Asp Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
        355                 360                 365

Ala His Ala Leu Leu Ala Ala Leu Ala Pro Ala Arg Thr Asp Gly Gly
    370                 375                 380

Gly Gly Gly Ser Ile Pro Ala Pro Gln Ser Val Ala Glu Ala Arg Gly
385                 390                 395                 400

Ala Gly Pro Pro Ala Gly Ile His Trp Tyr Ser Gln Leu Leu Tyr His
                405                 410                 415

Ile Gly Thr Trp Leu Leu Asp Ser Glu Thr Leu His Pro Leu Gly Met
            420                 425                 430

Ala Val Lys Ser Ser
        435

<210> SEQ ID NO 7
<211> LENGTH: 1546
<212> TYPE: DNA
<213> ORGANISM: Xenopus laevis

<400> SEQUENCE: 7
cgagcagaga ttgcccataa ttactgtctc gtctctacac ccccatgtgt tctgtgagcg      60
gggagctgca ccctggactt tctgcacctg ccttgcttgg gatcggtggc tagaggggtc     120
ggcgaggagg cacaaggttg ctggaagcag cagcgaagga gaacatcctc tgagcctttg     180
atgtaattgg cttcgctcgg acgagatgct ggttgcgaac tcgaatctct gttggctgct     240
gagcttcatc tgcaccctgg tgaccccccc tgggctggca tgtggacctg gccgaggcat     300
tggcaagagg agacacccca aaaaactcac ccctctcgcc tataagcagt tcatccccaa     360
cgtggcggag aagaccctgg gggccagcgg cagatacgaa ggaaagatta caaggaactc     420
ggattgcttt aaagaattaa ccccccaatta taacccagat attatgttta aagacgagga     480
gagcaccggg gcggaccggc tcatgactca gagatgtaaa gacaaactga acgcactcgc     540
gatctccgtg atgaaccagt ggccgggggt gaagctgcgg gtgacggagg ggtgggatga     600
```

-continued

```
ggacgggcac cacttggagg agtcgctaca ttatgagggg agggcagtgg acatcactac       660
gtcggaccgg gaccgcagta aatacggaat gttgggccga ctggcggtgg aggccgggtt       720
cgactgggtc tattacgagt ccaaagctca tattcactgt tcggtcaaag cagagaactc       780
agtggcggcc aagtctggcg ggtgcttccc tgctggtgcc agggtgatgg tggaatttgg       840
tggcaccaaa gcggtgaaag acctgcgacc aggggaccgc gttctctcct ccgaccccca       900
agggaatctg ctctacagcg acttcctcat gttcatcgac caggagcgtg acgtcaagaa       960
gctcttttac gtcatcgaaa cgtctcagag aaaaattcgg ttgaccgcgg cccatctact      1020
ttttgtggcc cagaccaagg tcaacggcac caggtcgttc aagtctgtct ttgccagcaa      1080
catccaacca ggagatctca tttatacagc agaatcccaa gaccatgacc ttgaagggcg      1140
gggaaagtgg agaaggttga tcttgaggga ggacactgga gcttatgcgc tctaactgc       1200 ccatgggact gtggttatag accaggtatt ggcctcctgc tatgcagtca ttgaggaaca      1260
cacctgggca cacctcgcat tgcgccact gaggtttggc atgagcctct cctcttatat       1320
ttaccccaga gactccagtc ctccatcagg ccttcagcct caccaccaag ttgaccttca      1380
gtctcaccat caagttgatc ttcagtctca ccaccaagtt gaccttcagt ctcaccacca      1440
acttgaaggc atccactggt actcccagct actgtatcag atagggactt ggcttttgga      1500
cagtagctcc ctgcacccac tgggcatggc aacgaaatcc agttga                     1546
```

<210> SEQ ID NO 8
<211> LENGTH: 446
<212> TYPE: PRT
<213> ORGANISM: Xenopus laevis

<400> SEQUENCE: 8

```
Met Leu Val Ala Asn Ser Asn Leu Cys Trp Leu Leu Ser Phe Ile Cys
  1               5                  10                  15

Thr Leu Val Thr Pro Pro Gly Leu Ala Cys Gly Pro Gly Arg Gly Ile
             20                  25                  30

Gly Lys Arg Arg His Pro Lys Lys Leu Thr Pro Leu Ala Tyr Lys Gln
         35                  40                  45

Phe Ile Pro Asn Val Ala Glu Lys Thr Leu Gly Ala Ser Gly Arg Tyr
     50                  55                  60

Glu Gly Lys Ile Thr Arg Asn Ser Asp Cys Phe Lys Glu Leu Thr Pro
 65                  70                  75                  80

Asn Tyr Asn Pro Asp Ile Met Phe Lys Asp Glu Glu Ser Thr Gly Ala
                 85                  90                  95

Asp Arg Leu Met Thr Gln Arg Cys Lys Asp Lys Leu Asn Ala Leu Ala
            100                 105                 110

Ile Ser Val Met Asn Gln Trp Pro Gly Val Lys Leu Arg Val Thr Glu
        115                 120                 125

Gly Trp Asp Glu Asp Gly His His Leu Glu Ser Leu His Tyr Glu
    130                 135                 140

Gly Arg Ala Val Asp Ile Thr Thr Ser Asp Arg Asp Arg Ser Lys Tyr
145                 150                 155                 160

Gly Met Leu Gly Arg Leu Ala Val Glu Ala Gly Phe Asp Trp Val Tyr
                165                 170                 175

Tyr Glu Ser Lys Ala His Ile His Cys Ser Val Lys Ala Glu Asn Ser
            180                 185                 190

Val Ala Ala Lys Ser Gly Gly Cys Phe Pro Gly Ala Arg Val Met
        195                 200                 205
```

Val Glu Phe Gly Gly Thr Lys Ala Val Lys Asp Leu Arg Pro Gly Asp
210                 215                 220

Arg Val Leu Ser Ser Asp Pro Gln Gly Asn Leu Leu Tyr Ser Asp Phe
225                 230                 235                 240

Leu Met Phe Ile Asp Gln Glu Arg Asp Val Lys Lys Leu Phe Tyr Val
                245                 250                 255

Ile Glu Thr Ser Gln Arg Lys Ile Arg Leu Thr Ala Ala His Leu Leu
            260                 265                 270

Phe Val Ala Gln Thr Lys Val Asn Gly Thr Arg Ser Phe Lys Ser Val
        275                 280                 285

Phe Ala Ser Asn Ile Gln Pro Gly Asp Leu Ile Tyr Thr Ala Glu Ser
290                 295                 300

Gln Asp His Asp Leu Glu Gly Arg Gly Lys Trp Arg Arg Leu Ile Leu
305                 310                 315                 320

Arg Glu Asp Thr Gly Ala Tyr Ala Pro Leu Thr Ala His Gly Thr Val
                325                 330                 335

Val Ile Asp Gln Val Leu Ala Ser Cys Tyr Ala Val Ile Glu Glu His
            340                 345                 350

Thr Trp Ala His Leu Ala Phe Ala Pro Leu Arg Phe Gly Met Ser Leu
        355                 360                 365

Ser Ser Tyr Ile Tyr Pro Arg Asp Ser Ser Pro Pro Ser Gly Leu Gln
370                 375                 380

Pro His His Gln Val Asp Leu Gln Ser His His Gln Val Asp Leu Gln
385                 390                 395                 400

Ser His His Gln Val Asp Leu Gln Ser His His Gln Leu Glu Gly Ile
                405                 410                 415

His Trp Tyr Ser Gln Leu Leu Tyr Gln Ile Gly Thr Trp Leu Leu Asp
            420                 425                 430

Ser Ser Ser Leu His Pro Leu Gly Met Ala Thr Lys Ser Ser
        435                 440                 445

<210> SEQ ID NO 9
<211> LENGTH: 1261
<212> TYPE: DNA
<213> ORGANISM: Homo sapiens

<400> SEQUENCE: 9
cccagcgctg caaggaccgc ctgaactcgc tggctatctc ggtgatgaac cagtggcccg      60
gtgtgaagct gcgggtgacc gagggctggg acgaggacgg ccaccactca gaggagtccc     120
tgcattatga gggccgcgcg gtggacatca ccacatcaga ccgcgaccgc aataagtatg     180
gactgctggc gcgcttggca gtggaggccg gctttgactg ggtgtattac gagtcaaagg     240
cccacgtgca ttgctccgtc aagtccgagc actcggccgc agcaacgacg gcggctgct      300
tccctgccgg agcccaggta cgcctggaga gtggggcgcg tgtggccttg tcagccgtga     360
ggccgggaga ccgtgtgctg gccatggggg aggatgggag ccccaccttc agcgatgtgc     420
tcattttcct ggaccgcgag cctcacaggc tgagagcctt ccaggtcatc gagactcagg     480
accccccacg ccgcctggca ctcacacccg ctcacctgct ctttacggct gacaatcaca     540
cggagccggc agcccgcttc cgggccacat ttgccagcca cgtgcagcct ggccagtacg     600
tgctggtggc tggggtgcca ggcctgcagc ctgcccgcgt ggcagctgtc tctacacacg     660
tggccctcgg ggcctacgcc cgctcacaa agcatgggac actggtggtg gaggatgtgg     720
tggcatcctg cttcgcggcc gtggctgacc accacctggc tcagttggcc ttctggcccc     780

-continued

```
tgagactctt tcacagcttg gcatggggca gctggacccc ggggggagggt gtgcattggt    840 accccagct gctctaccgc ctggggcgtc tcctgctaga agagggcagc ttccacccac      900
tgggcatgtc cggggcaggg agctgaaagg actccaccgc tgccctcctg gaactgctgt    960
actgggtcca gaagcctctc agccaggagg gagctggccc tggaagggac ctgagctggg   1020
ggacactggc tcctgccatc tcctctgcca tgaagataca ccattgagac ttgactgggc    1080
aacaccagcg tccccaccc ccgtcgtggt gtagtcatag agctgcaagc tgagctggcg    1140 agggatggt tgttgacccc tctctcctag agaccttgag gctggcacgg cgactcccaa    1200
ctcagcctgc tctcactacg agttttcata ctctgcctcc cccattggga gggcccattc   1260
c                                                                   1261
```

<210> SEQ ID NO 10
<211> LENGTH: 293
<212> TYPE: PRT
<213> ORGANISM: Homo sapiens

<400> SEQUENCE: 10

```
Met Asn Gln Trp Pro Gly Val Lys Leu Arg Val Thr Glu Gly Trp Asp
  1               5                  10                  15

Glu Asp Gly His His Ser Glu Ser Leu His Tyr Glu Gly Arg Ala
             20                  25                  30

Val Asp Ile Thr Thr Ser Asp Arg Asp Arg Asn Lys Tyr Gly Leu Leu
         35                  40                  45

Ala Arg Leu Ala Val Glu Ala Gly Phe Asp Trp Val Tyr Tyr Glu Ser
     50                  55                  60

Lys Ala His Val His Cys Ser Val Lys Ser Glu His Ser Ala Ala Ala
 65                  70                  75                  80

Thr Thr Gly Gly Cys Phe Pro Ala Gly Ala Gln Val Arg Leu Glu Ser
                 85                  90                  95

Gly Ala Arg Val Ala Leu Ser Ala Val Arg Pro Gly Asp Arg Val Leu
            100                 105                 110

Ala Met Gly Glu Asp Gly Ser Pro Thr Phe Ser Asp Val Leu Ile Phe
        115                 120                 125

Leu Asp Arg Glu Pro His Arg Leu Arg Ala Phe Gln Val Ile Glu Thr
    130                 135                 140

Gln Asp Pro Pro Arg Arg Leu Ala Leu Thr Pro Ala His Leu Leu Phe
145                 150                 155                 160

Thr Ala Asp Asn His Thr Glu Pro Ala Ala Arg Phe Arg Ala Thr Phe
                165                 170                 175

Ala Ser His Val Gln Pro Gly Gln Tyr Val Leu Val Ala Gly Val Pro
            180                 185                 190

Gly Leu Gln Pro Ala Arg Val Ala Val Ser Thr His Val Ala Leu
        195                 200                 205

Gly Ala Tyr Ala Pro Leu Thr Lys His Gly Thr Leu Val Val Glu Asp
    210                 215                 220

Val Val Ala Ser Cys Phe Ala Val Ala Asp His His Leu Ala Gln
225                 230                 235                 240

Leu Ala Phe Trp Pro Leu Arg Leu Phe His Ser Leu Ala Trp Gly Ser
                245                 250                 255

Trp Thr Pro Gly Glu Gly Val His Trp Tyr Pro Gln Leu Leu Tyr Arg
            260                 265                 270

Leu Gly Arg Leu Leu Leu Glu Glu Gly Ser Phe His Pro Leu Gly Met
        275                 280                 285
```

Ser Gly Ala Gly Ser
    290

<210> SEQ ID NO 11
<211> LENGTH: 1277
<212> TYPE: DNA
<213> ORGANISM: Homo sapiens

<400> SEQUENCE: 11

```
ccggcgcctc atgacccagc gctgcaagga ccgcctgaac tcgctggcta tctcggtgat      60
gaaccagtgg cccggtgtga agctgcgggt gaccgagggc tgggacgagg acggccacca     120
ctcagaggag tccctgcatt atgagggccg cgcggtggac atcaccacat cagaccgcga     180
ccgcaataag tatggactgc tggcgcgctt ggcagtggag gccggctttg actgggtgta     240
ttacgagtca aaggcccacg tgcattgctc cgtcaagtcc gagcactcgg ccgcagccaa     300
gacgggcggc tgcttccctg ccggagccca ggtacgcctg gagagtgggg cgcgtgtggc     360
cttgtcagcc gtgaggccgg agaccgtgt gctggccatg ggggaggatg ggagccccac     420
cttcagcgat gtgctcattt cctggaccg gagccccac aggctgagag ccttccaggt      480
catcgagact caggaccccc cacgccgcct ggcactcaca cccgctcacc tgctctttac     540
ggctgacaat cacacggagc cggcagcccg cttccgggcc acatttgcca gccacgtgca     600
gcctggccag tacgtgctgg tggctggggt gccaggcctg cagcctgccc gcgtggcagc     660
tgtctctaca cacgtggccc tcggggccta cgccccgctc acaaagcatg ggacactggt     720
ggtggaggat gtggtggcat cctgcttcgc ggccgtggct gaccaccacc tggctcagtt     780
ggccttctgg cccctgagac tctttcacag cttggcatgg ggcagctgga ccccggggga     840
gggtgtgcat tggtacccccc agctgctcta ccgcctgggg cgtctcctgc tagaagaggg     900
cagcttccac ccactgggca tgtccggggc agggagctga aaggactcca ccgctgccct     960
cctggaactg ctgtactggg tccagaagcc tctcagccag gagggagctg ccctggaag    1020
ggacctgagc tggggacac tggctcctgc catctcctct gccatgaaga tacaccattg    1080
agacttgact gggcaacacc agcgtccccc acccgcgtcg tggtgtagtc atagagctgc    1140
aagctgagct ggcgagggga tggttgttga cccctctctc ctagagacct tgaggctggc    1200
acggcgactc ccaactcagc ctgctctcac tacgagtttt catactctgc ctcccccatt    1260
gggagggccc attcccc                                                   1277
```

<210> SEQ ID NO 12
<211> LENGTH: 312
<212> TYPE: PRT
<213> ORGANISM: Homo sapiens

<400> SEQUENCE: 12

Arg Arg Leu Met Thr Gln Arg Cys Lys Asp Arg Leu Asn Ser Leu Ala
1               5                   10                  15

Ile Ser Val Met Asn Gln Trp Pro Gly Val Lys Leu Arg Val Thr Glu
            20                  25                  30

Gly Trp Asp Glu Asp Gly His His Ser Glu Glu Ser Leu His Tyr Glu
        35                  40                  45

Gly Arg Ala Val Asp Ile Thr Thr Ser Asp Arg Asp Arg Asn Lys Tyr
    50                  55                  60

Gly Leu Leu Ala Arg Leu Ala Val Glu Ala Gly Phe Asp Trp Val Tyr
65                  70                  75                  80

Tyr Glu Ser Lys Ala His Val His Cys Ser Val Lys Ser Glu His Ser
                85                  90                  95

Ala Ala Ala Lys Thr Gly Gly Cys Phe Pro Ala Gly Ala Gln Val Arg
            100                 105                 110

Leu Glu Ser Gly Ala Arg Val Ala Leu Ser Ala Val Arg Pro Gly Asp
        115                 120                 125

Arg Val Leu Ala Met Gly Glu Asp Gly Ser Pro Thr Phe Ser Asp Val
    130                 135                 140

Leu Ile Phe Leu Asp Arg Glu Pro His Arg Leu Arg Ala Phe Gln Val
145                 150                 155                 160

Ile Glu Thr Gln Asp Pro Pro Arg Arg Leu Ala Leu Thr Pro Ala His
                165                 170                 175

Leu Leu Phe Thr Ala Asp Asn His Thr Glu Pro Ala Ala Arg Phe Arg
            180                 185                 190

Ala Thr Phe Ala Ser His Val Gln Pro Gly Gln Tyr Val Leu Val Ala
        195                 200                 205

Gly Val Pro Gly Leu Gln Pro Ala Arg Val Ala Ala Val Ser Thr His
    210                 215                 220

Val Ala Leu Gly Ala Tyr Ala Pro Leu Thr Lys His Gly Thr Leu Val
225                 230                 235                 240

Val Glu Asp Val Val Ala Ser Cys Phe Ala Ala Val Ala Asp His His
                245                 250                 255

Leu Ala Gln Leu Ala Phe Trp Pro Leu Arg Leu Phe His Ser Leu Ala
            260                 265                 270

Trp Gly Ser Trp Thr Pro Gly Glu Gly Val His Trp Tyr Pro Gln Leu
        275                 280                 285

Leu Tyr Arg Leu Gly Arg Leu Leu Leu Glu Glu Gly Ser Phe His Pro
    290                 295                 300

Leu Gly Met Ser Gly Ala Gly Ser
305                 310

<210> SEQ ID NO 13
<211> LENGTH: 1191
<212> TYPE: DNA
<213> ORGANISM: Mus musculus

<400> SEQUENCE: 13
atggctctgc cggccagtct gttgcccctg tgctgcttgg cactcttggc actatctgcc      60
cagagctgcg gccgggccg aggaccggtt ggccggcggc gttatgtgcg caagcaactt     120
gtgcctctgc tatacaagca gtttgtgccc agtatgcccg agcggaccct gggcgcgagt     180
gggccagcgg aggggagggt aacaaggggg tcggagcgct ccgggacct cgtacccaac      240 tacaaccccg acataatctt caaggatgag agaacagcg gcgcagaccg cctgatgaca      300
gagcgttgca aagagcgggt gaacgctcta gccatcgcgg tgatgaacat gtggcccgga     360
gtacgcctac gtgtgactga aggctgggac gaggacggcc accacgcaca ggattcactc     420
cactacgaag ccgtgccctt ggacatcacc acgtctgacc gtgaccgtaa taagtatggt     480
ttgttggcgc gcctagctgt ggaagccgga ttcgactggg tctactacga gtcccgcaac     540
cacatccacg tatcggtcaa agctgataac tcactggcgg tccgagccgg aggctgcttt     600
ccgggaaatg ccacggtgcg cttgcggagc ggcgaacgga aggggctgag gaactacat     660 cgtggtgact gggtactggc cgctgatgca gcgggccgag tggtacccac gccagtgctg      720
ctcttcctgg accgggatct gcagcgccgc gcctcgttcg tggctgtgga gaccgagcgg     780

```
cctccgcgca aactgttgct cacaccctgg catctggtgt tcgctgctcg cgggccagcg    840
cctgctccag gtgactttgc accggtgttc gcgcgccgct acgtgctgg cgactcggtg    900 ctggctcccg gcggggacgc gctccagccg gcgcgcgtag cccgcgtggc gcgcgaggaa    960
gccgtgggcg tgttcgcacc gctcactgcg cacgggacgc tgctggtcaa cgacgtcctc   1020
gcctcctgct acgcggttct agagagtcac cagtgggccc accgcgcctt cgccccttg    1080 cggctgctgc acgcgctcgg ggctctgctc cctgggggtg cagtccagcc gactggcatg   1140
cattggtact ctcgcctcct ttaccgcttg gccgaggagt taatgggctg a            1191
```

<210> SEQ ID NO 14
<211> LENGTH: 396
<212> TYPE: PRT
<213> ORGANISM: Mus musculus

<400> SEQUENCE: 14

```
Met Ala Leu Pro Ala Ser Leu Leu Pro Leu Cys Cys Leu Ala Leu Leu
 1               5                  10                  15

Ala Leu Ser Ala Gln Ser Cys Gly Pro Gly Arg Gly Pro Val Gly Arg
             20                  25                  30

Arg Arg Tyr Val Arg Lys Gln Leu Val Pro Leu Leu Tyr Lys Gln Phe
         35                  40                  45

Val Pro Ser Met Pro Glu Arg Thr Leu Gly Ala Ser Gly Pro Ala Glu
     50                  55                  60

Gly Arg Val Thr Arg Gly Ser Glu Arg Phe Arg Asp Leu Val Pro Asn
 65                  70                  75                  80

Tyr Asn Pro Asp Ile Ile Phe Lys Asp Glu Glu Asn Ser Gly Ala Asp
                 85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Ile His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Arg Ser Gly Glu Arg Lys Gly Leu Arg Glu Leu His Arg Gly Asp Trp
    210                 215                 220

Val Leu Ala Ala Asp Ala Ala Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Arg Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
    290                 295                 300
```

```
Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
    370                 375                 380

Arg Leu Leu Tyr Arg Leu Ala Glu Glu Leu Met Gly
385                 390                 395

<210> SEQ ID NO 15
<211> LENGTH: 3600
<212> TYPE: DNA
<213> ORGANISM: Homo sapiens

<400> SEQUENCE: 15
```

| | | | | | |
|---|---|---|---|---|---|
| cccagactcc | agccctggac | cgcgcatccc | gagcccagcg | cccagacaga | gtgtccccac | 60 |
| accctcctct | gagacgccat | gttcaactcg | atgccccac | caccaatcag | tagctatggc | 120 |
| gagccctgct | gtctccggcc | cctccccagt | caggggccc | ccagtgtggg | gacagaagga | 180 |
| ctgtctggcc | cgcccttctg | ccaccaagct | aacctcatgt | ccggccccca | cagttatggg | 240 |
| ccagccagag | agaccaacag | ctgcaccgag | ggcccactct | tttcttctcc | ccggagtgca | 300 |
| gtcaagttga | ccaagaagcg | ggcactgtcc | atctcacctc | tgtcggatgc | cagcctggac | 360 |
| ctgcagacgt | ttatccgcac | ctcacccagc | tccctcgtag | ctttcatcaa | ctcgcgatgc | 420 |
| acatctccag | gaggctccta | cggtcatctc | tccattggca | ccatgagccc | atctctggga | 480 |
| ttcccagccc | agatgaatca | ccaaaaaggg | ccctcgcctt | cctttggggt | ccagccttgt | 540 |
| ggtccccatg | actctgcccg | gggtgggatg | atcccacatc | ctcagtcccg | ggaccccttc | 600 |
| ccaacttgcc | agctgaagtc | tgagctggac | atgctggttg | gcaagtgccg | ggaggaaccc | 660 |
| ttggaaggtg | atatgtccag | ccccaactcc | acaggcatac | aggatcccct | gttggggatg | 720 |
| ctggatgggc | gggaggacct | cgagagagag | gagaagcgtg | agcctgaatc | tgtgtatgaa | 780 |
| actgactgcc | gttgggatgg | ctgcagccag | gaatttgact | cccaagagca | gctggtgcac | 840 |
| cacatcaaca | gcgagcacat | ccacggggag | cggaaggagt | tcgtgtgcca | ctggggggc | 900 |
| tgctccaggg | agctgaggcc | cttcaaagcc | cagtacatgc | tggtggttca | catgcgcaga | 960 |
| cacactggcg | agaagccaca | caagtgcacg | tttgaagggt | gccggaagtc | atactcacgc | 1020 |
| ctcgaaaacc | tgaagacgca | cctgcggtca | cacgggtg | agaagccata | catgtgtgag | 1080 |
| cacgagggct | gcagtaaagc | cttcagcaat | gccagtgacc | gagccaagca | ccagaatcgg | 1140 |
| acccattcca | atgagaagcc | gtatgtatgt | aagctccctg | ctgcaccaa | acgctataca | 1200 |
| gatcctagct | cgctgcgaaa | acatgtcaag | acagtgcatg | gtcctgacgc | ccatgtgacc | 1260 |
| aaacggcacc | gtggggatgg | cccctgcct | cgggcaccat | ccatttctac | agtggagccc | 1320 |
| aagagggagc | gggaaggagg | tccatcagg | gaggaaagca | gactgactgt | gccagagggt | 1380 |
| gccatgaagc | cacagccaag | ccctgggcc | cagtcatcct | gcagcagtga | ccactccccg | 1440 |
| gcagggagtg | cagccaatac | agacagtggt | gtggaaatga | ctggcaatgc | aggggcagc | 1500 |
| actgaagacc | tctccagctt | ggacgaggga | ccttgcattg | ctggcactgg | tctgtccact | 1560 |
| cttcgccgcc | ttgagaacct | caggctggac | cagctacatc | aactccggcc | aataggggacc | 1620 |

```
cggggtctca aactgcccag cttgtcccac accggtacca ctgtgtcccg ccgcgtgggc   1680 ccccccagtct ctcttgaacg ccgcagcagc agctccagca gcatcagctc tgcctatact   1740
gtcagccgcc gctcctccct ggcctctcct ttccccctg gctccccacc agagaatgga   1800
gcatcctccc tgcctggcct tatgcctgcc agcactacc tgcttcgggc aagatatgct   1860
tcagccagag gggtggtac ttcgcccact gcagcatcca gcctggatcg gataggtggt   1920
cttcccatgc ctccttggag aagccgagcc gagtatccag gatacaaccc caatgcaggg   1980
gtcacccgga gggccagtga cccagcccag gctgctgacc gtcctgctcc agctagagtc   2040
cagaggttca agagcctggg ctgtgtccat accccaccca ctgtggcagg gggaggacag   2100
aactttgatc cttacctccc aacctctgtc tactcaccac agcccccag catcactgag   2160 aatgctgcca tggatgctag agggctacag gaagagccag aagttgggac ctccatggtg   2220
ggcagtggtc tgaaccccta tatggacttc ccacctactg atactctggg atatggggga   2280
cctgaagggg cagcagctga gccttatgga gcgaggggtc caggctctct gcctcttggg   2340
cctggtccac ccaccaacta tggccccaac ccctgtcccc agcaggcctc atatcctgac   2400
cccacccaag aaacatgggg tgagttccct tcccactctg ggctgtaccc aggccccaag   2460
gctctaggtg gaacctacag ccagtgtcct cgacttgaac attatggaca agtgcaagtc   2520
aagccagaac aggggtgccc agtggggtct gactccacag gactggcacc ctgcctcaat   2580
gcccacccca gtgagggggcc cccacatcca cagcctctct tttcccatta ccccccagccc   2640 tctcctcccc aatatctcca gtcaggcccc tatacccagc caccccctga ttatcttcct   2700
tcagaaccca ggccttgcct ggactttgat tcccccaccc attccacagg gcagctcaag   2760
gctcagcttg tgtgtaatta tgttcaatct caacaggagc tactgtggga gggtgggggc   2820
agggaagatg cccccgccca ggaaccttcc taccagagtc ccaagtttct gggggttcc   2880 caggttagcc caagccgtgc taaagctcca gtgaacacat atggacctgg ctttggaccc   2940 aacttgcccq atcacaagtc aggttcctat cccaccccctt caccatgcca tgaaaatttt   3000
gtagtggggg caaatagggc ttcacatagg gcagcagcac cacctcgact tctgcccccca   3060 ttgcccactt gctatgggcc tctcaaagtg ggaggcacaa accccagctg tggtcatcct   3120
gaggtgggca ggctaggagg gggtcctgcc ttgtaccctc ctccccgaagg acaggtatgt   3180 aacccccctgg actctcttga tcttgacaac actcagctgg actttgtggc tattctggat   3240
gagccccagg ggctgagtcc tcctccttcc catgatcagc ggggcagctc tggacatacc   3300
ccacctccct ctgggccccc caacatggct gtgggcaaca tgagtgtctt actgagatcc   3360
ctacctgggg aaacagaatt cctcaactct agtgcctaaa gagtagggaa tctcatccat   3420
cacagatcgc atttcctaag gggtttctat ccttccagaa aaattggggg agctgcagtc   3480
ccctgcacaa gatgccccag ggatgggagg tatgggctgg gggctatgta tagtctgtat   3540
acgttttgag gagaaatttg ataatgacac tgtttcctga taataaagga actgcatcag   3600
```

<210> SEQ ID NO 16
<211> LENGTH: 1106
<212> TYPE: PRT
<213> ORGANISM: Homo sapiens

<400> SEQUENCE: 16

```
Met Phe Asn Ser Met Thr Pro Pro Ile Ser Ser Tyr Gly Glu Pro
  1               5                  10                  15

Cys Cys Leu Arg Pro Leu Pro Ser Gln Gly Ala Pro Ser Val Gly Thr
```

-continued

```
               20                  25                  30
Glu Gly Leu Ser Gly Pro Pro Phe Cys His Gln Ala Asn Leu Met Ser
             35                  40                  45
Gly Pro His Ser Tyr Gly Pro Ala Arg Glu Thr Asn Ser Cys Thr Glu
         50                  55                  60
Gly Pro Leu Phe Ser Ser Pro Arg Ser Ala Val Lys Leu Thr Lys Lys
 65                  70                  75                  80
Arg Ala Leu Ser Ile Ser Pro Leu Ser Asp Ala Ser Leu Asp Leu Gln
                 85                  90                  95
Thr Val Ile Arg Thr Ser Pro Ser Leu Val Ala Phe Ile Asn Ser
                100                 105                 110
Arg Cys Thr Ser Pro Gly Gly Ser Tyr Gly His Leu Ser Ile Gly Thr
             115                 120                 125
Met Ser Pro Ser Leu Gly Phe Pro Ala Gln Met Asn His Gln Lys Gly
         130                 135                 140
Pro Ser Pro Ser Phe Gly Val Gln Pro Cys Gly Pro His Asp Ser Ala
145                 150                 155                 160
Arg Gly Gly Met Ile Pro His Pro Gln Ser Arg Gly Pro Phe Pro Thr
                165                 170                 175
Cys Gln Leu Lys Ser Glu Leu Asp Met Leu Val Gly Lys Cys Arg Glu
             180                 185                 190
Glu Pro Leu Glu Gly Asp Met Ser Ser Pro Asn Ser Thr Gly Ile Gln
         195                 200                 205
Asp Pro Leu Leu Gly Met Leu Asp Gly Arg Glu Asp Leu Glu Arg Glu
210                 215                 220
Glu Lys Arg Glu Pro Glu Ser Val Tyr Glu Thr Asp Cys Arg Trp Asp
225                 230                 235                 240
Gly Cys Ser Gln Glu Phe Asp Ser Gln Glu Gln Leu Val His His Ile
                245                 250                 255
Asn Ser Glu His Ile His Gly Glu Arg Lys Glu Phe Val Cys His Trp
             260                 265                 270
Gly Gly Cys Ser Arg Glu Leu Arg Pro Phe Lys Ala Gln Tyr Met Leu
         275                 280                 285
Val Val His Met Arg Arg His Thr Gly Glu Lys Pro His Lys Cys Thr
290                 295                 300
Phe Glu Gly Cys Arg Lys Ser Tyr Ser Arg Leu Glu Asn Leu Lys Thr
305                 310                 315                 320
His Leu Arg Ser His Thr Gly Glu Lys Pro Tyr Met Cys Glu His Glu
                325                 330                 335
Gly Cys Ser Lys Ala Phe Ser Asn Ala Ser Asp Arg Ala Lys His Gln
             340                 345                 350
Asn Arg Thr His Ser Asn Glu Lys Pro Tyr Val Cys Lys Leu Pro Gly
         355                 360                 365
Cys Thr Lys Arg Tyr Thr Asp Pro Ser Ser Leu Arg Lys His Val Lys
         370                 375                 380
Thr Val His Gly Pro Asp Ala His Val Thr Lys Arg His Arg Gly Asp
385                 390                 395                 400
Gly Pro Leu Pro Arg Ala Pro Ser Ile Ser Thr Val Glu Pro Lys Arg
                405                 410                 415
Glu Arg Glu Gly Gly Pro Ile Arg Glu Glu Ser Arg Leu Thr Val Pro
             420                 425                 430
Glu Gly Ala Met Lys Pro Gln Pro Ser Pro Gly Ala Gln Ser Ser Cys
         435                 440                 445
```

```
Ser Ser Asp His Ser Pro Ala Gly Ser Ala Asn Thr Asp Ser Gly
    450                 455                 460

Val Glu Met Thr Gly Asn Ala Gly Gly Ser Thr Glu Asp Leu Ser Ser
465                 470                 475                 480

Leu Asp Glu Gly Pro Cys Ile Ala Gly Thr Gly Leu Ser Thr Leu Arg
                485                 490                 495

Arg Leu Glu Asn Leu Arg Leu Asp Gln Leu His Gln Leu Arg Pro Ile
            500                 505                 510

Gly Thr Arg Gly Leu Lys Leu Pro Ser Leu Ser His Thr Gly Thr Thr
        515                 520                 525

Val Ser Arg Arg Val Gly Pro Pro Val Ser Leu Glu Arg Arg Ser Ser
    530                 535                 540

Ser Ser Ser Ser Ile Ser Ser Ala Tyr Thr Val Ser Arg Arg Ser Ser
545                 550                 555                 560

Leu Ala Ser Pro Phe Pro Pro Gly Ser Pro Glu Asn Gly Ala Ser
                565                 570                 575

Ser Leu Pro Gly Leu Met Pro Ala Gln His Tyr Leu Leu Arg Ala Arg
            580                 585                 590

Tyr Ala Ser Ala Arg Gly Gly Gly Thr Ser Pro Thr Ala Ala Ser Ser
        595                 600                 605

Leu Asp Arg Ile Gly Gly Leu Pro Met Pro Pro Trp Arg Ser Arg Ala
    610                 615                 620

Glu Tyr Pro Gly Tyr Asn Pro Asn Ala Gly Val Thr Arg Arg Ala Ser
625                 630                 635                 640

Asp Pro Ala Gln Ala Ala Asp Arg Pro Ala Pro Ala Arg Val Gln Arg
                645                 650                 655

Phe Lys Ser Leu Gly Cys Val His Thr Pro Thr Val Ala Gly Gly
            660                 665                 670

Gly Gln Asn Phe Asp Pro Tyr Leu Pro Thr Ser Val Tyr Ser Pro Gln
        675                 680                 685

Pro Pro Ser Ile Thr Glu Asn Ala Ala Met Asp Ala Arg Gly Leu Gln
    690                 695                 700

Glu Glu Pro Glu Val Gly Thr Ser Met Val Gly Ser Gly Leu Asn Pro
705                 710                 715                 720

Tyr Met Asp Phe Pro Pro Thr Asp Thr Leu Gly Tyr Gly Gly Pro Glu
                725                 730                 735

Gly Ala Ala Ala Glu Pro Tyr Gly Ala Arg Gly Pro Gly Ser Leu Pro
            740                 745                 750

Leu Gly Pro Gly Pro Pro Thr Asn Tyr Gly Pro Asn Pro Cys Pro Gln
        755                 760                 765

Gln Ala Ser Tyr Pro Asp Pro Thr Gln Glu Thr Trp Gly Glu Phe Pro
    770                 775                 780

Ser His Ser Gly Leu Tyr Pro Gly Pro Lys Ala Leu Gly Gly Thr Tyr
785                 790                 795                 800

Ser Gln Cys Pro Arg Leu Glu His Tyr Gly Gln Val Gln Val Lys Pro
                805                 810                 815

Glu Gln Gly Cys Pro Val Gly Ser Asp Ser Thr Gly Leu Ala Pro Cys
            820                 825                 830

Leu Asn Ala His Pro Ser Glu Gly Pro Pro His Pro Gln Pro Leu Phe
        835                 840                 845

Ser His Tyr Pro Gln Pro Ser Pro Pro Gln Tyr Leu Gln Ser Gly Pro
    850                 855                 860
```

```
Tyr Thr Gln Pro Pro Asp Tyr Leu Pro Ser Glu Pro Arg Pro Cys
865                 870                 875                 880

Leu Asp Phe Asp Ser Pro Thr His Ser Thr Gly Gln Leu Lys Ala Gln
                885                 890                 895

Leu Val Cys Asn Tyr Val Gln Ser Gln Gln Glu Leu Leu Trp Glu Gly
            900                 905                 910

Gly Gly Arg Glu Asp Ala Pro Ala Gln Glu Pro Ser Tyr Gln Ser Pro
        915                 920                 925

Lys Phe Leu Gly Gly Ser Gln Val Ser Pro Ser Arg Ala Lys Ala Pro
    930                 935                 940

Val Asn Thr Tyr Gly Pro Gly Phe Gly Pro Asn Leu Pro Asn His Lys
945                 950                 955                 960

Ser Gly Ser Tyr Pro Thr Pro Ser Pro Cys His Glu Asn Phe Val Val
                965                 970                 975

Gly Ala Asn Arg Ala Ser His Arg Ala Ala Pro Pro Arg Leu Leu
            980                 985                 990

Pro Pro Leu Pro Thr Cys Tyr Gly Pro Leu Lys Val Gly Gly Thr Asn
            995                 1000                1005

Pro Ser Cys Gly His Pro Glu Val Gly Arg Leu Gly Gly Pro Ala
    1010                1015                1020

Leu Tyr Pro Pro Glu Gly Gln Val Cys Asn Pro Leu Asp Ser Leu
1025                1030                1035                1040

Asp Leu Asp Asn Thr Gln Leu Asp Phe Val Ala Ile Leu Asp Glu Pro
                1045                1050                1055

Gln Gly Leu Ser Pro Pro Ser His Asp Gln Arg Gly Ser Ser Gly
            1060                1065                1070

His Thr Pro Pro Pro Ser Gly Pro Pro Asn Met Ala Val Gly Asn Met
            1075                1080                1085

Ser Val Leu Leu Arg Ser Leu Pro Gly Glu Thr Glu Phe Leu Asn Ser
    1090                1095                1100

Ser Ala
1105

<210> SEQ ID NO 17
<211> LENGTH: 4909
<212> TYPE: DNA
<213> ORGANISM: Homo sapiens

<400> SEQUENCE: 17
gcgcccgccg ccttacctga ggccgccatc cacgccggtt gagtcgcgtt ctgccgcctc      60
ccgcctgtgg tgcctcctga actgcgtccg ccgtctagtg aagttcgtgg actcctacaa     120
taatgctata aatgcataga agaaaagaca caggactgtg aaagaaagtg atgatgcgat     180
gtctaaaacg ttcaaggcac cgcatctgtg atcaagaata catgtgctgc tttaccgaca     240
catcaaagag caaggattgc cacccaggac gatgagcggc tgagatggag acgtctgcct     300
cagccactgc ctccgagaag caagaagcca aaagtgggat cctggaggcc gctggcttcc     360
ccgacccggg taaaaaggcc tctcctttgg tggtggctgc agcggcagca gcagcggtag     420
ctgcccaagg agcccagcct tcaccttccc ccaccccatc aacccgtgg cctaccagca     480 gattctgagc cagcagaggg gtctggggtc agcctttgga cacacaccac ccctgatcca     540
gccctcaccc accttcctgg cccagcagcc catggccctc acctccatca atgccacgcc     600
cacccagctc agcagcagca gcaactgtct gagtgacacc aaccagaaca agcagagcag     660
tgagtcggcc gtcagcagca ccgtcaaccc tgtcgccatt cacaagcgca gcaaggtcaa     720
```

```
gaccgagcct gagggcctgc ggccggcctc ccctctggcg ctgacgcagg agcagctggc      780
tgacctcaag gaagatctgg acagggatga ctgtaagcag gaggctgagg tggtcatcta      840
tgagaccaac tgccactggg aagactgcac caaggagtac gacacccagg agcagctggt      900
gcatcacatc aacaacgagc acatccacgg ggagaagaag gagtttgtgt gccgctggca      960
ggcctgcacg cgggagcaga agcccttcaa ggcgcagtac atgctggtgg tgcacatgcg     1020
gcgacacacg ggcgagaagc ccacaagtg cacgttcgag ggctgctcga aggcctactc     1080
ccgcctggag aacctgaaga cacacctgcg gtcccacacc ggggagaagc catatgtgtg     1140
tgagcacgag ggctgcaaca aagccttctc caacgcctcg gaccgcgcca agcaccagaa     1200
tcgcacccac tccaacgaga aaccctacat ctgcaagatc ccaggctgca ccaagagata     1260
cacagacccc agctctctcc ggaagcatgt gaaaacggtc cacggcccag atgcccacgt     1320
caccaagaag cagcgcaatg acgtgcacct ccgcacaccg ctgctcaaag agaatgggga     1380
cagtgaggcc ggcacggagc ctggcggccc agagagcacc gaggccagca gcaccagcca     1440
ggccgtggag gactgcctgc acgtcagagc catcaagacc gagagctccg gctgtgtca      1500
gtccagcccc ggggcccagt cgtcctgcag cagcgagccc tctcctctgg gcagtgcccc     1560
caacaatgac agtggcgtgg agatgccggg gacggggccc gggagcctgg agacctgac      1620
ggcactggat gacacacccc caggggccga cacctcagcc ctggctgccc cctccgctgg     1680
tggcctccag ctgcgcaaac acatgaccac catgcaccgg ttcgagcagc tcaagaagga     1740
gaagctcaag tcactcaagg attcctgctc atgggccggg ccgactccac acacgcggaa     1800
caccaagctg cctcccctcc cgggaagtgg ctccatcctg gaaaacttca gtggcagtgg     1860
gggcggcggg cccgcggggc tgctgccgaa cccgcggctg tcggagctgt ccgcgagcga     1920
ggtgaccatg ctgagccagc tgcaggagcg ccgcgacagc tccaccagca cggtcagctc     1980
ggcctacacc gtgagccgcc gctcctccgg catctccccc tacttctcca gccgccgctc     2040
cagcgaggcc tcgcccctgg gcgccggccg cccgcacaac gcgagctccg ctgactccta     2100
cgaccccatc tccacggacg cgtcgcggcg ctcgagcgag gccagccagt gcagcggcgg     2160
ctccgggctg ctcaacctca cgccggcgca gcagtacagc ctgcgggcca gtacgcggc      2220
agccactggc ggccccccgc ccactccgct gccgggcctg gagcgcatga gcctgcggac     2280
caggctggcg ctgctggacg cggccgaggg cacgctgccc gccggctgcc cacgcccact     2340
ggggccgcgc cgtggcagcg acgggccgac ctatggccac ggccacgcgg ggctgcgcc      2400
cgccttcccc cacgaggctc caggcggcgg aaccaggcgg gccagcgacc ctgtgcggcg     2460
gcccgatgcc ctgtccctgc cgcgggtgca gcgcttccac agcacccaca cgtgaaccc      2520
cggcccgctg ccgccctgtg ccgacaggcg aggcctccgc ctgcagagcc acccgagcac     2580
cgacggcggc ctgccccgcg gcgcctactc gccccggccg cctagcatca gcgagaacgt     2640
ggcgatggag gccgtggcgg caggagtgga cggcgcgggg cccgaggccg acctggggct     2700
gccggaggac gacctggtgc ttccagacga cgtggtgcag tacatcaagg cgcacgccag     2760
tggcgctctg gacgagggca ccgggcaggt gtatcccacg gaaagcactg gcttctctga     2820
caacccaga ctaccagcc cggggctgca cggccagcgc aggatggtgg ctgcggactc     2880
caacgtgggc ccctccgccc ctatgctggg aggatgccag ttaggctttg gggcgccctc     2940
cagcctgaaa aaaataaca tgcctgtgca gtggaatgag gtgagctccg gcaccgtaga     3000
ctccctggcc agccaggtga agcctccacc ctttcctcag ggcaacctgg cggtggtgca     3060
```

-continued

```
gcagaagcct gcctttggcc agtacccggg ctacagtccg caaggcctac aggctagccc      3120
tgggggcctg gacagcacgc agccacacct gcagccccgc agcggagccc cctcccaggg      3180 catcccagg gtaaactaca tgcagcagct gcgacagcca gtggcaggca gccagtgtcc       3240
tggcatgact accactatga gccccatgc ctgctatggc caagtccacc cccagctgag       3300
ccccagcacc atcagtgggg ccctcaacca gttcccccaa tcctgcagca acatgccagc     3360
caagccaggg catctgggc accctcagca gacagaagtg gcacctgacc ccaccacgat      3420
gggcaatcgc acagggaac ttggggtccc caattcagcc ctggctggag tgccgccacc     3480
tcacccagtc cagagctacc cacagcagag ccatcacctg gcagcctcca tgagccagga   3540
gggctaccac caggtcccca gccttctgcc tgcccgccag cctggcttca tggagcccca     3600
aacaggcccg atgggggtgg ctacagcagg ctttggccta gtgcagcccc ggcctcccct    3660
cgagcccagc cccactggcc gccaccgtgg ggtacgtgct gtgcagcagc agctggccta    3720
cgccagggcc acaggccatg ccatggctgc catgccgtcc agtcaggaaa cagcagaggc    3780
tgtgcccaag ggagcgatgg gcaacatggg gtcggtgcct ccccagccgc ctccgcagga    3840
cgcaggtggg gccccggacc acagcatgct ctactactac ggccagatcc acatgtacga    3900
acaggatgga ggcctggaga acctcgggag ctgccaggtc atgcggtccc agccaccaca    3960
gccacaggcc tgtcaggaca gcatccagcc ccagcccttg ccctcaccag ggtcaaacca    4020
ggtgtccagc actgtggact cccagctcct ggaggccccc cagattgact tcgatgccat    4080
catggatgat ggcgatcact cgagtttgtt ctcgggtgct ctgagcccca gcctcctcca    4140
cagcctctcc cagaactcct cccgcctcac caccccccga aactccttga ccctgccctc    4200
catccccgca ggcatcagca acatggctgt cggggacatg agctccatgc tcaccagcct    4260
cgccgaggag agcaagttcc tgaacatgat gacctagagg cccgagcgcc tggtgctgag    4320
tgcacccgga ggggtcatcg ctgcccagag cctggggatt ccagctgtct tgtcttttc     4380 caaaaagtg ttaaataggc ttgagggtt gttgcgcaat ggccgcttca gatgacagat     4440
gttgtaagag aaggtttatg ggcatcctct ctggtctttt ggattattcc tcagaacaat    4500 gaaaaagtc tccataggac aggaaggaat gcaaaactca tttacacagt gctttccagc     4560
ctttggtgct acaggaccg cgctgttccg gcttcttcac ggctgacatt cggctaacga     4620
gggattactt tggccaaaac ctttcaaagg atatgcagaa agatggtagg gagcatttgg    4680
gtttgaatct gaatgctata ctggatactc tgctccggaa agatgagctt tttattctac    4740
tacttggaag gaaaaggaat tcctctatga agcctaactc ttgaggtctc taacatacct    4800
tgtcatagag gaaaagcaca gattatacct ggatgattca ggagagtgta tatgaatgaa   4860
taaggcatcc aagtatatat gaatgaataa agtatgtaag tatccaccag                4909
```

<210> SEQ ID NO 18
<211> LENGTH: 1241
<212> TYPE: PRT
<213> ORGANISM: Homo sapiens

<400> SEQUENCE: 18

```
Met Ala Leu Thr Ser Ile Asn Ala Thr Pro Thr Gln Leu Ser Ser Ser
 1               5                  10                  15

Ser Asn Cys Leu Ser Asp Thr Asn Gln Asn Lys Gln Ser Ser Glu Ser
             20                  25                  30

Ala Val Ser Ser Thr Val Asn Pro Val Ala Ile His Lys Arg Ser Lys
         35                  40                  45
```

-continued

```
Val Lys Thr Glu Pro Glu Gly Leu Arg Pro Ala Ser Pro Leu Ala Leu
 50                  55                  60

Thr Gln Glu Gln Leu Ala Asp Leu Lys Glu Asp Leu Asp Arg Asp Asp
 65                  70                  75                  80

Cys Lys Gln Glu Ala Glu Val Val Ile Tyr Glu Thr Asn Cys His Trp
                 85                  90                  95

Glu Asp Cys Thr Lys Glu Tyr Asp Thr Gln Glu Gln Leu Val His His
                100                 105                 110

Ile Asn Asn Glu His Ile His Gly Glu Lys Lys Glu Phe Val Cys Arg
            115                 120                 125

Trp Gln Ala Cys Thr Arg Glu Gln Lys Pro Phe Lys Ala Gln Tyr Met
130                 135                 140

Leu Val His Met Arg Arg His Thr Gly Glu Lys Pro His Lys Cys
145                 150                 155                 160

Thr Phe Glu Gly Cys Ser Lys Ala Tyr Ser Arg Leu Glu Asn Leu Lys
                165                 170                 175

Thr His Leu Arg Ser His Thr Gly Glu Lys Pro Tyr Val Cys Glu His
            180                 185                 190

Glu Gly Cys Asn Lys Ala Phe Ser Asn Ala Ser Asp Arg Ala Lys His
            195                 200                 205

Gln Asn Arg Thr His Ser Asn Glu Lys Pro Tyr Ile Cys Lys Ile Pro
210                 215                 220

Gly Cys Thr Lys Arg Tyr Thr Asp Pro Ser Ser Leu Arg Lys His Val
225                 230                 235                 240

Lys Thr Val His Gly Pro Asp Ala His Val Thr Lys Lys Gln Arg Asn
                245                 250                 255

Asp Val His Leu Arg Thr Pro Leu Leu Lys Glu Asn Gly Asp Ser Glu
            260                 265                 270

Ala Gly Thr Glu Pro Gly Gly Pro Glu Ser Thr Glu Ala Ser Ser Thr
            275                 280                 285

Ser Gln Ala Val Glu Asp Cys Leu His Val Arg Ala Ile Lys Thr Glu
290                 295                 300

Ser Ser Gly Leu Cys Gln Ser Ser Pro Gly Ala Gln Ser Ser Cys Ser
305                 310                 315                 320

Ser Glu Pro Ser Pro Leu Gly Ser Ala Pro Asn Asn Asp Ser Gly Val
                325                 330                 335

Glu Met Pro Gly Thr Gly Pro Gly Ser Leu Gly Asp Leu Thr Ala Leu
            340                 345                 350

Asp Asp Thr Pro Pro Gly Ala Asp Thr Ser Ala Leu Ala Ala Pro Ser
            355                 360                 365

Ala Gly Gly Leu Gln Leu Arg Lys His Met Thr Thr Met His Arg Phe
370                 375                 380

Glu Gln Leu Lys Lys Glu Lys Leu Lys Ser Leu Lys Asp Ser Cys Ser
385                 390                 395                 400

Trp Ala Gly Pro Thr Pro His Thr Arg Asn Thr Lys Leu Pro Pro Leu
                405                 410                 415

Pro Gly Ser Gly Ser Ile Leu Glu Asn Phe Ser Gly Ser Gly Gly Gly
            420                 425                 430

Gly Pro Ala Gly Leu Leu Pro Asn Pro Arg Leu Ser Glu Leu Ser Ala
            435                 440                 445

Ser Glu Val Thr Met Leu Ser Gln Leu Gln Glu Arg Arg Asp Ser Ser
450                 455                 460

Thr Ser Thr Val Ser Ser Ala Tyr Thr Val Ser Arg Arg Ser Ser Gly
```

```
            465                 470                 475                 480
Ile Ser Pro Tyr Phe Ser Ser Arg Arg Ser Ser Glu Ala Ser Pro Leu
                485                 490                 495
Gly Ala Gly Arg Pro His Asn Ala Ser Ser Ala Asp Ser Tyr Asp Pro
                500                 505                 510
Ile Ser Thr Asp Ala Ser Arg Arg Ser Ser Glu Ala Ser Gln Cys Ser
                515                 520                 525
Gly Gly Ser Gly Leu Leu Asn Leu Thr Pro Ala Gln Gln Tyr Ser Leu
                530                 535                 540
Arg Ala Lys Tyr Ala Ala Ala Thr Gly Gly Pro Pro Thr Pro Leu
545                 550                 555                 560
Pro Gly Leu Glu Arg Met Ser Leu Arg Thr Arg Leu Ala Leu Leu Asp
                565                 570                 575
Ala Ala Glu Gly Thr Leu Pro Ala Gly Cys Pro Arg Pro Leu Gly Pro
                580                 585                 590
Arg Arg Gly Ser Asp Gly Pro Thr Tyr Gly His Gly His Ala Gly Ala
                595                 600                 605
Ala Pro Ala Phe Pro His Glu Ala Pro Gly Gly Thr Arg Arg Ala
                610                 615                 620
Ser Asp Pro Val Arg Arg Pro Asp Ala Leu Ser Leu Pro Arg Val Gln
625                 630                 635                 640
Arg Phe His Ser Thr His Asn Val Asn Pro Gly Pro Leu Pro Pro Cys
                645                 650                 655
Ala Asp Arg Arg Gly Leu Arg Leu Gln Ser His Pro Ser Thr Asp Gly
                660                 665                 670
Gly Leu Ala Arg Gly Ala Tyr Ser Pro Arg Pro Pro Ser Ile Ser Glu
                675                 680                 685
Asn Val Ala Met Glu Ala Val Ala Ala Gly Val Asp Gly Ala Gly Pro
                690                 695                 700
Glu Ala Asp Leu Gly Leu Pro Glu Asp Asp Leu Val Leu Pro Asp Asp
705                 710                 715                 720
Val Val Gln Tyr Ile Lys Ala His Ala Ser Gly Ala Leu Asp Glu Gly
                725                 730                 735
Thr Gly Gln Val Tyr Pro Thr Glu Ser Thr Gly Phe Ser Asp Asn Pro
                740                 745                 750
Arg Leu Pro Ser Pro Gly Leu His Gly Gln Arg Arg Met Val Ala Ala
                755                 760                 765
Asp Ser Asn Val Gly Pro Ser Ala Pro Met Leu Gly Gly Cys Gln Leu
                770                 775                 780
Gly Phe Gly Ala Pro Ser Ser Leu Asn Lys Asn Asn Met Pro Val Gln
785                 790                 795                 800
Trp Asn Glu Val Ser Ser Gly Thr Val Asp Ser Leu Ala Ser Gln Val
                805                 810                 815
Lys Pro Pro Pro Phe Pro Gln Gly Asn Leu Ala Val Val Gln Gln Lys
                820                 825                 830
Pro Ala Phe Gly Gln Tyr Pro Gly Tyr Ser Pro Gln Gly Leu Gln Ala
                835                 840                 845
Ser Pro Gly Gly Leu Asp Ser Thr Gln Pro His Leu Gln Pro Arg Ser
                850                 855                 860
Gly Ala Pro Ser Gln Gly Ile Pro Arg Val Asn Tyr Met Gln Gln Leu
865                 870                 875                 880
Arg Gln Pro Val Ala Gly Ser Gln Cys Pro Gly Met Thr Thr Thr Met
                885                 890                 895
```

Ser Pro His Ala Cys Tyr Gly Gln Val His Pro Gln Leu Ser Pro Ser
            900                 905                 910

Thr Ile Ser Gly Ala Leu Asn Gln Phe Pro Gln Ser Cys Ser Asn Met
            915                 920                 925

Pro Ala Lys Pro Gly His Leu Gly His Pro Gln Gln Thr Glu Val Ala
            930                 935                 940

Pro Asp Pro Thr Thr Met Gly Asn Arg His Arg Glu Leu Gly Val Pro
945                 950                 955                 960

Asn Ser Ala Leu Ala Gly Val Pro Pro His Pro Val Gln Ser Tyr
            965                 970                 975

Pro Gln Gln Ser His His Leu Ala Ala Ser Met Ser Gln Glu Gly Tyr
            980                 985                 990

His Gln Val Pro Ser Leu Leu Pro Ala Arg Gln Pro Gly Phe Met Glu
            995                 1000                1005

Pro Gln Thr Gly Pro Met Gly Val Ala Thr Ala Gly Phe Gly Leu Val
            1010                1015                1020

Gln Pro Arg Pro Pro Leu Glu Pro Ser Pro Thr Gly Arg His Arg Gly
1025                1030                1035                1040

Val Arg Ala Val Gln Gln Gln Leu Ala Tyr Ala Arg Ala Thr Gly His
            1045                1050                1055

Ala Met Ala Met Pro Ser Ser Gln Glu Thr Ala Glu Ala Val Pro
            1060                1065                1070

Lys Gly Ala Met Gly Asn Met Gly Ser Val Pro Pro Gln Pro Pro
            1075                1080                1085

Gln Asp Ala Gly Gly Ala Pro Asp His Ser Met Leu Tyr Tyr Tyr Gly
            1090                1095                1100

Gln Ile His Met Tyr Glu Gln Asp Gly Gly Leu Glu Asn Leu Gly Ser
1105                1110                1115                1120

Cys Gln Val Met Arg Ser Gln Pro Pro Gln Pro Gln Ala Cys Gln Asp
            1125                1130                1135

Ser Ile Gln Pro Gln Pro Leu Pro Ser Pro Gly Val Asn Gln Val Ser
            1140                1145                1150

Ser Thr Val Asp Ser Gln Leu Leu Glu Ala Pro Gln Ile Asp Phe Asp
            1155                1160                1165

Ala Ile Met Asp Asp Gly Asp His Ser Ser Leu Phe Ser Gly Ala Leu
            1170                1175                1180

Ser Pro Ser Leu Leu His Ser Leu Ser Gln Asn Ser Ser Arg Leu Thr
1185                1190                1195                1200

Thr Pro Arg Asn Ser Leu Thr Leu Pro Ser Ile Pro Ala Gly Ile Ser
            1205                1210                1215

Asn Met Ala Val Gly Asp Met Ser Ser Met Leu Thr Ser Leu Ala Glu
            1220                1225                1230

Glu Ser Lys Phe Leu Asn Met Met Thr
            1235                1240

<210> SEQ ID NO 19
<211> LENGTH: 5054
<212> TYPE: DNA
<213> ORGANISM: Homo sapiens

<400> SEQUENCE: 19
cgatactacg tgggcatttt tggtcgaaga gagctgaagt aatgagaaga catcatggag      60
gcccagtccc acagctccac gaccactgaa aagaaaaaag ttgagaattc catagtgaag     120

-continued

```
tgctccactc gaacagatgt gagcgagaaa gccgttgcct ccagcaccac ttctaatgag      180
gatgaaagtc ctggacagac ttatcacaga gagagaagaa acgcaatcac tatgcagcca      240
cagaatgtcc aggggctcag caaagtcagt gaggaacctt caacatcgag tgacgagagg      300
gcctcattga tcaagaaaga gatccatggg tccctgccac acgtggcgga gccctctgtg      360
ccgtaccgcg ggacggtgtt tgccatggac cccaggaatg gttacatgga gccccactac      420
caccctcctc atcttttccc tgccttccat cctcctgtac caattgatgc cagacatcat      480
gagggccgtt accattacga tccatctccg attcctccat tgcatatgac ttccgcctta      540
tctagtagcc ctacgtatcc ggacctgccc ttcattagga tctccccaca ccggaacccc      600
gctgctgctt ccgagtctcc cttcagccct ccacatccct acattaatcc ctacatggac      660
tatatccgct ccttgcacag cagcccatcg ctctccatga tctcagcaac ccgtgggctg      720
agccctacag atgcgcccca tgcaggagtc agcccagcag aatactatca tcagatggcc      780
ctgctaactg gccagcgcag cccctatgca gacattattc cctcagctgc caccgccggc      840
acggggccca tccacatgga atatcttcat gctatggata gcaccagatt ctccagcccc      900
aggctgtcag ccaggccgag ccgaaaacgt acactgtcca tatcaccact ctccgatcat      960
agctttgacc ttcagaccat gataaggacg tctcccaact ccttggtcac gattctcaat     1020
aattcccgta gcagctcttc agcaagtggc tcctatggtc acttatctgc aagtgcaatc     1080
agccctgcct tgagcttcac ctactcttcc gcgcccgtct ctctccacat gcatcagcag     1140
atcctaagcc gacaacagag cttaggttca gcctttggac acagccctcc actcatccac     1200
cctgccccaa cttttccaac acagaggcct attccaggga tccctacggt tctgaacccc     1260
gtccaggtca gctccggccc ttctgagtcc tcacagaaca agcccacgag tgagtctgca     1320
gtgagcagca ctggtgaccc gatgcacaac aagaggtcca agatcaaacc cgatgaagac     1380
ctccccagcc caggggctcg ggggcagcag aacagcccg aaggaacaac ccttgtcaag     1440
gaggaagggg acaaagatga aagcaaacag gagcctgaag tcatctatga gacaaactgc     1500
cactgggaag gctgcgcgag ggagttcgac acccaagagc agcttgtgca ccatataaat     1560
aacgaccata ttcatggaga aagaaggag ttcgtgtgca ggtggctgga ctgctcaaga     1620
gagcagaaac ccttcaaagc ccagtatatg ttggtagtgc atatgagaag acacacgggc     1680
gagaagcctc acaaatgcac ttttgaaggt tgcacaaagg cctactcgag actagaaaac     1740
ttgaaaacac acttgagatc tcacactgga gagaaaccat acgtctgtga gcacgaaggt     1800
tgcaacaagg ctttctcaaa tgcctctgat cgcgccaaac accaaaacag aacgcattcc     1860
aatgagaaac catatgtgtg caaaatccca ggctgcacta agcgttacac agacccaagc     1920
tccctccgga aacatgtgaa gacagtgcat ggcccagagg ctcatgtcac caagaagcag     1980
cgagggacac tccatcctcg gccgccaccc ccgagagatt ccggcagcca ttcacagtcc     2040
aggtcgcctg gccgaccgac tcagggagcc cttggtgagc agcaggacct cagcaacact     2100
acctcaaagc gggaagaatg cctccaggtg aaaaccgtca aggcagagaa gccaatgaca     2160
tctcagccaa gccctggtgg tcagtcttca tgcagcagcc aacagtcccc catcagcaac     2220
tattccaaca gtgggctcga gcttcctctg accgatggag gtagtatagg agacctcagt     2280
gccatcgatg aaacccccaat catggactca accatttcca ctgcaaccac agcccttgct     2340
ttgcaagcca ggagaaaccc ggcagggacc aaatggatgg agcacgtaaa actagaaagg     2400
ctaaaacaag tgaatggaat gtttccgcga ctgaacccca ttctacccc taaagccct      2460 gcggtctctc ctctcatagg aaatggcaca cagtccaaca acacctgcag cttgggtggg     2520
```

```
cccatgacgc ttctcccggg cagaagcgac ctctctgggg tggacgtcac tatgctgaac  2580
atgctcaaca gaagggacag cagcgccagc accatcagct cggcctacct gagcagccgc  2640
cgctcctcag ggatctcgcc ctgcttctcc agccgccgct ccagcgaggc gtcacaggcc  2700
gagggccggc cgcagaacgt gagcgtggcc gactcctacg accccatctc caccgacgcc  2760
tcgcgccgct ccagcgaagc cagccagagc gacggcctgc ccagcctgct cagcctcacg  2820
cccgcccagc agtaccgcct caaggccaag tacgcggctg ccacaggagg gccgccgccg  2880
acgcccctgc ccaacatgga gaggatgagc ctgaagacgc gcctggcgct gctcggggat  2940
gccctcgagc ctggcgtggc cctgcctcca gttcatgccc cgaggaggtg cagcgacggg  3000
ggagcccacg gctacgggcg gcgccacctg cagccgcacg atgcgctggg ccacggcgtg  3060
aggagggcca gcgacccggt gcggacaggc tccgagggcc tggccctgcc tcgtgtgccg  3120
cgcttcagca gcctcagcag ctgcaacccc cggcgatgg ccacgtccgc ggagaagcgc  3180
agtctcgtgc ttcagaatta cacgcggccc gagggcggcc agtcccgaaa cttccactcg  3240 tcccctgtc ctcccagcat caccgagaac gtcaccctgg agtccctgac catggacgct  3300
gatgccaacc tgaacgatga ggatttcctg ccggacgacg tggtgcagta tttaaattcc  3360
cagaaccaag cagggtacga gcagcacttc cccagcgccc tcccggacga cagcaaagtg  3420
ccccacgggc ccggtgactt tgacgcgccc gggctgccag acagccacgc tggccagcag  3480
ttccatgccc tcgagcagcc ctgccccgag ggcagcaaaa ccgacctgcc cattcagtgg  3540
aacgaagtca gctccggaag cgccgacctg tcctcctcca agctcaagtg tgggccgcgg  3600
cccgctgtgc cgcagactcg cgcctttggg ttctgcaacg gcatggtcgt ccacccgcag  3660
aaccccttga ggagcgggcc tgctgggggc tatcagaccc tcggggagaa cagcaacccc  3720
tacggtggcc cagagcactt gatgctccac aacagccccg gaagtggcac cagtggaaac  3780
gccttccatg aacagccctg taaggccccg cagtatggga actgtctcaa caggcagcca  3840
gtggcccctg gtgcactcga cggtgcctgt ggtgccggga ttcaagcctc aaagctgaag  3900 agcacccca tgcaagggag cggggggcag ctgaatttcg gcctgccggt agcgccaaat  3960
gagtcagctg gcagcatggt gaatggcatg cagaaccagg acccagtggg acaggggtac  4020
ctggctcacc agctcctcgg cgacagcatg cagcacccgg gggcaggccg ccccggtcag  4080
cagatgcttg ggcagattag tgctacctca cacatcaaca tctaccaagg gccagagagc  4140
tgcctgccag gggctcacgg catgggcagc cagccgtcaa gcttggcagt tgtcagggc  4200 taccagccat gtgccagctt tggggcagc aggcgccagg ctatgccgag ggacagcctt  4260
gctctgcagt caggacagct cagtgacaca agtcagacct gcagggtgaa tggtatcaag  4320
atggagatga agggcagcc ccatccgctg tgctctaatc tgcagaatta ctctggtcag  4380
ttctatgacc aaaccgtggg cttcagtcag caagacacga agctggttc attctctatt  4440 tcagacgcca gctgcctgct acaggggacc agcgccaaaa actctgagtt actttcccca  4500
ggtgctaatc aggtgacaag cacagtggac agcctcgaca gccatgacct ggaaggggta  4560
cagattgact tcgatgccat catagacgat ggggaccact ccagcctgat gtcggggcc  4620 ctgagcccaa gtatcattca gaaccttttc catagctcct cccgcctcac cacgcctcgg  4680
gcgtccctcc cattcccagc gctgtccatg agcaccacca acatggctat cggggacatg  4740
agttctttgc tgacctccct agcggaagaa agcaaattcc ttgcagttat gcaataggct  4800
ttaggaaaaa aagactgcaa ccaacggaaa tcaataggag ttgaagagat taaactgact  4860
```

-continued

```
ttgttttggc tgttttttta gttctgtatg tattttagca atctcatctc acctaactga    4920
gatgtgtttc aattatattc cttttatgga aaaggactct gaaaaaccct aaagtattct    4980
agggagaaac tgtcttccat ttcagttttg aatcagtatt gttacactca aaccaccctc    5040
tttttaaaaa aaaa                                                      5054
```

```
<210> SEQ ID NO 20
<211> LENGTH: 1597
<212> TYPE: PRT
<213> ORGANISM: Homo sapiens
<220> FEATURE:
<221> NAME/KEY: VARIANT
<222> LOCATION: 1597
<223> OTHER INFORMATION: Xaa = Any Amino Acid

<400> SEQUENCE: 20
```

| | | | | | | | | | | | | | | | |
|---|---|---|---|---|---|---|---|---|---|---|---|---|---|---|---|
| Met | Glu | Ala | Gln | Ser | His | Ser | Ser | Thr | Thr | Thr | Glu | Lys | Lys | Lys | Val |
| 1 | | | | 5 | | | | | 10 | | | | | 15 | |

| Glu | Asn | Ser | Ile | Val | Lys | Cys | Ser | Thr | Arg | Thr | Asp | Val | Ser | Glu | Lys |
|---|---|---|---|---|---|---|---|---|---|---|---|---|---|---|---|
| | | | 20 | | | | | 25 | | | | | 30 | | |

| Ala | Val | Ala | Ser | Ser | Thr | Thr | Ser | Asn | Glu | Asp | Glu | Ser | Pro | Gly | Gln |
|---|---|---|---|---|---|---|---|---|---|---|---|---|---|---|---|
| | | 35 | | | | | 40 | | | | | 45 | | | |

| Thr | Tyr | His | Arg | Glu | Arg | Arg | Asn | Ala | Ile | Thr | Met | Gln | Pro | Gln | Asn |
|---|---|---|---|---|---|---|---|---|---|---|---|---|---|---|---|
| | 50 | | | | | 55 | | | | | 60 | | | | |

| Val | Gln | Gly | Leu | Ser | Lys | Val | Ser | Glu | Glu | Pro | Ser | Thr | Ser | Ser | Asp |
|---|---|---|---|---|---|---|---|---|---|---|---|---|---|---|---|
| 65 | | | | | 70 | | | | | 75 | | | | | 80 |

| Glu | Arg | Ala | Ser | Leu | Ile | Lys | Lys | Glu | Ile | His | Gly | Ser | Leu | Pro | His |
|---|---|---|---|---|---|---|---|---|---|---|---|---|---|---|---|
| | | | | 85 | | | | | 90 | | | | | 95 | |

| Val | Ala | Glu | Pro | Ser | Val | Pro | Tyr | Arg | Gly | Thr | Val | Phe | Ala | Met | Asp |
|---|---|---|---|---|---|---|---|---|---|---|---|---|---|---|---|
| | | | 100 | | | | | 105 | | | | | 110 | | |

| Pro | Arg | Asn | Gly | Tyr | Met | Glu | Pro | His | Tyr | His | Pro | His | Leu | Phe |
|---|---|---|---|---|---|---|---|---|---|---|---|---|---|---|
| | | 115 | | | | | 120 | | | | | 125 | | |

| Pro | Ala | Phe | His | Pro | Pro | Val | Pro | Ile | Asp | Ala | Arg | His | His | Glu | Gly |
|---|---|---|---|---|---|---|---|---|---|---|---|---|---|---|---|
| | 130 | | | | | 135 | | | | | 140 | | | | |

| Arg | Tyr | His | Tyr | Asp | Pro | Ser | Pro | Ile | Pro | Pro | Leu | His | Met | Thr | Ser |
|---|---|---|---|---|---|---|---|---|---|---|---|---|---|---|---|
| 145 | | | | | 150 | | | | | 155 | | | | | 160 |

| Ala | Leu | Ser | Ser | Ser | Pro | Thr | Tyr | Pro | Asp | Leu | Pro | Phe | Ile | Arg | Ile |
|---|---|---|---|---|---|---|---|---|---|---|---|---|---|---|---|
| | | | | 165 | | | | | 170 | | | | | 175 | |

| Ser | Pro | His | Arg | Asn | Pro | Ala | Ala | Ser | Glu | Ser | Pro | Phe | Ser | Pro |
|---|---|---|---|---|---|---|---|---|---|---|---|---|---|---|
| | | | 180 | | | | | 185 | | | | | 190 | |

| Pro | His | Pro | Tyr | Ile | Asn | Pro | Tyr | Met | Asp | Tyr | Ile | Arg | Ser | Leu | His |
|---|---|---|---|---|---|---|---|---|---|---|---|---|---|---|---|
| | | | | 195 | | | | | 200 | | | | | 205 | |

| Ser | Ser | Pro | Ser | Leu | Ser | Met | Ile | Ser | Ala | Thr | Arg | Gly | Leu | Ser | Pro |
|---|---|---|---|---|---|---|---|---|---|---|---|---|---|---|---|
| | 210 | | | | | 215 | | | | | 220 | | | | |

| Thr | Asp | Ala | Pro | His | Ala | Gly | Val | Ser | Pro | Ala | Glu | Tyr | Tyr | His | Gln |
|---|---|---|---|---|---|---|---|---|---|---|---|---|---|---|---|
| 225 | | | | | 230 | | | | | 235 | | | | | 240 |

| Met | Ala | Leu | Leu | Thr | Gly | Gln | Arg | Ser | Pro | Tyr | Ala | Asp | Ile | Ile | Pro |
|---|---|---|---|---|---|---|---|---|---|---|---|---|---|---|---|
| | | | | 245 | | | | | 250 | | | | | 255 | |

| Ser | Ala | Ala | Thr | Ala | Gly | Thr | Gly | Ala | Ile | His | Met | Glu | Tyr | Leu | His |
|---|---|---|---|---|---|---|---|---|---|---|---|---|---|---|---|
| | | | 260 | | | | | 265 | | | | | 270 | | |

| Ala | Met | Asp | Ser | Thr | Arg | Phe | Ser | Ser | Pro | Arg | Leu | Ser | Ala | Arg | Pro |
|---|---|---|---|---|---|---|---|---|---|---|---|---|---|---|---|
| | | 275 | | | | | 280 | | | | | 285 | | | |

| Ser | Arg | Lys | Arg | Thr | Leu | Ser | Ile | Ser | Pro | Leu | Ser | Asp | His | Ser | Phe |
|---|---|---|---|---|---|---|---|---|---|---|---|---|---|---|---|
| | 290 | | | | | 295 | | | | | 300 | | | | |

| Asp | Leu | Gln | Thr | Met | Ile | Arg | Ser | Pro | Asn | Ser | Leu | Val | Thr | Ile |
|---|---|---|---|---|---|---|---|---|---|---|---|---|---|---|
| 305 | | | | | 310 | | | | | 315 | | | | | 320 |

-continued

```
Leu Asn Asn Ser Arg Ser Ser Ser Ala Ser Gly Ser Tyr Gly His
            325                 330                 335
Leu Ser Ala Ser Ala Ile Ser Pro Ala Leu Ser Phe Thr Tyr Ser Ser
            340                 345                 350
Ala Pro Val Ser Leu His Met His Gln Gln Ile Leu Ser Arg Gln Gln
            355                 360                 365
Ser Leu Gly Ser Ala Phe Gly His Ser Pro Leu Ile His Pro Ala
370                 375                 380
Pro Thr Phe Pro Thr Gln Arg Pro Ile Pro Gly Ile Pro Thr Val Leu
385                 390                 395                 400
Asn Pro Val Gln Val Ser Ser Gly Pro Ser Glu Ser Ser Gln Asn Lys
            405                 410                 415
Pro Thr Ser Glu Ser Ala Val Ser Ser Thr Gly Asp Pro Met His Asn
            420                 425                 430
Lys Arg Ser Lys Ile Lys Pro Asp Glu Asp Leu Pro Ser Pro Gly Ala
            435                 440                 445
Arg Gly Gln Gln Glu Gln Pro Glu Gly Thr Thr Leu Val Lys Glu Glu
450                 455                 460
Gly Asp Lys Asp Glu Ser Lys Gln Glu Pro Glu Val Ile Tyr Glu Thr
465                 470                 475                 480
Asn Cys His Trp Glu Gly Cys Ala Arg Glu Phe Asp Thr Gln Glu Gln
            485                 490                 495
Leu Val His His Ile Asn Asn Asp His Ile His Gly Glu Lys Lys Glu
            500                 505                 510
Phe Val Cys Arg Trp Leu Asp Cys Ser Arg Glu Gln Lys Pro Phe Lys
            515                 520                 525
Ala Gln Tyr Met Leu Val Val His Met Arg Arg His Thr Gly Glu Lys
            530                 535                 540
Pro His Lys Cys Thr Phe Glu Gly Cys Thr Lys Ala Tyr Ser Arg Leu
545                 550                 555                 560
Glu Asn Leu Lys Thr His Leu Arg Ser His Thr Gly Glu Lys Pro Tyr
            565                 570                 575
Val Cys Glu His Glu Gly Cys Asn Lys Ala Phe Ser Asn Ala Ser Asp
            580                 585                 590
Arg Ala Lys His Gln Asn Arg Thr His Ser Asn Glu Lys Pro Tyr Val
            595                 600                 605
Cys Lys Ile Pro Gly Cys Thr Lys Arg Tyr Thr Asp Pro Ser Ser Leu
            610                 615                 620
Arg Lys His Val Lys Thr Val His Gly Pro Glu Ala His Val Thr Lys
625                 630                 635                 640
Lys Gln Arg Gly Asp Ile His Pro Arg Pro Pro Pro Arg Asp Ser
            645                 650                 655
Gly Ser His Ser Gln Ser Arg Ser Pro Gly Arg Pro Thr Gln Gly Ala
            660                 665                 670
Leu Gly Glu Gln Gln Asp Leu Ser Asn Thr Thr Ser Lys Arg Glu Glu
            675                 680                 685
Cys Leu Gln Val Lys Thr Val Lys Ala Glu Lys Pro Met Thr Ser Gln
            690                 695                 700
Pro Ser Pro Gly Gly Gln Ser Ser Cys Ser Ser Gln Gln Ser Pro Ile
705                 710                 715                 720
Ser Asn Tyr Ser Asn Ser Gly Leu Glu Leu Pro Leu Thr Asp Gly Gly
            725                 730                 735
```

-continued

```
Ser Ile Gly Asp Leu Ser Ala Ile Asp Glu Thr Pro Ile Met Asp Ser
            740                 745                 750

Thr Ile Ser Thr Ala Thr Thr Ala Leu Ala Leu Gln Ala Arg Arg Asn
        755                 760                 765

Pro Ala Gly Thr Lys Trp Met Glu His Val Lys Leu Glu Arg Leu Lys
    770                 775                 780

Gln Val Asn Gly Met Phe Pro Arg Leu Asn Pro Ile Leu Pro Pro Lys
785                 790                 795                 800

Ala Pro Ala Val Ser Pro Leu Ile Gly Asn Gly Thr Gln Ser Asn Asn
                805                 810                 815

Thr Cys Ser Leu Gly Gly Pro Met Thr Leu Leu Pro Gly Arg Ser Asp
            820                 825                 830

Leu Ser Gly Val Asp Val Thr Met Leu Asn Met Leu Asn Arg Arg Asp
        835                 840                 845

Ser Ser Ala Ser Thr Ile Ser Ser Ala Tyr Leu Ser Ser Arg Arg Ser
    850                 855                 860

Ser Gly Ile Ser Pro Cys Phe Ser Ser Arg Arg Ser Ser Glu Ala Ser
865                 870                 875                 880

Gln Ala Glu Gly Arg Pro Gln Asn Val Ser Val Ala Asp Ser Tyr Asp
                885                 890                 895

Pro Ile Ser Thr Asp Ala Ser Arg Arg Ser Ser Glu Ala Ser Gln Ser
            900                 905                 910

Asp Gly Leu Pro Ser Leu Leu Ser Leu Thr Pro Ala Gln Gln Tyr Arg
        915                 920                 925

Leu Lys Ala Lys Tyr Ala Ala Ala Thr Gly Gly Pro Pro Thr Pro
    930                 935                 940

Leu Pro Asn Met Glu Arg Met Ser Leu Lys Thr Arg Leu Ala Leu Leu
945                 950                 955                 960

Gly Asp Ala Leu Glu Pro Gly Val Ala Leu Pro Pro Val His Ala Pro
                965                 970                 975

Arg Arg Cys Ser Asp Gly Gly Ala His Gly Tyr Gly Arg Arg His Leu
            980                 985                 990

Gln Pro His Asp Ala Leu Gly His Gly Val Arg Arg Ala Ser Asp Pro
        995                 1000                1005

Val Arg Thr Gly Ser Glu Gly Leu Ala Leu Pro Arg Val Pro Arg Phe
    1010                1015                1020

Ser Ser Leu Ser Ser Cys Asn Pro Pro Ala Met Ala Thr Ser Ala Glu
1025                1030                1035                1040

Lys Arg Ser Leu Val Leu Gln Asn Tyr Thr Arg Pro Glu Gly Gly Gln
                1045                1050                1055

Ser Arg Asn Phe His Ser Ser Pro Cys Pro Pro Ser Ile Thr Glu Asn
            1060                1065                1070

Val Thr Leu Glu Ser Leu Thr Met Asp Ala Asp Ala Asn Leu Asn Asp
        1075                1080                1085

Glu Asp Phe Leu Pro Asp Asp Val Val Gln Tyr Leu Asn Ser Gln Asn
    1090                1095                1100

Gln Ala Gly Tyr Glu Gln His Phe Pro Ser Ala Leu Pro Asp Asp Ser
1105                1110                1115                1120

Lys Val Pro His Gly Pro Gly Asp Phe Asp Ala Pro Gly Leu Pro Asp
                1125                1130                1135

Ser His Ala Gly Gln Gln Phe His Ala Leu Glu Gln Pro Cys Pro Glu
            1140                1145                1150

Gly Ser Lys Thr Asp Leu Pro Ile Gln Trp Asn Glu Val Ser Ser Gly
```

```
                  1155                1160                1165
Ser Ala Asp Leu Ser Ser Lys Leu Lys Cys Gly Pro Arg Pro Ala
    1170                1175                1180
Val Pro Gln Thr Arg Ala Phe Gly Phe Cys Asn Gly Met Val Val His
1185                1190                1195                1200
Pro Gln Asn Pro Leu Arg Ser Gly Pro Ala Gly Gly Tyr Gln Thr Leu
            1205                1210                1215
Gly Glu Asn Ser Asn Pro Tyr Gly Gly Pro Glu His Leu Met Leu His
            1220                1225                1230
Asn Ser Pro Gly Ser Gly Thr Ser Gly Asn Ala Phe His Glu Gln Pro
        1235                1240                1245
Cys Lys Ala Pro Gln Tyr Gly Asn Cys Leu Asn Arg Gln Pro Val Ala
        1250                1255                1260
Pro Gly Ala Leu Asp Gly Ala Cys Gly Ala Gly Ile Gln Ala Ser Lys
1265                1270                1275                1280
Leu Lys Ser Thr Pro Met Gln Gly Ser Gly Gln Leu Asn Phe Gly
                1285                1290                1295
Leu Pro Val Ala Pro Asn Glu Ser Ala Gly Ser Met Val Asn Gly Met
            1300                1305                1310
Gln Asn Gln Asp Pro Val Gly Gln Gly Tyr Leu Ala His Gln Leu Leu
            1315                1320                1325
Gly Asp Ser Met Gln His Pro Gly Ala Gly Arg Pro Gly Gln Gln Met
        1330                1335                1340
Leu Gly Gln Ile Ser Ala Thr Ser His Ile Asn Ile Tyr Gln Gly Pro
1345                1350                1355                1360
Glu Ser Cys Leu Pro Gly Ala His Gly Met Gly Ser Gln Pro Ser Ser
                1365                1370                1375
Leu Ala Val Val Arg Gly Tyr Gln Pro Cys Ala Ser Phe Gly Gly Ser
            1380                1385                1390
Arg Arg Gln Ala Met Pro Arg Asp Ser Leu Ala Leu Gln Ser Gly Gln
            1395                1400                1405
Leu Ser Asp Thr Ser Gln Thr Cys Arg Val Asn Gly Ile Lys Met Glu
        1410                1415                1420
Met Lys Gly Gln Pro His Pro Leu Cys Ser Asn Leu Gln Asn Tyr Ser
1425                1430                1435                1440
Gly Gln Phe Tyr Asp Gln Thr Val Gly Phe Ser Gln Asp Thr Lys
                1445                1450                1455
Ala Gly Ser Phe Ser Ile Ser Asp Ala Ser Cys Leu Leu Gln Gly Thr
            1460                1465                1470
Ser Ala Lys Asn Ser Glu Leu Leu Ser Pro Gly Ala Asn Gln Val Thr
            1475                1480                1485
Ser Thr Val Asp Ser Leu Asp Ser His Asp Leu Glu Gly Val Gln Ile
        1490                1495                1500
Asp Phe Asp Ala Ile Asp Asp Gly Asp His Ser Ser Leu Met Ser
1505                1510                1515                1520
Gly Ala Leu Ser Pro Ser Ile Ile Gln Asn Leu Ser His Ser Ser Ser
                1525                1530                1535
Arg Leu Thr Thr Pro Arg Ala Ser Leu Pro Phe Pro Val Ala Val His
            1540                1545                1550
Glu His His Gln His Gly Tyr Arg Gly His Glu Phe Phe Ala Asp Leu
        1555                1560                1565
Pro Ser Gly Arg Lys Gln Ile Pro Cys Ser Tyr Ala Ile Gly Phe Arg
        1570                1575                1580
```

Lys Lys Arg Leu Gln Pro Thr Glu Ile Asn Arg Ser Xaa
1585                1590                1595

<210> SEQ ID NO 21
<211> LENGTH: 21
<212> TYPE: DNA
<213> ORGANISM: Artificial Sequence
<220> FEATURE:
<223> OTHER INFORMATION: synthetic

<400> SEQUENCE: 21
aactccacag gcatacagga t                                    21

<210> SEQ ID NO 22
<211> LENGTH: 21
<212> TYPE: DNA
<213> ORGANISM: Artificial Sequence
<220> FEATURE:
<223> OTHER INFORMATION: synthetic

<400> SEQUENCE: 22
aagatctgga cagggatgac t                                    21

<210> SEQ ID NO 23
<211> LENGTH: 21
<212> TYPE: DNA
<213> ORGANISM: Artificial Sequence
<220> FEATURE:
<223> OTHER INFORMATION: synthetic

<400> SEQUENCE: 23
aatgatctct gccgccaggg g                                    21

<210> SEQ ID NO 24
<211> LENGTH: 21
<212> TYPE: DNA
<213> ORGANISM: Artificial Sequence
<220> FEATURE:
<223> OTHER INFORMATION: synthetic

<400> SEQUENCE: 24
aatgaggatg aaagtcctgg a                                    21

<210> SEQ ID NO 25
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 25
gcacagaacg caggtaatgc tccat                                25

<210> SEQ ID NO 26
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 26
gagattcgag ttcgcaacca gcatc                                25

<210> SEQ ID NO 27
<211> LENGTH: 25

```
<212> TYPE: DNA
<213> ORGANISM: Artificial Sequence
<220> FEATURE:
<223> OTHER INFORMATION: primer

<400> SEQUENCE: 27
tcacccacac tgtgcccatc tacga                                          25

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
cagcggaacc gctcattgcc aatgg                                          25

<210> SEQ ID NO 29
<211> LENGTH: 21
<212> TYPE: RNA
<213> ORGANISM: Artificial Sequence
<220> FEATURE:
<223> OTHER INFORMATION: synthetic

<400> SEQUENCE: 29
aacuccacag gcauacagga u                                              21

<210> SEQ ID NO 30
<211> LENGTH: 21
<212> TYPE: RNA
<213> ORGANISM: Artificial Sequence
<220> FEATURE:
<223> OTHER INFORMATION: synthetic

<400> SEQUENCE: 30
aacguacgcg gaauacaacg a                                              21

<210> SEQ ID NO 31
<211> LENGTH: 21
<212> TYPE: RNA
<213> ORGANISM: Artificial Sequence
<220> FEATURE:
<223> OTHER INFORMATION: synthetic

<400> SEQUENCE: 31
aagaucugga cagggaugac u                                              21

<210> SEQ ID NO 32
<211> LENGTH: 21
<212> TYPE: RNA
<213> ORGANISM: Artificial Sequence
<220> FEATURE:
<223> OTHER INFORMATION: synthetic

<400> SEQUENCE: 32
aaugaggaug aaaguccugg a                                              21

<210> SEQ ID NO 33
<211> LENGTH: 22
<212> TYPE: DNA
```

```
<213> ORGANISM: Artificial Sequence
<220> FEATURE:
<223> OTHER INFORMATION: synthetic

<400> SEQUENCE: 33
cgggcggaca ctggcgggac gc                                              22
```

METHOD AND COMPOSITIONS FOR INHIBITING TUMORIGENESIS

CROSS-REFERENCE TO RELATED APPLICATIONS

The present application is a Continuation-in-Part of U.S. Ser. No. 10/456,954, filed Jun. 6, 2003 now abandoned, which is a Continuation-in-Part of non-provisional application U.S. Ser. No. 09/825,155, filed Apr. 3, 2001 now abandoned, which is a Continuation of U.S. Ser. No. 09/102,491, filed Jun. 22, 1998, now U.S Pat. No. 6,238,876, which claims benefit of priority to provisional application 60/050,286, filed Jun. 20, 1997; and is also a Continuation-in-Part of non-provisional application U.S. Ser. No. 10/414,267, filed Apr. 15, 2003 now abandoned, which claims the benefit of priority to provisional application U.S. Ser. No. 60/372,508, filed Apr. 15, 2002; and is also a Continuation-in-Part of non-provisional application U.S. Ser. No. 10/927,951, filed Aug. 29, 2004 now abandoned which is a Continuation-in-Part of non-provisional application U.S. Ser. No. 10/456,954, filed Jun. 6, 2003 now abandoned. Applicants claim the benefit of all of the above applications under 35 U.S.C. §119(e) and 35 U.S.C. §120, and the disclosures of all of the above applications are incorporated herein by reference in their entireties.

GOVERNMENTAL SUPPORT

The research leading to the present invention was supported, at least in part, by grants from the National Institute of Neurological Disorders and Stroke, Grant No. R01 NS-37352, and from the National Cancer Institute, Grant No. R01 CA78736. Accordingly, the Government may have certain rights in the invention.

FIELD OF THE INVENTION

The present invention relates generally to the diagnosis and treatment of pathologies involving tumor formation and neoplasia, and more particularly to compositions and methods of inhibiting tumorigenesis, tumor cell growth and/or survival using agents that inhibit the sonic hedgehog (SHH or HH) and GLI signaling pathway. The present invention also relates to particular biomarkers that can be used in the diagnosis and prognosis of cancer. Methods of treating cancer, including but not limited to lung cancer are also provided through the use of relevant therapeutic agents based on their effect on the level of expression and/or activity of GLI genes. Small organic compounds, siRNAs and blocking antibodies that inhibit or block the SHH/GLI pathway are contemplated for the preparation of therapeutic compositions and methods of use.

BACKGROUND OF THE INVENTION

Inductive signaling plays a critical role in both normal and disease development as developmental pathways that become unregulated in the adult can lead to abnormal patterning, overproliferation and neoplasia. One signaling pathway that is involved in several patterning events during embryogenesis is that triggered by secreted sonic hedgehog (Shh) (Echelard, Y., Epstein, D. J., St-Jacques, B., Shen, L., Mohler, J., McMahon, J. A. & McMahon, A. P., *Cell* 75, 1417-1430 (1993); Riddle, R., Johnson, R. L., Laufer, E. & Tabin, C.,*Cell* 75, 1401-1418 (1993); Krauss, S., Concordet, J.-P. & Ingham, P. W, *Cell* 75, 1431-1444 (1993); Roelink, H., Augsburger, A., Heemskerk, J., Korzh, V., Norlin, S., Ruiz i Altaba, A., Tanabe, Y., Placzek, M., Edlund, T., Jessell, T. M. & Dodd, J., *Cell* 76, 761-775 (1994)). Shh binding to the membrane patched (ptc)-smoothened (smo) receptor complex elicits a cascade of cytoplasmic signal transduction events, including the inhibition of protein kinase A (PKA) (Fan, C.-M., Porter, J. A., Chiang, C., Chang, D. T., Beachy, P. A. & Tessier-Lavigne, M., *Cell* 81, 457-465 (1995); Hynes, M., Porter, J. A., Chiang, C., Chang, D., Tessier-Lavigne, M., Beachy, P. A. & Rosenthal, A., *Neuron* 15, 35-34 (1995); Concordet, J.-P., Lewis, K. E., Moore, J., Goodrich, L. V., Johnson, R. L., Scott, M. P. & Ingham, P. W., *Development* 122, 2835-2846 (1996); Epstein, D. J., Marti, E., Scott, M. P. & McMahon, A. P., *Development* 122, 2885-2894 (1996); Goodrich, L. V., Johnson, R. L., Milenkovic, L., McMahon, J. A. & Scott, M. P., *Genes Dev.* 10, 301-312 (1996); Hammerschmidt, M., Bitgood, M. J. & McMahon, A. P., *Genes and Dev.* 10, 647-658 (1996); Marigo, V., Johnson, R. L., Vortkamp, A. & Tabin, C. J., *Dev. Biol.* 180, 273-283 (1996); Stone, D. M., Hynes, M., Armanini, M., Swanson, T. A., Gu, Q., Johnson, R. L., Scott, M. P., Pennica, D., Goddard, A., Phillips, H., Noll, M., Hooper, J. E., de Sauvage, F. & Rosenthal, A., *Nature* 384, 129-134 (1996)) that leads to the transcription of the zinc finger transcription factor gene Gli1 (Marigo, V., Johnson, R. L., Vortkamp, A. & Tabin, C. J., *Dev. Biol.* 180, 273-283 (1996); Lee, J., Platt, K. A., Censullo, P. & Ruiz i Altaba, A. , *Development (*1997)). Gli1 is a proto-oncogene first isolated as an amplified gene in a glioma that can transform fibroblasts in cooperation with E1A (Kinzler, K. W., Bigner, S. H., Bigner, D. D., Trent, J. M., Law, M. L., O'Brien, S. J., Wong, A. J. & Vogelstin, B., *Science* 236, 70-73 (1987); Ruppert, J. M., Vogelstein, B. & Kinzler, K. W., *Molecular and Cellular Biology* 11, 1724-1728 (1991)). Gli1 is a member of a family comprising two other related genes: Gli2 and Gli3 (Ruppert, J. M., Vogelstein, B., Arheden, K. & Kinzler, K. W., *Mol. Cell Biol.* 10, 5408-5415 (1990); Hui, C.-C., Slusarski, D., Platt, K. A., Holmgren, R. & Joyner, A. L., *Developmental Biology* 162, 402-413 (1994)). However, only Gli1 has been shown to be a target of Shh and mimic its effects (Lee, J., Platt, K. A., Censullo, P. & Ruiz i Altaba, A., *Development (*1997)). In *Drosophila*, hedgehog signaling (Forbes, A. J., Nakano, Y., Taylor, A. M. & Ingham, P. W., *Development Supplement* 115-124 (1993)) similarly leads to the action of cubitus interruptus (ci), a Gli homolog that activates transcription of hedgehog-target genes (Domínguez, M., Brunner, M., Hafen, E. & Basler, K., *Science* 272, 1621-1625 (1996); Alexandre, C., Jacinto, A. & Ingham, P. W., *Genes and Dev.* 10, 2003-2013 (1996); Hepker, J., Wang, Q.-T., Motzny, C. K., Holmgren, R. & Orenic, T. V., *Development* 124, 549-558 (1997); von Ohnen, T., Lessing, D., Nusse, R. & Hooper, J. E., *Proc. Natl. Acad. Sci. USA.* 94, 2404-2409 (1997); Mullor, J. L., Calleja, M., Capdevila, J. & Guerrero, I., *Development* 124, 1227-1237 (1997)).

One of the processes in which Shh signaling is involved is the differentiation of ventral neural tube cell types acting as a notochord and floor plate-derived signal (Echelard, Y., Epstein, D. J., St-Jacques, B., Shen, L., Mohler, J., McMahon, J. A. & McMahon, A. P., *Cell* 75, 1417-1430 (1993); Roelink, H., Augsburger, A., Heemskerk, J., Korzh, V., Norlin, S., Ruiz i Altaba, A., Tanabe, Y., Placzek, M., Edlund, T., Jessell, T. M. & Dodd, J. ,*Cell* 76, 761-775 (1994); Martí, E., Bumcrot, D. A., Takada, R. & McMahon, A. P., *Nature* 375, 322-325 (1995); Ruiz i Altaba, A., Roelink, H. & Jessell, T. M., *Mol. Cell. Neurosci.* 6, 106-121 (1995); Chiang, C., Litingtung, Y., Lee, E., Young, K. E., Corden, J. L., Westphal, H. & Beachy, P. A., *Nature* 383,407-413 (1996);Ericson, J., Morton, S., Kawakami, A., Roelink, H. & Jessell, T. M., *Cell* 87, 661-673 (1996)). Previous work by the applicants herein on the role of sonic hedgehog signaling during neural plate patterning in frog (*Xenopus laevis*) embryos demonstrated that cells becoming floor plate respond to Shh by expressing Gli 1, Pintallavis and HNF-3β, critical transcription factors that themselves can induce the differentiation of floor plate cells (Lee, J., Platt, K. A., Censullo, P. & Ruiz i Altaba, A. Gli1 is a target of sonic hedgehog that induces ventral neural tube development. *Development*, 124(13):2537-52 (1997); Ruiz i Altaba, A., Roelink, H. & Jessell, T. M. Restrictions to Floor Plate Induction by hedgehog and Winged Helix Genes in the Neural Tube of Frog Embryos. *Mol. Cell. Neurosci.* 6, 106-121 (1995); Ruiz i Altaba, A., Cox, C., Jessell, T. & Klar, A. Deregulated Expression of the Midline Transcription Factor Pintallavis Induces Ectopic Expression of a Floor Plate Marker. *Proc. Natl. Acad. Sci. USA* 90, 8268-8272 (1993); Ruiz i Altaba, A., Prezioso, V. R., Darnell, J. E. & Jessell, T. M. Sequential expression of HNF-3β and HNF-3 by embryonic organizing centers: the dorsal lip/node, notochord and floor plate. *Mech. Dev.* 44, 91-108 (1993)).

In addition to effects on neural tissue, it has been found that ectopic expression of Shh and Gli1 also leads to the activation of Shh signaling target genes in epidermal non-neural ectoderm. Injected Shh induced the ectopic expression of Gli1, HNF-3β and Shh (Ruiz i Altaba, A., Roelink, H. & Jessell, T. M., Mol.Cell. Neurosci. 6, 106-121 (1995)), and ectopic expression of Gli1 induced the ectopic expression of HNF-3β and Shh (Lee, J., Platt, K. A., Censullo, P. & Ruiz i Altaba, A. Gli1 is a target of sonic hedgehog that induces ventral neural tube development. Development (1997)). Together, these results indicated that both neural and epidermal cells have functional reception and transduction mechanisms for Shh and can respond by activating the expression of Shh/Gli1 target genes even though epidermal cells do not normally receive the Shh signal at this stage.

Furthermore, SHH signaling has been implicated in many aspects of animal development, acting through the transmembrane proteins PATCHED1 (PTCH1) and SMOH to activate the GLI zinc-finger transcription factors (Ingham, P. & McMahon, A., *Genes Dev.* 15, 3059-87 (2001); Ruiz i Altaba, A., Sanchez, P. & Dahmane, N., *Nat. Rev. Cancer* 2, 361-372 (2002).

Lung cancer is the leading cause of cancer deaths in both men and women in developed countries and is a growing problem in developing countries (Schottenfeld, 1996). The lack of biomarkers for early detection and ineffective chemotherapies are the main reasons why the prognosis of patients with lung cancer remains poor. Thus, new methods for early detection such as biomarkers, new approaches for lung cancer chemoprevention and new drugs based on rational targets need to be developed. Increased understanding of the molecular and cellular basis of the initiation events and mechanisms underlying drug resistance will be needed to achieve these goals.

Considering the adverse side-effects and expense associated with treating cancer, in particular, lung cancer, better diagnostic and prognostic tools are needed. Therefore, there is a need to identify other factors that can be used for the early detection of cancer, as well as the means to predict the progression of cancer, including but not limited to, lung cancer. In addition, there is a need to identify new therapeutic strategies for treating cancer, including, but not limited to, lung cancer.

While GLI1 has been implicated in a number of cancers, including basal cell carcinoma (Dahmane et al., 1997), and medulloblastoma (Goodrich et al., 1997), the role for GLI1 in human lung cancers remains unknown. Indeed, uncontrolled activity of this pathway is sufficient to induce medulloblastomas in mice (Goodrich et al., 1997) and ectopic expression of GLI1 in the embryonic frog epidermis or GLI1 and GLI2 in the mouse epidermis results in the development of basal-cell carcinoma-like and other skin tumors (Dahmane et al., 1997; Nilsson et al., 2000; Grachtchouk et al., 2000).

The present application is directed to the identification of the role of the gli genes and the GLI proteins in lung cancer and to methods and compositions for treating and/or diagnosing this disease.

The citation of any reference herein should not be construed as an admission that such reference is available as "Prior Art" to the instant application.

SUMMARY OF THE INVENTION

The human zinc finger transcription factors GLI1, GLI2 and GLI3 encode downstream effectors of the Sonic hedgehog pathway, which play critical roles during early development, organogenesis and in the adult, particularly in development of the nervous system. GLI1 has also been implicated in a number of cancers, including basal cell carcinoma, rhabdomyosarcoma, medulloblastoma, gliomas and small cell lung tumors. The studies presented herein provide further evidence for GLI1, GLI2 and GLI3 in tumorigenesis, particularly lung cancer. Since cancer may be a disease of stem cell lineages and SHH-GLI signaling controls the behavior of precursors and of cells with stem cell properties in the mammalian brain (Lai K, Kaspar B K, Gage F H & Schaffer D V, *Nat Neurosci* 6, 21-7 (2003); Machold R, et al., *Neuron* 39,937-50 (2003); Palma, V & Ruiz i Altaba, A., *Development*, 131: 337-345 (2004)), as well as in other organs and species (Zhang Y & Kalderon D., *Nature.* 410, 599-604 (2001); Park Y, et al., *Dev Biol.* 253, 247-57 (2003)), the inventors propose that many cancers, including those disclosed herein, in particular, lung cancer, derive from inappropriate expansion of stem cell lineages due to abnormal SHH-GLI function.

Accordingly, the present invention relates to the discovery that the SHH/GLI pathway has a deleterious effect on cells in terms of promotion of tumorigenesis and tumor cell growth, metastasis and/or tumor cell survival. More particularly, the present invention relates to the identification of the role that GLI plays in prevention or inhibition of apoptosis in tumor cells. In addition, the present invention also relates to the identification of the role that GLI may play in induction of resistance to chemotherapeutic agents useful for treating cancers. In a more particular embodiment, the present invention relates to the role of the GLI signaling pathway in lung tumors, and compositions and methods for treating a subject suffering from a lung tumor. More particularly, the invention provides for compositions and methods for treating such tumors with small molecule inhibitors of the SHH/GLI signaling pathway, including small synthetic organic molecules or siRNA nucleic acids.

The present invention describes novel strategies to prevent the tumorigenic effects of the SHH/GLI pathway. Accordingly, it is an object of the present invention to develop novel therapeutic strategies for treatment of cancers based on the inhibition of signalling by way of the SHH/GLI pathway. Furthermore, as shown by Applicants herein, the present invention provides a means of diagnosing aggressive forms of cancers, in particular, lung cancer, by measurement of GLI in tumor samples or other body tissues, cells or body fluids as a means of assessing the metastatic potential of various cancers, in particular, lung cancer, which could then aid in developing the most effective treatment regimen.

In accordance with the present invention, methods are disclosed for the diagnosis of cancers associated with increased expression, synthesis and/or activity of at least one GLI molecule. In one embodiment, the invention provides for therapies which are based, at least in part, on the observation that there is a relationship between the increased expression of the gli genes and the development, onset or presence of cancers, including, but not limited to, lung cancer.

Accordingly, the invention in an initial aspect extends to a method for the diagnosis and detection of lung cancer in mammals, including humans, which comprises measuring the presence and level of expression of at least one of the GLI proteins, including GLI1, GLI2 and/or GLI3 (SEQ ID NOs: 16, 18 and 20, respectively) or measurement of the genes encoding said proteins, including gli1, gli2 and/or gli3, (the nucleic acid sequences of SEQ ID NOs: 15, 17 and 19, respectively) or combinations thereof.

Still further, the invention includes the development of therapeutic agents that are capable of controlling the expression, synthesis and/or activity/function of GLI1, GLI2 and/or GLI3, and are thereby able to inhibit the development and/or treat cancers, including lung cancer in an animal subject, and particularly in humans. Such agents may include small molecules, ligands, antisense nucleic acids, siRNA molecules, antibodies and other agents that would function as GLI1, GLI2 and/or GLI3 antagonists/inhibitors or would otherwise interrupt GLI1, GLI2 and/or GLI3 expression and/or activity. Suitable pharmaceutical compositions could be administered by a variety of routes, including topical, oral, parenteral, intrathecal, intranasal, and the like, at a dosage level and schedule that may be determined by the clinician in accordance with the particular condition of the patient. Furthermore, therapies that promote a decrease of positive GLI function (GLI1, GLI2 AND GLI3), while also promoting an increase of negative repressor of GLI function (predominantly GLI3) are also contemplated by the present invention for the treatment of cancers and hyperproliferative conditions.

Accordingly, it is a principal object of the present invention to provide a method for the detection, diagnosis and treatment of cancer, particularly lung cancer and more particularly, small cell and non-small cell lung cancer, that is efficient and accurate.

It is a further object of the present invention to provide a method as aforesaid that involves the observation and measurement of the level of expression of the Gli1, Gli2 and/or Gli3 genes and/or their protein products GLI1, GLI2 and/or GLI3. In a particular embodiment, the level of expression would be assessed in tissues, cells or bodily samples taken from subjects suspected of having such cancers.

It is a still further object of the present invention to provide assays as aforesaid that may be used to screen for candidate inhibitors of cancers associated with increased expression or activity of GLI protiens, including GLI1, GLI2 and/or GLI3.

It is a yet further object of the present invention to provide therapeutic agents, compositions containing them, and corresponding methods of administration, that result from the identification and development of agents that act to modulate or control the activity or expression of GLI1, GLI2 and/or GLI3 in animals, and particularly humans.

Accordingly, a first aspect of the invention provides a method of inducing a tumor cell to undergo senescence, necrosis or apoptosis comprising administering an antagonist to the SHH/GLI signaling pathway in the cell, wherein said administering results in tumor cell death and prevention from metastasis. In a particular embodiment, the tumor cell is selected from the group consisting of brain tumors, e.g. gliomas, medulloblastomas, primitive neuroectodermal tumors (PNETS); skin tumors, e.g. basal cell carcinoma, lung tumors; tumors of the gastrointestinal tract; muscle tumors (rhabdomyosarcomas); soft tissue tumors (e.g. sarcomas), pancreatic tumors and prostate tumors. In a more particular embodiment, the tumor is a lung tumor such as e.g. lung adenocarcinomas, small cell lung cancers, large cell lung cancers.

In another particular embodiment, the antagonist may be selected from the group consisting of a small organic molecule inhibitor of the SHH/GLI signaling pathway. In one particular embodiment, the antagonist is an agent that inhibits the action of SMO (smoothened) in the receptor complex. Included in this embodiment are plant alkaloids, and analogs or homologs thereof, such as cyclopamine or jervine. In another particular embodiment, the inhibitor may be an antisense nucleic acid molecule or a small interfering RNA (siRNA) molecule. In one embodiment, the siRNA molecule comprises the nucleic acid sequence of SEQ ID NOs: 29, 31 and 32, wherein said nucleic acid inhibits the proliferation of tumor cells. In another particular embodiment, the antisense nucleic acid may be a DNA or an RNA molecule. In yet another particular embodiment, the RNA molecule is a single stranded RNA molecule, which is an antisense oligonucleotide, and which upon delivery in vivo or in vitro to a tumor cell, inhibits proliferation of the tumor cell. In yet another particular embodiment, the DNA molecule is an antisense oligonucleotide, which upon delivery in vivo or in vitro to a tumor cell, inhibits proliferation of the tumor cell. In another particular embodiment, the antisense molecule comprises the nucleotide sequence as set forth in SEQ ID NO: 33. Any of the above inhibitors/antagonists of the expression, synthesis or activity/function of GLI may inhibit at least one GLI molecule. They may inhibit a combination of GLI molecules. The inhibitor may antagonize the synthesis or function of either the GLI protein or the nucleic acid encoding the GLI protein.

In another particular embodiment, the inhibitor of the SHH/GLI signaling pathway may be an antibody molecule. The antibody may be an anti-GLI polyclonal or monoclonal antibody. The antibody may be a "chimeric antibody", which refers to a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816,397.). The antibody may be a human or a humanized antibody. The antibody may be a single chain antibody. (See, e.g., Curiel et al., U.S. Pat. No. 5,910,486 and U.S. Pat. No. 6,028,059). The antibody may be prepared in, but not limited to, mice, rats, rabbits, goats, sheep, swine, dogs, cats, or horses.

In a particular embodiment, the anti-GLI antibody is a blocking antibody and is effective as a therapeutic agent to prevent the proliferation of tumor cells in vivo. In another particular embodiment, the antibody is prepared as a pharmaceutical composition with a pharmaceutically acceptable carrier. In yet another particular embodiment, the antibody is coupled to an anti-tumor drug or radioisotope for use in treating aggressive and highly invasive tumor cells in situ. In yet another particular embodiment, the antibody is effective as a diagnostic agent to aid in identification of aggressive and highly invasive tumor cells in situ or in vivo. Accordingly, the antibody is coupled to an imaging reagent and used for in situ or in vivo imaging of aggressive and highly invasive tumor cells in situ or in vivo.

A second aspect of the invention provides a method of screening for necrotic, senescent or apoptotic resistant tumor cells, comprising measuring the level of expression of at least one GLI protein or nucleic acid encoding the GLI protein in said tumor cells, wherein enhanced expression of said GLI protein or the nucleic acid encoding the GLI protein correlates with apoptosis resistance in said tumor cells. In a particular embodiment, the screening may be done by immunological methods, such as western blotting techniques, immunofluorescence or radioimmunoassays using an antibody specific for GLI. Alternatively, standard molecular biological approaches may be used, including PCR techniques using primers or probes specific for GLI. In another embodiment, apoptosis is measured using standard procedures in the art for assessing apoptosis (or lack thereof), including, but not limited to, measurement of membrane blebbing, chromatin condensation, formation of apoptotic bodies, TUNEL assay and other procedures known to one skilled in the art. Based on the results, a correlation may be made between the presence/expression of at least one GLI protein or nucleic acid and resistance to apoptosis.

A third aspect of the invention provides a method of predicting resistance of a tumor cell to chemotherapeutic agents comprising measuring the level of expression of at least one GLI protein or nucleic acid encoding the at least one GLI protein in said tumor cell, whereby an increased level of expression of GLI in said tumor cell is predictive of resistance of said tumor cell to chemotherapeutic agents. Standard immunological or molecular biological techniques may be used to predict resistance of a tumor cell to chemotherapeutic agents. The GLI proteins may be selected from GLI1, GLI2 or GLI3.

A fourth aspect of the invention provides a method of treating senescent, necrotic or apoptotic resistant tumor cells in vitro or in vivo comprising administering an antagonist of the GLI signaling pathway to said tumor cell. In a particular embodiment, the antagonist comprises agents that increase negative, or decrease positive acting elements affecting GLI signaling, said agents selected from the group consisting of small molecules that alter PKA kinase activity, small molecules that alter GSK3 kinase activity, small molecules that alter CK1 kinase activity, small molecules or siRNAs/antisense RNAs that alter DYRK1 kinase activity and any factor that interacts with or affects the expression and/or function of GLI. In another particular embodiment, the antagonist may be selected from the group consisting of a small molecule inhibitor of the GLI signaling pathway, such as, but not limited to, agents that inhibit the action of SMO (Smoothened) in the receptor complex, such as the plant alkaloids cyclopamine and jervine, and analogs, or derivatives thereof. In another particular embodiment, the antagonist may be seleceted from an antisense nucleic acid molecule or a siRNA molecule. In yet another particular embodiment, the antisense molecule may be a DNA or an RNA oligonucleotide. In another particular embodiment, the siRNA molecule comprises the nucleic acid molecule of any one of SEQ ID NOs: 29, 31 or 32, or combinations thereof. In another particular embodiment, the antagonist is an antisense molecule comprising the nucleic acid sequence as set forth in SEQ ID NO: 33. The treating of the apoptotic resistant tumor cells by the agents described herein results in making the apoptotic resistant tumor cells, apoptotic sensitive, thus allowing death of the tumor cell and prevention of metastasis.

A fifth aspect of the invention provides a method of overcoming resistance to chemotherapeutic agents in tumor cells, comprising administering an antagonist to the SHH/GLI signaling pathway to the cell, wherein said administering results in increased sensitivity of the tumor cell to said chemotherapeutic agent and results in subsequent tumor cell death and prevention from metastasis. In a particular embodiment, the antagonist comprises agents that increase negative, or decrease positive acting elements affecting GLI signaling, said agents selected from the group consisting of small molecules that alter PKA kinase activity, small molecules that alter GSK3 kinase activity and small molecules that alter CK1 kinase activity. In another particular embodiment, the antagonist may be selected from the group consisting of a small molecule inhibitor of the GLI signaling pathway, such as, but not limited to agents that inhibit the action of SMO (smoothened) in the receptor complex, such as the plant alkaloids, cyclopamine or jervine. In another particular embodiment, the antagonist may be selected from an antisense nucleic acid molecule or an siRNA molecule. In another particular embodiment, the siRNA molecule comprises the nucleic acid molecule of any one of SEQ ID NOs: 29, 31 or 32, or combinations thereof. The tumors that may be treated with such agents may be selected from the group consisting of gliomas, medulloblastomas, primitive neuroectodermal tumors (PNETS), basal cell carcinoma, small cell lung cancers, large cell lung cancers, tumors of the gastrointestinal tract, rhabdomyosarcomas, soft tissue sarcomas, pancreatic tumors and prostate tumors.

A sixth aspect of the invention provides for a method of treating a subject suffering from a cancerous or hyperproliferative/hyperplastic condition, wherein said condition is characterized by the presence of a senescent, necrotic or apoptotic resistant tumor, comprising administering an antagonist of the SHH/GLI signaling pathway. In a particular embodiment, the administering results in induction of apoptosis in said tumor, in increased sensitivity to chemotherapeutic agents, and in prevention of metastasis of said tumor. In another particular embodiment, the antagonist comprises agents that increase negative, or decrease positive acting elements affecting GLI signaling, said agents selected from the group consisting of small molecules that alter PKA kinase activity, small molecules that alter GSK3 kinase activity, small molecules that alter CK1 kinase activity, small molecules that alter DYRKI kinase activity and any factor that affects GLI expression and/or function. In another particular embodiment, the antagonist may be selected from the group consisting of a small molecule inhibitor of the GLI signaling pathway, such as, but not limited to, agents that inhibit the action of SMO (Smoothened) in the receptor complex, such as cyclopamine or jervine or analogs or derivatives thereof. In another particular embodiment, the antagonist may be selected from an antibody to a GLI molecule, a siRNA molecule specific for GLI1, GLI2 and/or GLI3, an antisense nucleic acid specific for GLI1, GLI2 and/or GLI3, or any agent that inhibits the SHH/GLI signaling pathway. In yet another preferred embodiment, the invention provides for a method of treating tumors or hyperplasia comprising administering an agent that blocks endogenous GLI signaling, wherein said agent is a small interfering RNA (siRNA) molecule comprising a nucleic acid sequence obtained from the nucleotides that encode GLI1, GLI2 and/or GLI3 or fragments thereof. In another particular embodiment, the siRNA molecules may be selected from the nucleotide sequences consisting of those set forth in SEQ ID NOs: 29, 31, 32 and combinations thereof. In yet another particular embodiment, the antagonist may comprise an antisense molecule having the nucleotide sequence as set forth in SEQ ID NO: 33. In yet another particular embodiment, the tumor is selected from the group consisting of gliomas, medulloblastomas, primitive neuroectodermal tumors (PNETS), basal cell carcinoma, small cell lung cancers, large cell lung cancers, tumors of the gastrointestinal tract, rhabdomyosarcomas, soft tissue sarcomas, pancreatic tumors, and prostate tumors. In yet another particular embodiment, the invention provides for a method of treating tumors comprising administering a blocking antibody that binds to or reacts with GLI1, GLI2 and/or GLI3. The antibodies may be polyclonal or monoclonal. They may be single chain antibodies. They may be chimeric antibodies. They may be Fab fragments or soluble components thereof. They may be human or humanized. They may be produced in other animals, including but not limited to horses, goats, sheep, mice, rats, rabbits and guinea pigs. Such antibodies may be internalized and may inactivate intracellular GLI proteins and/or retain them in the cytoplasm thus rendering them inactive. Anti-GLI agents may also be used as adjunct therapy with other standard forms of therapy for cancer and hyperproliferative conditions. That is, the agents of the present invention that inhibit signaling through the SHH/GLI pathway may be useful in increasing the effectiveness of other chemotherapeutic agents. Accordingly, the agents of the present invention may be used alone or in combination with other agents useful for treating the conditions described herein. The administration of the anti-GLI agents may be administered before the other anti-cancer agent, or it may be administered concurrently or after the other anti-cancer agent.

A seventh aspect of the invention provides diagnostic and prognostic methods that allow aggressive forms of cancer to be identified. In a particular embodiment, the methods of identifying aggressive forms of cancer encompass measurement of GLI levels in a bodily sample. In one preferred embodiment, an aggressive form of lung cancer is identified. In another particular embodiment, the lung cancer to be identified includes small cell and non small cell lung cancer. In another particular embodiment, the cancer to be identified may be selected from the group consisting of basal cell carcinoma, melanoma, glioblastoma, medulloblastoma, PNETs, other brian tumors, stomach, GI tract including colon, pancreas, rhabdomyosarcomas, and soft tissue sarcomas.

In yet another particular embodiment, antibodies specific for GLI, and variants thereof, can be used in a diagnostic test to detect the presence of GLI in body fluids, cells or in tissue biopsy. In specific embodiments, measurement of the gli1, gli2 and/or gli3 gene or gene products (such as GLI proteins) and variants thereof can be used to assess the potential aggressiveness of a particular tumor and aid in determination of metastatic potential, thus enabling a more effective treatment strategy.

An eighth aspect of the invention provides methods of identifying a subject that is likely to have an aggressive and highly invasive form of cancer. In a particular embodiment, the method comprises determining the level of GLI (GLI1, GLI2, OR GLI3) in a tissue specimen from the subject; wherein when the level of GLI determined is significantly elevated in tumor cells relative to that determined in benign cells of the same specimen, the animal subject is identified as being likely to have an aggressive form of cancer. In another embodiment, the method comprises determining the level of GLI in a specimen of bodily fluid from the subject; wherein when the level of GLI determined is significantly elevated in said bodily fluid relative to that determined in bodily fluid obtained from a normal control subject, the animal subject is identified as being likely to have an aggressive form of cancer. Alternatively, a range of values may be established for the level of GLI1, 2 or 3 in a normal population of individuals who are free of cancer, and the level of GLI1, GLI2, or GLI3 obtained from a subject suspected of having cancer may be compared to this normal range.

Preferably the subject is a human subject that is likely to have an aggressive form of cancer, in particular, lung cancer. One such method comprises determining the level of GLI1, GLI2 and/or GLI3 in a lung sample from the animal subject.

In one embodiment, the sample is obtained by biopsy. In another embodiment, the sample is obtained by needle biopsy.

In yet another embodiment, when there is a significant increase in GLI, particularly GLI1, but not excluding GLI2 or GLI3 in the tumor tissue or in tumor cells obtained from the subject relative to that determined in benign cells of the same specimen, the subject is identified as being likely to have a fast growing or aggressive form of cancer. In one embodiment, the determination of the level of GLI is performed in situ. In another embodiment the determination of the level of GLI is performed in vitro. In still another embodiment, the determination of the level of GLI is performed in vivo. In a yet further embodiment, the determination of the level of GLI is performed with an antibody specific for GLI. In a yet further embodiment, the level of GLI is determined using an antibody specific for GLI for Western blot analysis. In another such embodiment the determination of the level of GLI is performed by PCR, including real-time PCR, with a primer specific for an mRNA encoding GLI. In still another embodiment the determination of the level of GLI is performed with a nucleotide probe specific for an mRNA encoding GLI. In one such embodiment, the determination of the level of GLI is performed by a Northern blot. In another embodiment, the determination of the level of GLI is performed by a ribonuclease protection assay. In yet another embodiment, the level of GLI is determined using standard immunoassay procedures, such as enzyme linked immunoassay (ELISA) or radioimmunoassay (RIA).

When the level of GLI is low to undetectable in the sample, the likelihood of the patient having an invasive or aggressive form of the cancer is low. The level of GLI is said to be normal when the level is within 20% of that observed in the normal population. A GLI level of between 30 to <60% of that found in the normal population is considered high, and a level >60% as compared to the normal population is considered very high.

A ninth aspect of the invention provides methods for identifying an animal subject that is likely to have a slow growing form of cancer. In one embodiment, the method comprises detecting low GLI levels in a tumor obtained from a sample from the subject; wherein when the GLI is barely detectable in the tumor sample from the subject, and is comparable to the levels detected in the benign cells of the same specimen, the subject is identified as being likely to have a slow growing and non-invasive cancer. In another embodiment, the method further comprises determining the level of GLI in a tissue sample from the animal subject; wherein when the level of GLI determined is up-regulated by not greater than 50% in tumor cells relative to that determined in benign cells of the same specimen, the animal subject is identified as being likely to have a slow growing cancer. In a particular embodiment, the cancer is selected from the group consisting of brain cancer, prostate cancer, and lung cancer. In a more particular embodiment, the cancer is a small cell or a non-small cell lung cancer.

In another embodiment, the method comprises detecting low GLI levels in a sample of bodily fluid obtained from the subject; wherein when the GLI is barely detectable in the sample of bodily fluid from the subject and is comparable to the levels detected in a sample obtained from a normal subject known to be free of lung cancer, the subject is identified as being likely to have a slow growing and non-invasive lung cancer. The sample of bodily fluid may be selected from the group consisting of whole blood, serum, plasma, urine and cerebrospinal fluid In another embodiment, the method of determining the levels of GLI may be performed in situ or in vitro. The method of determining may be performed by a method that uses a probe selected from the group consisting of an antibody specific for GLI; a set of primers specific for an mRNA encoding GLI; and a nucleotide probe specific for an mRNA encoding GLI.

A tenth aspect of the invention provides for detection of GLI in tissue samples suspected of being cancerous, or in metastatic cells present in bodily fluids from a subject as a means of assessing the level of aggressiveness or invasiveness of a tumor. If GLI is present in very low levels in a tissue sample from the subject, or if it is not detectable at all, using the procedures outlined below which are known to one skilled in the art, then the tumor is believed to be non-aggressive or invasive. If GLI is present in high levels compared to the level observed in normal or benign tissue samples, or in bodily samples obtained from individuals who do not have an aggressive or invasive tumor, then the cancer is believed to be aggressive or invasive, with a greater likelihood of metastasis. GLI, if present in low amounts, can be detected by PCR, Western blot and/or Northern blot and/or as provided for below. When GLI is detectable at low levels, or is not measurable at all in the tissue sample from the animal subject, the animal subject is identified as being likely to have a slow growing cancer. In one embodiment, the sample is obtained by biopsy. In a particular embodiment the level of GLI detected is about 50% or less compared to the level observed in aggressively growing cancers. In yet another embodiment, the level of GLI is determined in a bodily sample selected from whole blood, plasma or serum, urine and cerebrospinal fluid.

In one embodiment the determination of the level of GLI is performed in situ. In another embodiment the determination of the level of GLI is performed in vitro. In still another embodiment, the determination of the level of GLI is performed in vivo. In a particular embodiment the determination of the level of GLI is performed with an antibody specific for GLI. In another such embodiment the determination of the level of GLI is performed by PCR with a primer specific for an mRNA encoding GLI. In still another embodiment the determination of the level of GLI is performed with a nucleotide probe specific for an mRNA encoding GLI. In still another embodiment the determination of the level of GLI is performed by a Northern blot. In yet another embodiment the determination of the level of GLI is performed by a ribonuclease protection assay. In still another embodiment the determination of the level of GLI is performed by immunohistochemistry. In still another embodiment the determination of the level of GLI is performed by RT-PCR.

In an eleventh aspect of the invention, GLI can be used as a surrogate biomarker for lung cancer as well as other cancers which utilize the GLI pathway for cell signaling, and in which GLI1, GLI2 and/or GLI3 is present. In one embodiment, the presence of increasing levels of GLI1, GLI2 and/or GLI3, compared to that found in normal, non-cancerous tissue, is indicative of an increased risk for cancer metastasis. Such metastasis may be to the bone or to any other tissue in the body.

A twelfth aspect of the invention provides an isolated double stranded siRNA for inhibiting expression of a gli gene. In one embodiment, the siRNA comprises a first nucleotide sequence that hybridizes under stringent conditions to a nucleotide sequence of a gli gene and/or its mRNA and a second nucleotide sequence that is complementary to said first nucleotide sequence. In a particular embodiment, the siRNA is about 10-50 nucleotides long. In another particular embodiment, the siRNA is about 10-50 nucleotides long. In another particular embodiment, the siRNA is about 10-30 nucleotides long. In yet another particular embodiment, the siRNA is about 17-25 nucleotides long. In a another particular embodiment, the siRNA is selected from the group consisting of the nucleic acid sequences as set forth in SEQ ID NO: 29, SEQ ID NO: 31 and SEQ ID NO: 32. In yet another particular embodiment, the siRNA, upon delivery to a cell containing the gli gene for which said siRNA molecules are specific, inhibits the proliferation of said cell. In yet another particular embodiment, the double stranded siRNA is a short hairpin RNA (shRNA) comprising a first nucleotide sequence that hybridizes under stringent conditions to a nucleotide sequence of a gli gene, and a second nucleotide sequence which is a complementary inverted repeat of said first nucleotide sequence and hybridizes to said first nucleotide sequence to form a hairpin structure. In another particular embodiment, the shRNA may have a foreign hairpin from another gene and the stem of the hairpin is formed by the gli sequences. In another particular embodiment, the isolated siRNA molecule may be selected from the group consisting of SEQ ID NOs: 29, 31 and 32, wherein said siRNA molecule inhibits the proliferation of tumor cells. In yet another particular embodiment, the tumor cells are characterized in part by the presence of at least one of the GLI proteins or genes encoding at least one of the GLI proteins.

A thirteenth aspect of the invention provides an antibody specific for GLI. In a particular embodiment, the GLI may be GLI1, GLI2 or GLI3. In another particular embodiment, the antibody is a polyclonal or monoclonal antibody. In another embodiment, the antibody is a human or humanized antibody or fragment thereof. In yet another embodiment, the antibodies may be single chain antibodies. They may be chimeric antibodies. They may be Fab fragments or soluble components thereof. They may be produced in other animals, including but not limited to horses, goats, sheep, mice, rats, rabbits and guinea pigs.

A fourteenth aspect of the invention provides pharmaceutical compositions for the treatment of tumors or hyperplastic conditions, comprising agents that block endogenous GLI signaling and a pharmaceutically acceptable carrier. In a particular embodiment, the agent is a small interfering RNA molecule comprising nucleic acid sequences derived from nucleotides that encode GLI1, GLI2 and/or GLI3, or fragments thereof. In a particular embodiment, the agent comprises a siRNA molecule comprising the nucleotide sequence as set forth in SEQ ID NOs: 29, 31, 32, or combinations thereof. In another particular embodiment, the agent is an antisense nucleic acid molecule comprising the nucleotide sequence as set forth in SEQ ID NO: 33. In another particular embodiment, the agent is a small organic molecule that blocks the GLI signaling pathway. In another particular embodiment, the small organic molecule is cyclopamine, or an analog or a derivative thereof, and a pharmaceutically acceptable carrier. In yet another particular embodiment, the agent is an antibody that blocks GLI signaling, and a pharmaceutically acceptable carrier.

A fifteenth aspect of the invention provides an isolated nucleic acid probe specific for Gli1, Gli2 or Gli3. In a particular embodiment, the probe is used to identify GLI1, GLI2 and/or GLI3 in a tumor sample or a sample from a hyperplastic condition. In another particular embodiment, the probe can differentiate between highly invasive and aggressive tumors and benign tumors in a patient sample. In another particular embodiment, the GLI1, GLI2 and/or GLI3 is mammalian GLI1, GLI2 and/or GLI3. In yet another particular embodiment, the mammalian GLI1, GLI2 or GLI3 is human GLI1, GLI2 OR GLI3.

A sixteenth aspect of the invention provides methods for treating and/or preventing a hyperproliferative disease, disorder or condition, and/or prevention of tumor cell metastasis in a mammal, comprising administering an inhibitor or antagonist of the GLI pathway in a cell to said mammal. In one such embodiment, the method comprises transplanting a cell containing an inhibitor of GLI1, GLI2 and/or GLI3 into the mammal suffering from a cancerous or hyperproliferative condition. In an alternative embodiment, the method comprises transplanting an expression vector that encodes an inhibitor or antagonist of Gli1, Gli2 and/or Gli3 or an active fragment thereof into the mammal having the hyperproliferative disease. In yet another embodiment, the inhibitor or fragment thereof is inserted into the mammal. In yet another embodiment, pharmaceutical compositions containing the inhibitor or antagonist of the expression and/or function of GLI1, GLI2 and/or GLI3 proteins or active fragments thereof or small organic molecules that decrease expression and/or function/activity of Gli1, Gli2 and/or Gli3 are envisioned for treatment and/or prevention of hyperproliferative diseases, disorders or conditions or for inhibition of tumor cell metastasis. Methods of delivery of such pharmaceutical compositions includes oral, sublingual, buccal, intravenous, intramuscular, subcutaneous, intrathecal, intracranial or intraventricular delivery. Such pharmaceutical compositions would contain appropriate carriers to enhance delivery to the site of injury. In a preferred embodiment the mammal is a human.

Other aspects and advantages will become apparent from a review of the ensuing detailed description taken in conjunction with the following illustrative drawings.

DETAILED DESCRIPTION OF THE INVENTION

Figure 1:
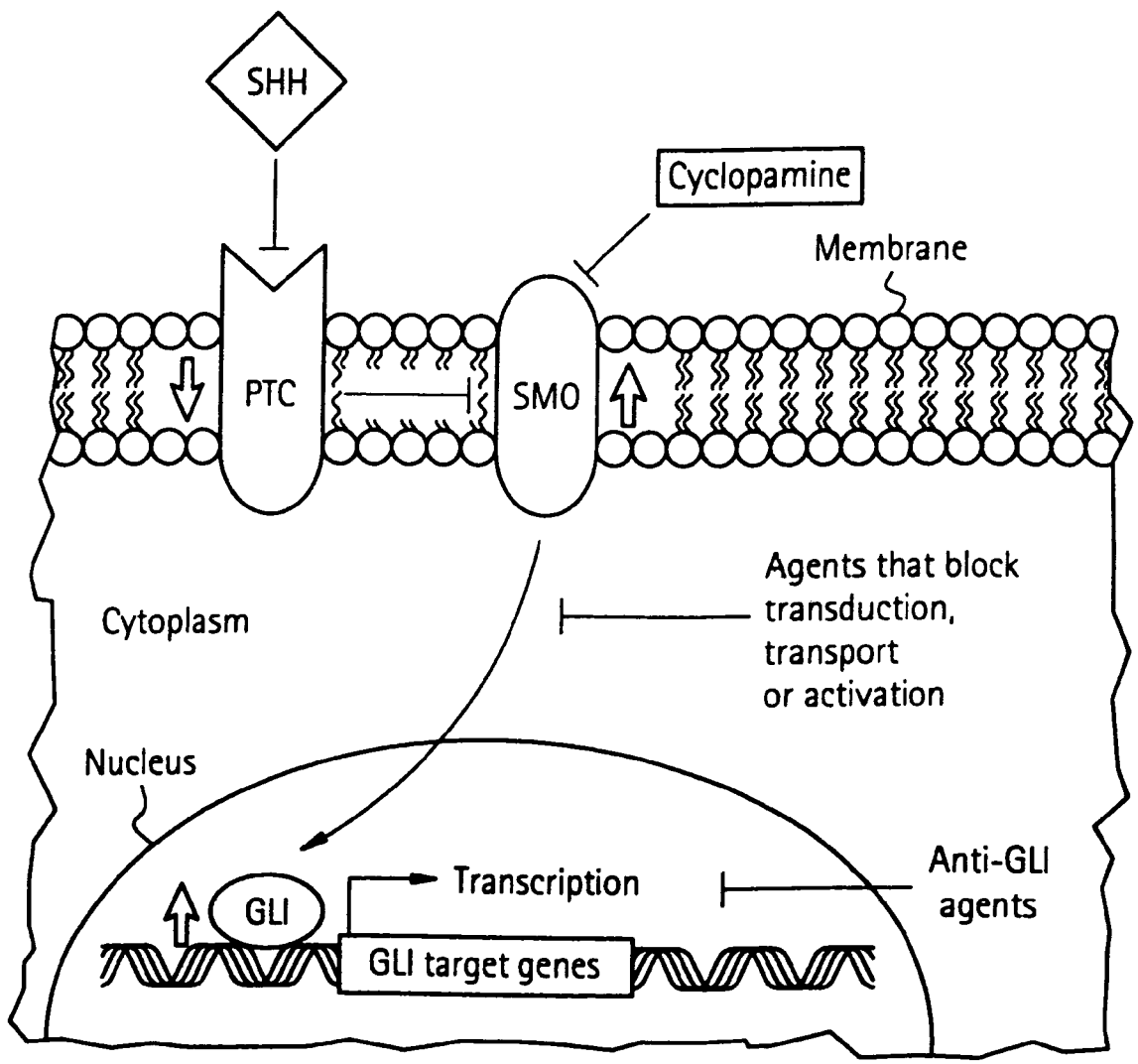
FIG. 1 SSH-GLI pathway and potential sites for therapeutic agents blocking its activity FIG. 2 Demonstration that GLI genes are consistently expressed in primary brain tumors FIG. 3 Demonstration that Cyclopamine, a drug that inhibits the response to Shh signaling modulates the proliferation of a subset of brain tumor cell lines FIG. 4 Effect of cyclopamine in a long-term treatment of a glioblastoma cell line (U87) in vitro. Shh-Gli pathway controls proliferation and viability of brain tumor cells FIG. 5 Cyclopamine modulates the proliferation of primary cortical gliomas that were dissociated and cultured in vitro FIG. 6 Demonstration that only a subset of cells from primary brain tumors, dissociated and cultured in vitro, have stem-like properties, and their proliferation is inhibited by the presence of cyclopamine FIG. 7 In vivo cyclopamine treatment reduces the size of medulloblastomas of Ptch+/−, p53−/−mice FIG. 8 Percentage of BrdU incorporation in the presence or absence of 5 uM cyclopamine FIG. 9 siRNAs for Gli1 and Gli2 block Shh responses in 10T1/2 cells FIG. 10 Downregulation of Gli1 and Gli2 inhibits U87 glioma cell proliferation FIG. 11 Proliferation of primary brain tumor cells is inhibited by blocking Gli1 and Gli2

Before the present methods and treatment methodology are described, it is to be understood that this invention is not limited to particular methods, and experimental conditions described, as such methods and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated by reference in their entireties.

Definitions

As noted above, the terms used herein have the meanings recognized and known to those of skill in the art. However, for convenience and completeness, particular terms and their meanings are set forth below.

As used herein the "SHH/GLI pathway" or "HH/GLI pathway" or "GLI-pathway" or "GLI signaling pathway" is used interchangeably with the "Sonic hedgehog (SHH) signaling pathway" and is the signaling pathway initiated by a hedgehog protein binding to its receptor(s) leading to the expression and/or function of a GLI protein. "GLI" as used herein refers to any one of the GLI1, GLI2 or GLI3 proteins. "gli" refers to the gene encoding the GLI proteins, and gli1, gli2 and gli3 are the genes encoding the GLI1, GLI2 and GLI3 proteins. Factors involved and/or can function in the SHH-GLI pathway include any hedgehog protein such as sonic hedgehog, Indian hedgehog, and desert hedgehog, patched 1 and 2, smoothened, agonists and antagonists of such proteins, PKA, fused, suppressor of fused, costal-2, and modifiers and/or partners of any of the GLI1, 2, or 3 proteins e.g., the Zic gene products.

As used herein the term "hedgehog" is used interchangeably with the term "HH" and is a cytokine that binds to the HH receptor to stimulate the beginning of the SHH-GLI pathway. The human SHH protein is encoded by the nucleotide sequence of SEQ ID NO:1 and has the amino acid sequence of SEQ ID NO:2. The murine SHH protein is encoded by the nucleotide sequence of SEQ ID NO:3 and has the amino acid sequence of SEQ ID NO:4. The rat SHH protein is encoded by the nucleotide sequence of SEQ ID NO:5 and has the amino acid sequence of SEQ ID NO:6. *Xenopus* HH protein is encoded by the nucleotide sequence of SEQ ID NO:7 and has the amino acid sequence of SEQ ID NO:8. The human Indian hedgehog (IHH) protein is encoded by the nucleotide sequences of SEQ ID NO:9 and/or 11 and has the amino acid sequence of SEQ ID NO:10 and/or 12. The murine desert hedgehog (DHH) protein is encoded by the nucleotide sequence of SEQ ID NO: 13 and has the amino acid sequence of SEQ ID NO: 14. Hedgehog proteins from species as different as humans and insects appear to play this same role and can be used interchangeably (see e.g., Pathi et al., (2001) Mech Dev. 106:107-117).

As used herein an "active fragment" of a hedgehog is a fragment of a hedgehog protein that can comprises the first 174 amino acids of the protein (not counting the signal sequence) and can stimulate both the in vitro proliferation and in vitro differentiation of a mouse subventricular stem cell such that the number of neuronal cells obtained in the presence of 100 µM or less active fragment of the HH is at least 2-fold greater than that obtained in its absence.

As used herein a "small organic molecule" or "small synthetic organic compound" is an organic compound (or organic compound complexed with an inorganic compound (e.g., metal)) that has a molecular weight of less than 3 kilodaltons, and preferably less than 1.5 kilodaltons.

As used herein a "reporter" gene is used interchangeably with the term "marker gene" and is a nucleic acid that is readily detectable and/or encodes a gene product that is readily detectable such as green fluorescent protein (as described in U.S. Pat. No. 5,625,048 issued Apr. 29, 1997, and WO 97/26333, published Jul. 24, 1997, the disclosures of each are hereby incorporated by reference herein in their entireties) or luciferase.

A "vector" is a replicon, such as plasmid, phage, virus, or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

As used herein, the term "homologue" is used interchangeably with the term "ortholog" and refers to the relationship between proteins that have a common evolutionary origin and differ because they originate from different species. For example, mouse SHH is a homologue of human SHH.

As used herein the term "heterologous nucleotide sequence" is a nucleotide sequence that is added to a nucleotide sequence of the present invention by recombinant molecular biological methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by a nucleotide sequence of the present invention after the recombinant nucleic acid is expressed. In still another embodiment the heterologous nucleotide can function as a means of detecting a nucleotide sequence of the present invention. A heterologous nucleotide sequence can comprise non-coding sequences including restriction sites, regulatory sites, promoters and the like. Thus, the nucleic acids that encode the proteins being used and/or detected in the present invention can comprise a heterologous nucleotide sequence.

As used herein the terms "fusion protein" and "fusion peptide" are used interchangeably and encompass "chimeric proteins and/or chimeric peptides" and fusion "intein proteins/peptides". A fusion protein of the present invention can comprise at least a portion of a HH protein of the present invention, for example, joined via a peptide bond to at least a portion of another protein or peptide including a second HH protein in a chimeric fusion protein.

As used herein a polypeptide or peptide "consisting essentially of" or that "consists essentially of" a specified amino acid sequence is a polypeptide or peptide that retains the general characteristics, e.g., activity of the polypeptide or peptide having the specified amino acid sequence and is otherwise identical to that protein in amino acid sequence except it consists of plus or minus 10% or fewer, preferably plus or minus 5% or fewer, and more preferably plus or minus 2.5% or fewer amino acid residues.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host, i.e., a symptom of Parkinson's disease.

In a specific embodiment, the term "about" means within 20%, preferably within 10%, and more preferably within 5%.

RNA interference (RNAi) is an evolutionarily conserved mechanism in plant and animal cells that directs the degradation of messenger RNAs homologous to short double-stranded RNAs termed "small interfering RNA (siRNA)". The ability of siRNA to direct gene silencing in mammalian cells has raised the possibility that siRNA might be used to investigate gene function in a high throughput fashion or to modulate gene expression in human diseases. Methods of preparing siRNAs are known to those skilled in the art. The following references are incorporated herein by reference in their entirety: Reich et al., *Mol Vis.* 9:210-6 (2003); Gonzalez-Alegre P et al., *Ann Neurol.* 53:781-7 (2003); Miller et al., *Proc Natl Acad Sci USA.* (2003); Bidere et al., *J Biol Chem.*, published as manuscript M301911200 (Jun. 2, 2003); Van De Wetering et al., EMBO Rep. 4:609-15 (2003); Miller and Grollman, *DNA Repair (Amst)* 2:759-63 (2003); Kawakami et al., *Nat Cell Biol.* 5:513-9 (2003); Abdelrahim et al., *Mol Pharmacol.* 63:1373-81 (2003); Williams et al., *J Immunol.* 170:5354-8 (2003); Daude et al., *J Cell Sci.* 116:2775-9 (2003); Jackson et al., *Nat Biotechnol.* 21:635-7 (2003); Dillin, *Proc Natl Acad Sci USA.* 100:6289-91 (2003); Matta et al., *Cancer Biol Ther.* 2:206-10 (2003); Wohlbold et al., Blood. (2003); Julien and Herr, *EMBO J.* 22:2360-9 (2003); Scherr et al., *Cell Cycle.* 2:251-7 (2003); Giri et al., *J Immunol.* 170:5281-94 (2003); Liu and Erikson, *Proc Natl Acad Sci USA.* 100:5789-94 (2003); Chi et al., *Proc Natl Acad Sci U S A.* 100:6343-6 (2003); Hall and Alexander, *J Virol.* 77:6066-9 (2003).

"Agent" refers to all materials that may be used to prepare pharmaceutical and diagnostic compositions, or that may be compounds, nucleic acids, polypeptides, fragments, isoforms, variants, or other materials that may be used independently for such purposes, all in accordance with the present invention.

"Analog" as used herein, refers to a a small organic compound, a nucleotide, a protein, or a polypeptide that possesses similar or identical activity or function(s) as the compound, nucleotide, protein or polypeptide or compound having the desired activity and therapeutic effect of the present invention. (eg. inhibition of tumor growth), but need not necessarily comprise a sequence or structure that is similar or identical to the sequence or structure of the preferred embodiment As used herein, a nucleic acid or nucleotide sequence, or an amino acid sequence of a protein or polypeptide is "similar" to that of a nucleic acid, nucleotide or protein or polypeptide having the desired activity if it satisfies at least one of the following criteria: (a) the nucleic acid, nucleotide, protein or polypeptide has a sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleic acid, nucleotide, protein or polypeptide sequences having the desired activity as described herein (b) the polypeptide is encoded by a nucleotide sequence that hybridizes under stringent conditions to a nucleotide sequence encoding at least 5 amino acid residues (more preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues) of the AAPI; or (c) the polypeptide is encoded by a nucleotide sequence that is at least 30% (more preferably, at least 35%, at least 40%, at least 45%, at least 50%, at least 55%, at least 60%, at least 65%, at least 70%, at least 75%, at least 80%, at least 85%, at least 90%, at least 95% or at least 99%) identical to the nucleotide sequence encoding the polypeptides of the present invention having the desired therapeutic effect. As used herein, a polypeptide with "similar structure" to that of the preferred embodiments of the invention refers to a polypeptide that has a similar secondary, tertiary or quarternary structure as that of the preferred embodiment. The structure of a polypeptide can determined by methods known to those skilled in the art, including but not limited to, X-ray crystallography, nuclear magnetic resonance, and crystallographic electron microscopy.

The term "antibody" as used herein includes intact molecules as well as fragments thereof, such as Fab and $F(ab')_2$, which are capable of binding the epitopic determinant. Antibodies that bind the genes or gene products of the present invention can be prepared using intact polynucleotides or polypeptides or fragments containing small peptides of interest as the immunizing antigen attached to a carrier molecule. Commonly used carriers that are chemically coupled to peptides include bovine serum albumin and thyroglobulin. The coupled peptide is then used to immunize the animal (e.g, a mouse, rat or rabbit). The antibody may be a "chimeric antibody", which refers to a molecule in which different portions are derived from different animal species, such as those having a human immunoglobulin constant region and a variable region derived from a murine mAb. (See, e.g., Cabilly et al., U.S. Pat. No. 4,816,567; and Boss et al., U.S. Pat. No. 4,816, 397.). The antibody may be a single chain antibody. The antibody may be a human or a humanized antibody. The antibody may be prepared in mice, rats, goats, sheep, swine, dogs, cats, or horses. A "blocking antibody" refers to an antibody that interferes with the function, activity or expression of a particular molecule, in the matter of the present invention, an antibody to SHH or GLI.

"Apoptosis" refers to "programmed cell death" and is characterized by certain cellular characteristics such as membrane blebbing, chromatin condensation and fragmentation, formation of apoptotic bodies and TUNEL (terminal deoxynucleotidyl transferase-mediated dUTP nick end-labeling) staining. Degradation of genomic DNA during apoptosis results in formation of characteristic, nucleosome sized DNA fragments; this degradation produces a diagnostic (about) 180 bp laddering pattern when analyzed by gel electrophoresis. A later step in the apoptotic process is degradation of the plasma membrane, rendering apoptotic cells leaky to various dyes (e.g., trypan blue and propidium iodide).

"Surrogate biomarker" or "biomarker" as used herein, refers to a highly specific molecule, the existence and levels of which are causally connected to a complex biological process, and reliably captures the state of said process. Furthermore, a surrogate biomarker, to be of practical importance, must be present in samples that can be obtained from individuals without endangering their physical integrity or well-being, preferentially from biological fluids such as blood, urine, saliva or tears and cerebrospinal fluid.

"Derivative" refers to either a compound, a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein or polypeptide possesses a similar or identical function as the parent polypeptide. "Derivative" also refers to chemically synthesized organic molecules that are functionally equivalent to the active parent compound, but may be structurally different. It may also refer to chemically similar compounds which have been chemically altered to increase bioavailability, absorption, or to decrease toxicity.

"Fragment" refers to either a protein or polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a parent protein or polypeptide, or a nucleic acid comprising a nucleotide sequence of at least 10 base pairs (preferably at least 20 base pairs, at least 30 base pairs, at least 40 base pairs, at least 50 base pairs, at least 50 base pairs, at least 100 base pairs, at least 200 base pairs) of the nucleotide sequence of the parent nucleic acid. Any given fragment may or may not possess a functional activity of the parent nucleic acid or protein or polypeptide.

"Treatment" or "treating" refers to therapy, prevention and prophylaxis and particularly refers to the administration of medicine or the performance of medical procedures with respect to a patient, for either prophylaxis (prevention) or to cure or reduce the extent of or likelihood of occurrence of the infirmity or malady or condition or event in the instance where the patient is afflicted.

"Diagnosis" refers to diagnosis, prognosis, monitoring, characterizing, selecting patients, including participants in clinical trials, and identifying patients at risk for or having a particular disorder or clinical event or those most likely to respond to a particular therapeutic treatment, or for assessing or monitoring a patient's response to a particular therapeutic treatment.

"Subject" or "patient" refers to a mammal, preferably a human, in need of treatment for a condition, disorder or disease.

Agents that "increase negative, or decrease positive acting elements affecting SHH-GLI signaling", as used herein, refers to agents that potentiate positive or transactivating function of the Gli proteins, for example, increasing their transcriptional activity on target genes, or agents that decrease their negative or repressive transcription function on target genes.

Tumors that are "apoptotic resistant" are tumors that are inhibited from undergoing apoptosis. This inhibition of apoptosis may be due in part to the expression of at least one of the GLI proteins or gene products.

Tumors that are "resistant to chemotherapeutic agents", are tumors that do not respond to treatment with chemotherapeutic agents, ie. they are not killed by, or their growth is not inhibited by, such treatment. Such resistance may be due at least in part to the expression of at least one of the GLI proteins or gene products.

"Antisense" nucleic acids are DNA or RNA molecules that are complementary to at least a portion of a specific mRNA molecule (See Weintraub, Sci. Amer. 262:40-46 (1990); Marcus-Sekura, Nucl. Acid Res, 15: 5749-5763 (1987); Marcus-Sekura Anal.Biochem., 172:289-295 (1988); Brysch et al., Cell Mol. Neurobiol., 14:557-568 (1994)). In the cell, the single stranded antisense molecule hybridizes to that mRNA, forming a double stranded molecule. The cell does not translate an mRNA in this double-stranded form. Therefore, antisense nucleic acids interfere with the expression of mRNA into protein. Oligomers of greater than about fifteen nucleotides and molecules that hybridize to the AUG initiation codon will be particularly efficient. Antisense methods have been used to inhibit the expression of many genes in vitro (Marcus-Sekura, Anal.Biochem., 172:289-295 (1988); Hambor et al., Proc. Natl. Acad. Sci. U.S.A. 85:4010-4014 (1988)) and in situ (Arima et al., Antisense Nucl. Acid Drug Dev. 8:319-327 (1998); Hou et al.,Antisense Nucl. Acid Drug Dev. 8:295-308 (1998)).

General Description

The Hedgehog-Gli signaling pathway, or SHH/GLI signaling pathway, regulates numerous events during the normal development of many cell types and organs, including the brain, bone, skin, gonads, lung, prostate, gastrointestinal tract and blood. The hedgehog (hh)gene—like many of the components of the signaling pathway triggered by Hedgehog (Hh) protein—was first identified in *Drosophila*, where it affects pattern formation very early in embryonic development. The binding of Hh to cell membranes triggers a signaling cascade that results in the regulation of transcription by zinc-finger transcription factors of the Gli family.

Of the three hh-family genes in mammals—Sonic hedgehog (Shh), Indian hedgehog (Ihh) and Desert hedgehog (Dhh)—Shh has been the most studied, mainly because it is expressed in various tissues but also because experiments with Shh protein are generally also applicable to other members of the family. The correct regulation of the Hh-Gli signaling pathway is essential not only for normal development but also to prevent a number of human diseases associated with abnormally increased or decreased signaling. Here, we discuss the potential use of small-molecule modulators of the Hh-signaling system.

Hedgehogs are secreted glycoproteins that act through the transmembrane proteins Patched1 (Ptc1) and Smoothened (Smo) to activate an intricate intracellular signal-transduction pathway. Hh binds Ptc1, a protein with 12 trans-membrane domains, and this releases the basal repression that Ptc1 exerts on Smo, a 7-transmembrane-domain protein that has homology to G-protein-coupled receptors. Inside the cell, a multimolecular complex, including Costal2 (Cos2), Fused (Fu) and suppressor of Fused (Su(Fu)), responds to the activation of Smo in such a way as to modify the activity of the Gli proteins. There are three Gli transcription factors in vertebrates: Gli1 appears to act as a transcriptional activator and is universally induced in Hh-responding cells, whereas Gli2 and Gli3 can act as activators or repressors of transcription depending on the particular cellular context. The fate of Gli proteins, which appear to reside in the cytoplasm in their inactive state, depends on the state of Hh signaling. In the absence of Hh, Gli3 is processed into a smaller, nuclear transcriptional repressor that lacks the carboxy-terminal domain of full-length Gli3. Upon activation of Smo (and Hh signaling), Gli3 protein cleavage is prevented and an apparent full-length form with transcription-activating function is generated. Gli2 also encodes a repressor function in its carboxy-terminally truncated form, but its formation does not appear to be regulated by Hh signaling.

Mutations in components of the IIH-GLI pathway in humans (human gene and protein names are given in capitals) lead to several diseases that result from either loss of function or ectopic activation of the pathway. For example, haploinsufficiency of SHH or mutation in the human PTCH1 gene are associated with holoprosencephaly, a common syndrome affecting development of the forebrain and mid-face. Moreover, ectopic expression of Shh, Gli1 or Gli2 in model systems leads to the formation of tumors that resemble basal cell carcinomas (BCCs), and sporadic human BCCs consistently express GLI, suggesting that all sporadic BCCs have this pathway active. Similarly, human mutations in the Suppressor of Fused—SU(FU)—gene predispose the carrier to medulloblastoma; sporadic medulloblastomas can carry PTCH1 mutations and express GLI1—again suggesting that they harbor an active pathway—and Ptc+/−mice can develop medulloblastomas. Furthermore, a number of sporadic prostate tumors express GLI1 (Dahmane N, et al. The Sonic Hedgehog-Gli pathway regulates dorsal brain growth and tumorigenesis. *Development* 128, 5201-5212 (2001)), a reliable marker of HH signaling (Lee J, Platt K A, Censullo P, & Ruiz i Altaba A. Gli1 is a target of Sonic hedgehog that induces ventral neural tube development. *Development* 124, 2537-2552 (1997), raising the possibility that this pathway participates in prostate cancer (PC). Moreover, genetic mapping data reveals that at least two of the genes present in the SHH-GLI pathway (SMOH and Suppressor of Fused (SU-FUH)) are located in chromosomal regions implicated in familial human PC by genetic mapping studies Easton, D. F., Schaid, D. J., Whittemore, A. S. & Isaacs, W. J., *Prostate* 57, 261-269 (2003); Xu, J. et al., *Prostate* 57, 320-325 (2003).

From an examination of the different mutations that cause aberrant suppression or activation of the HH-GLI pathway in humans, it seems clear that the development of small molecules that could act as agonists or antagonists of the function of proteins such as PTCH1, SMO or GLI might provide an effective therapeutic approach. One such drug could be SHH protein itself, a natural agonist. For example, it has been reported that injection of Shh into the striatum reduces behavioral deficits in a rat model of Parkinson's disease, that Shh can induce dopaminergic neuronal differentiation and that Shh is a neuroprotective agent. But Shh has a relatively short half-life in serum and its therapeutic effects have been difficult to evaluate in vivo. The use of synthetic Hh agonists could therefore provide a viable alternative to Shh protein. Frank-Kamenetsky et al. have now identified a synthetic non-peptidyl small molecule that faithfully activates the Hh-Gli pathway, triggering the known biological effects of Hh signaling. They have shown that this agonist promotes proliferation and differentiation in a cell-type-specific manner in vitro, while in vivo it rescues developmental defects of Shh-null mouse embryos. But this agonist, unlike Shh protein, appears to bypass the Ptc1-regulatory step, by interacting directly with Smo (*Journal of Biology* 2002, Volume 1, Issue 2, Article 9; Stecca and Ruiz i Altaba, *Journal of Biology* 2002, 1:9. From a therapeutic point of view, the fact that the molecule retains its activity after oral administration is a great advantage and, if its ability to cross the blood-brain and placental barriers occurs in humans, it could be a very valuable therapeutic agent. Nevertheless, systemic side effects are to be expected, as there are many HH-responsive cell populations in the body.

Treatment of human diseases resulting from ectopic HH-GLI pathway activation, such as those caused by oncogenic mutations in SMOH and PTCH1 or in any element of the pathway that results in activation of GLI function, requires the use of pathway antagonists. Up to now, inhibition of ectopic activity has been achieved by treatment with signaling antagonists that block the pathway at different levels: first, blocking anti-Shh antibodies that act extracellularly, second, cyclopamine, a plant alkaloid that acts at the level of Smo in the cell membrane, third, forskolin, an intracellular activator of protein kinase A (PKA) that is a cytoplasmic inhibitor of the pathway; and fourth, Gli-repressor proteins that act within the nucleus to inhibit positive GLI function from mediating the HH signal. Use of forskolin is likely to lead to numerous side effects, given the wide-spread activity of PKA. In contrast, the use of the small molecule cyclopamine or analogs thereof, holds great promise.

A number of studies suggest that cyclopamine specifically inhibits Smo activity and that it can affect disease states caused by activation of the HH-GLI pathway. For example, the proliferation of a number of human brain-tumor cell lines and primary tumor cultures, including those from medulloblastomas and some gliomas as well as medulloblastoma allografts, are inhibited by treatment with cyclopamine. This suggests that pathway activation is required for tumor maintenance. The activity of Gli proteins, the terminal elements of the pathway, is sufficient to induce tumor development. Thus, HH-pathway activity may be involved in the initiation as well as the maintenance of different tumors. This provides an additional opportunity to inhibit the growth of a number of tumors in different organs and tissues, including basal cell carcinoma in the skin, lung cancer (small cell and non small cell lung cancer), prostate cancer, medulloblastoma, glioblastoma and PNETs, and other brian tumors, cancer of the stomach, GI tract, pancreas, rhabdomyosarcomas, and soft tissue sarcomas, all with the same agent. Cyclopamine could be such an agent if the diseases to be treated arise from activation of the HH-signaling pathway at the level of SMOH or above. But cyclopamine is currently very expensive, and alternative HH-pathway antagonists might be economically more attractive. Frank-Kamenetsky et al. (Frank-Kamenetsky et al *J. Biol.* 2002, 1:10) report the use of a new, synthetic, small-molecule inhibitor, Cur61414, which has inhibitory properties similar to those of cyclopamine and also acts at the level of Smo (Williams et al, PNAS, (2003), 100(8):4616-21). Whether Cur61414, or four additional small-molecule antagonists (SANT1-4) that also act on Smo and were recently identified (Chen et al, (2002), PNAS, 99:14071-14076), will prove to be better and easier to use than cyclopamine remains to be determined, but testing them against skin (Williams et al supra) and brain tumors is warranted from a biological point of view.

Finally, given that carboxy-terminally truncated repressor forms of GLI3 are potent inhibitors of the activating output of the HH-signaling pathway, these could be used as antagonists for the treatment of tumors. The difficulty of delivering them into cells might require the development of in vivo transducing strategies, taking advantage, for example, of the ability of the Penetratin, TAT or VP22 peptides to cross cell membranes while loaded with cargo. It also suggests that it would be useful to search for and design small molecules that inhibit GLI's transcription-activating function, perhaps by promoting endogenous GLI-repressor formation. This may be very difficult, but such drugs would be very specific and would be usable in cases where the cancer is due to mutation in the pathway at any level, from the extracellular ligand, the HH proteins, to the final mediators, the GLI proteins. Agents that inhibit HH signaling may induce the regression of tumors that are dependent on a deregulated HH-GLI pathway, but these agents are likely also to affect the behavior of other normal pathway-dependent cells in the patient. This may, however, be a small price to pay in order to combat cancer, and the agents may have fewer side effects than current non-specific cytotoxic anti-cancer chemotherapies.

The present invention provides methodology for treating tumors, e.g., treating brain tumors and lung tumors and other hyperproliferative conditions wherein the condition is characterized as having increased levels of expression of one or more members of the family of GLI proteins. In a preferred embodiment, the invention provides for methods of treating tumors using inhibitors of the sonic hedgehog (SHH) and/or GLI pathways. In another preferred embodiment, the invention provides for treating tumors with short or small interfering RNAs (siRNAs) or cyclopamine. In a yet further embodiment, the tumors are lung tumors. In a more particular embodiment, the lung tumors are small cell or non-small cell lung tumors. In yet another particular embodiment, the tumors are inhibited from undergoing apoptosis due in part to the expression of at least one of the GLI proteins or gene products. In another particular embodiment, the tumors are resistant to chemotherapeutic agents, such resistance being due at least in part to the expression of at least one of the GLI proteins or gene products.

A yet further aspect of the invention provides for pharmaceutical compositions comprising the agents that inhibit tumors whose growth is regulated via the SHH and/or GLI pathway and a pharmaceutically acceptable carrier. In particular, the agents that inhibit tumors are selected from the group consisting of a siRNA, antisense nucleic acid, cyclopamine or analogs or derivatives thereof and is formulated in a composition that allows for delivery via an intravenous, intraperitoneal, subcutaneous, intramuscular, intracerebral, intraventricular, or intrathecal route with a pharmaceutically acceptable carrier.

Nucleic Acids Encoding SHH

The present invention contemplates use of nucleic acids encoding a Hedgehog family member such as sonic hedgehog (e.g., genomic or cDNA) and nucleic acids encoding active fragments thereof. HH can be used from any animal species, including insects, but preferably a mammalian source, and more preferably a human source. In accordance with the present invention there may be employed conventional molecular biology, microbiology, and recombinant DNA techniques within the skill of the art. Such techniques are explained fully in the literature. (See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); Sambrook and Russell, *Molecular Cloning: A Laboratory Manual*, Third Edition (2001) Cold Spring Harbor Laboratory Press, Cold Spring Harbor, N.Y.; *DNA Cloning: A Practical Approach*, Volumes I and II D. N. Glover ed. 1985; *Oligonucleotide Synthesis*, M. J. Gait ed. (1984); *Nucleic Acid Hybridization*, B. D. Hames & S. J. Higgins eds. (1985); *Transcription And Translation*, B. D. Hames & S. J. Higgins, eds. (1984); *Animal Cell Culture*. R. I. Freshney, ed. (1986); *Immobilized Cells And Enzymes*, IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994)).

Accordingly, any animal cell potentially can serve as the nucleic acid source for the molecular cloning of an hh or gli gene. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

The nucleotide sequence of the human SHE, SEQ ID NO: 1, or of the human GLI1, 2, and 3, SEQ ID NOs: 15 (PubMed accession number NM_005269), 17 (PubMed accession number AB007296) and 19 (PubMed accession number NM_000168), respectively, can also be used to search for highly homologous genes from other species, or for proteins having at least one homologous domain, using computer data bases containing either partial or full length nucleic acid sequences. Human ESTs, for example, can be searched. The human Shh sequence can be compared with other human sequences, e.g., in GenBank, using GCG software and the blast search program for example. Matches with highly homologous sequences or portions thereof can then be obtained.

If the sequence identified is an EST, the insert containing the EST can be obtained and then fully sequenced. The resulting sequence can then be used in place of, and/or in conjunction with SEQ ID NO:1 to identify other ESTs which contain coding regions of the SHH homologue (or SHH domain homologue). Plasmids containing the matched EST for example can be digested with restriction enzymes in order to release the cDNA inserts. If the plasmid does not contain the full length homologue the digests can be purified, e.g., run on an agarose gel and the bands corresponding to the inserts can be cut from the gel and purified. Such purified inserts are likely to contain overlapping regions which can be combined as templates of a PCR reaction using primers which are preferably located outside of the SHH open reading frame. Amplification should yield the expected product which can be ligated into a vector and used to transform an *E coli* derivative e.g., via TA cloning (Invitrogen) for example. A resulting full-length SHH homologue can be placed into an expression vector and the expressed recombinant SHH can then be assayed for its ability to stimulate the proliferation and differentiation of brain stem cells.

A modified HH or GLI can be made by altering nucleic acid sequences encoding the HH or GLI by making substitutions, additions or deletions that provide for functionally equivalent molecules. Preferably, such derivatives are made that have enhanced or increased effect on the proliferation and differentiation of adult brain stem cells.

Due to the degeneracy of nucleotide coding sequences, other DNA sequences which encode substantially the same amino acid sequence as an hh gene or a gli gene may be used in the practice of the present invention including those comprising conservative substitutions thereof. These include but are not limited to modified allelic genes, modified homologous genes from other species, and nucleotide sequences comprising all or portions of hh or gli genes which are altered by the substitution of different codons that encode the same amino acid residue within the sequence, thus producing a silent change. Likewise, the HH or GLI derivative of the invention can include, but is not limited to, those containing, as a primary amino acid sequence, all or part of the amino acid sequence of an HH or GLI protein including altered sequences in which functionally equivalent amino acid residues are substituted for residues within the sequence resulting in a conservative amino acid substitution. And thus, such substitutions are defined as a conservative substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to significantly affect apparent molecular weight as determined by polyacrylamide gel electrophoresis, or isoelectric point.

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. Pro may be introduced because of its particularly planar structure.

When comparing a particular full-length SHH for example, with human SHH having the amino acid sequence of SEQ ID NO:2, deletions or insertions that could otherwise alter the correspondence between the two amino acid sequences are taken into account. Preferably standard computer analysis is employed for the determination that is comparable, (or identical) to that determined with an Advanced Blast search at www.ncbi.nlm.nih.gov under the default filter conditions (e.g., using the GCG (Genetics Computer Group, Program Manual for the GCG Package, Version 7, Madison, Wis.) pileup program using the default parameters).

The genes encoding HH or GLI derivatives and analogs of the invention can be produced by various methods known in the art. The manipulations which result in their production can occur at the gene or protein level. For example, an hh or gli gene sequence can be produced from a native hh or gli clone by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of a nucleic acid encoding an HH or GLI, care should be taken to ensure that the modified gene remains within the same translational reading frame as the hh or gli gene, uninterrupted by translational stop signals, in the gene region where the desired activity is encoded.

Additionally, the HH or GLI-encoding nucleic acid sequence can be produced by in vitro or in vivo mutations, to create and/or destroy translation, initiation, and/or termination sequences, or to create variations in coding regions and/or form new restriction endonuclease sites or destroy preexisting ones, to facilitate further in vitro modification. Preferably such mutations will further enhance the specific properties of the hh or gli gene product identified to have the capabilities disclosed by the present invention. Any technique for mutagenesis known in the art can be used, including but not limited to, in vitro site-directed mutagenesis (Hutchinson, C., et al., *J. Biol. Chem.*, 253:6551 (1978); Zoller and Smith, *DNA*, 3:479-488 (1984); Oliphant et al., *Gene*, 44:177 (1986); Hutchinson et al., *Proc. Natl. Acad. Sci. U.S.A.*, 83:710 (1986)), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70). A general method for site-specific incorporation of unnatural amino acids into proteins is described in Noren et al., (*Science*, 244:182-188 (1989)). This method may be used to create analogs with unnatural amino acids.

Expression of HH or GLI Polypeptides and Active Fragments Thereof

The nucleotide sequence coding for an HH or GLI, or a functionally equivalent derivative including a chimeric protein thereof, can be inserted into an appropriate expression vector, i.e., a vector which contains the necessary elements for the transcription and translation of the inserted protein-coding sequence. Such elements are termed herein a "promoter." Thus, the nucleic acid encoding an HH is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native genes encoding the corresponding HH or GLI and/or their flanking regions. Any person with skill in the art of molecular biology or protein chemistry, in view of the present disclosure, would readily know how to assay the HH or GLI expressed as described herein, to determine whether such a modified protein can indeed perform the functions of an HH or GLI taught by the present invention. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used. Expression of an SHH may be controlled by any promoter/enhancer element known in the art, e.g., a Simian Virus 40 (SV40) promoter, a cytomegalus virus promoter (CMV) promoter, or a tissue specific promoter such as the human glial fibrillary acidic protein promoter (GFAP) promoter, as long as these regulatory elements are functional in the host selected for expression. The resulting SHH or GLI protein or fragment thereof can be purified, if desired, by any methodology such as one that is well known in the art.

Production of Cells from Tissue

Cells that can be used in the methods of the present invention can be obtained from tissue specimens, including tumor biopsies by methods known to those skilled in the art.

Once the cells are isolated they can be proliferated and grown in the presence of specific growth medium and any other factor (or molecule) that can maintain cell viability. Thus the cells can be cultured in vitro as described below, in the presence of any other factor (or molecule) that can maintain cell viabilty until cellular testing for the presence of GLI can be done.

Gene Therapy and Transgenic Vectors

A gene encoding an inhibitor of a hedgehog protein, e.g., SHH, or a GLI protein inhibitor, active fragment thereof, derivative thereof, or structural/functional domain thereof, can be introduced either in vivo, ex vivo, or in vitro in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. For example, in the treatment of neurological disorders or injuries, the striatal subventricular zone (SVZ) can be specifically targeted. Examples of particular vectors include, but are not limited to, a defective herpes virus 1 (HSV1) vector (Kaplitt et al., *Molec. Cell. Neurosci.*, 2:320-330 (1991)), an attenuated adenovirus vector, such as the vector described by Stratford-Perricaudet et al. (*J. Clin. Invest.*, 90:626-630 (1992)), and a defective adeno-associated virus vector (Samulski et al., *J. Virol.*, 61:3096-3101 (1987); Samulski et al., *J. Virol.*, 63:3822-3828 (1989)) including a defective adeno-associated virus vector with a tissue specific promoter, (see e.g., U.S. Pat. No. 6,040,172, Issued Mar. 21, 2000, the contents of which are hereby incorporated by reference in their entireties).

In a particular embodiment, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon.- (IFN.-), or anti-CD4 antibody, can be administered to block humoral or cellular immune responses to the viral vectors (see, e.g., Wilson, *Nature Medicine*, (1995)). In addition, it is advantageous to employ a viral vector that is engineered to express a minimal number of antigens.

In another embodiment the inhibitor of the Shh or Gli gene can be introduced in a retroviral vector, e.g., as described in U.S. Pat. No. 5,399,346; Mann et al., (1983) *Cell*, 33:153; U.S. Pat. No. 4,650,764; U.S. Pat. No. 4,980,289; Markowitz et al., (1988) *J. Virol.*, 62:1120; U.S. Pat. No. 5,124,263; International Patent Publication No. WO 95/07358, published Mar. 16, 1995; and Kuo et al., (1993) *Blood*, 82:845.

Targeted gene delivery is described in International Patent Publication WO 95/28494, published October 1995.

Alternatively, the vector can be introduced by lipofection. Liposomes may be used for encapsulation and transfection of nucleic acids in vitro. Synthetic cationic lipids designed to limit the difficulties and dangers encountered with liposome mediated transfection can be used to prepare liposomes for in vivo transfection of a gene encoding SHH (Felgner, et. al., *Proc. Natl. Acad. Sci. U.S.A.*, 84:7413-7417 (1987); see Mackey, et al., *Proc. Natl. Acad. Sci. U.S.A.*, 85:8027-8031 (1988)). The use of cationic lipids may promote encapsulation of negatively charged nucleic acids, and also promote fusion with negatively charged cell membranes (Felgner and Ringold, *Science*, 337:387-388 (1989)). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as the brain. Lipids may be chemically coupled to other molecules for the purpose of targeting (see Mackey et. al., *Proc. Natl. Acad. Sci. U.S.A.*, 85:8027-8031 (1988)).

It is also possible to introduce the vector as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., (1992) *J. Biol. Chem.*, 267:963-967; Wu and Wu, (1988) *J. Biol. Chem.*, 263:14621-14624; Hartmut et al., Canadian Patent Application No. 2,012,311, filed Mar. 15, 1990).

In a preferred embodiment of the present invention, a gene therapy vector as described above employs a transcription control sequence operably associated with the nucleotide sequence encoding the SHH or GLI inhibitor inserted in the vector. That is, a specific expression vector of the present invention can be used in gene therapy.

Such an expression vector is particularly useful to regulate expression of a therapeutic hh gene, e.g., sonic hedgehog gene. In one embodiment, the present invention contemplates constitutive expression of the hh gene, even if at low levels. Alternatively, a regulatable promoter may be used.

Administration

According to the present invention, a therapeutic composition, e.g., an inhibitor or antagonist of the GLI pathway or analog, derivative or fragment thereof and a pharmaceutically acceptable carrier of the invention or an agent such as a small organic molecule that inhibits or antagonizes the GLI pathway and/or decreases expression of GLI, or alternatively, a siRNA, antisense nucleic acid or blocking antibody to block or inhibit the SHH-GLI pathway to prevent tumorigenesis, may be introduced orally, parenterally, transmucosally, e.g., nasally. Preferably, administration is by intracranial, intrathecal or intraventricular administration for tumors in the brain. For brain tumors or any other tumors, such as lung, the agents of the invention may be delivered via the oral route, the intravenous route, the intramuscular route, the subcutaneous route or via aerosolized therapy. Alternatively, the therapeutic composition can be placed (e.g., injected) into the bloodstream after coupling the SHH/GLI protein inhibitor or active fragment thereof to a carrier that will allow the SHH/GLI protein inhibitor or active fragment thereof-carrier complex to cross the blood-brain barrier.

In a preferred aspect, an HH or GLI protein inhibitor of the present invention can cross cellular or nuclear membranes, which would allow for intravenous or oral administration. Strategies are available for such crossing, including but not limited to, increasing the hydrophobic nature of a molecule; introducing the molecule as a conjugate to a carrier, such as a ligand to a specific receptor, targeted to a receptor; and the like.

The present invention also provides for conjugating targeting molecules to an HH or GLI protein. "Targeting molecule" as used herein shall mean a molecule which, when administered in vivo, localizes to desired location(s). In various embodiments, the targeting molecule can be a peptide or protein, antibody, lectin, carbohydrate, or steroid. In one embodiment, the targeting molecule is a peptide ligand of a receptor on the target cell. (On the other hand SHH may itself be considered a targeting molecule since it binds its own receptor). In a specific embodiment, the targeting molecule is an antibody. Preferably, the targeting molecule is a monoclonal antibody. In one embodiment, to facilitate crosslinking the antibody can be reduced to two heavy and light chain heterodimers, or the F(ab')$_2$ fragment can be reduced, and crosslinked to the SHH protein or GLI protein via a reduced sulfhydryl.

Antibodies for use as targeting molecule are specific for cell surface antigen. In one embodiment, the antigen is a receptor. For example, an antibody specific for a receptor on a brain cell can be used. This invention further provides for the use of other targeting molecules, such as lectins, carbohydrates, proteins and steroids.

In another embodiment, the therapeutic compound can be delivered in a vesicle, in particular a liposome (see Langer, (1990) *Science,* 249:1527-1533; Treat et al., (1989) in *Liposomes in the Therapy of Infectious Disease and Cancer*, Lopez-Berestein and Fidler (eds.), Liss: New York, pp. 353-365; Lopez-Berestein, ibid., pp. 317-327; see generally ibid.).

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used (see Langer (1990) supra; Sefton, (1987) *CRC Crit. Ref Biomed. Eng.,* 14:201; Buchwald et al., (1980) *Surgery,* 88:507; Saudek et al., (1989) *N. Engl. J. Med.,* 321: 574). In another embodiment, polymeric materials can be used (see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, (1983) *J. Macromol. Sci. Rev. Macromol. Chem.,* 23:61; see also Levy et al., (1985) *Science,* 228:190; During et al., (1989) *Ann. Neurol.,* 25:351; Howard et al., (1989) *J. Neurosurg.,* 71:105). In yet another embodiment, a controlled release system can be placed in proximity of the therapeutic target, i.e., the brain, thus requiring only a fraction of the systemic dose (see, e.g., Goodson, in *Medical Applications of Controlled Release*, supra, vol. 2, pp. 115-138 (1984)). Preferably, a controlled release device is introduced into a subject in proximity of the adult brain stem cells, e.g., the striatal subventricular zone (SVZ). Other controlled release systems are discussed in the review by Langer (1990) supra.

Antisense Therapy

The relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state. In the present invention, the targets are nucleic acids encoding GLI; in other words, a gene encoding GLI, or mRNA expressed from the gli gene. mRNA which encodes GLI (GLI1, GLI2 or GLI3) is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention, which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-WUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding GLI, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3') from a translation initiation codon. This region is a particular target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a particular target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns", which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide. "Stringent hybridization conditions" are defined as hybridization in 7% sodium dodecyl sulfate (SDS), 1 mM EDTA at 65° C. and washing in 0.1×SSC/0.1% SDS at 68° C.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of GLI. In the context of this invention "modulation" means either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

The antisense oligonucleotides of this invention can be used in diagnostics, therapeutics, prophylaxis, and as research reagents and in kits. Since the oligonucleotides of this invention hybridize to nucleic acids encoding GLI, sandwich, colorimetric and other assays can easily be constructed to exploit this fact. Provision of means for detecting hybridization of oligonucleotide with the gli gene or mRNA can routinely be accomplished. Such provision may include enzyme conjugation, radiolabelling or any other suitable detection systems. Kits for detecting the presence or absence of GLI may also be prepared.

The present invention is also suitable for diagnosing certain cancers in tissue or other samples from patients suspected of having hyperproliferative condition or cancer such as, but not limited to brain cancer, skin cancer, lung cancer, bladder cancer and prostate cancer. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 10 to about 50 nucleobases. Particularly preferred are antisense oligonucleotides comprising from about 10 to about 30 nucleobases (i.e. from about 10 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2=, 3=or 5=hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3=to 5=phosphodiester linkage.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering 1990, pages 858-859, Kroschwitz, J. I., ed. John Wiley & Sons, those disclosed by Englisch et al. (Angewandte Chemie, International Edition 1991, 30, 613-722), and those disclosed by Sanghvi, Y. S., Chapter 15, Antisense Research and Applications 1993, pages 289-302, Crooke, S. T. and Lebleu, B., ed., CRC Press. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications 1993, CRC Press, Boca Raton, pages 276-278) and are presently preferred base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA 1989, 86, 6553-6556), cholic acid (Manoharan et al., Bioorg. Med. Chem. Lett. 1994, 4, 1053-1059), a thioether, e.g., hexyl-S-tritylthiol (Manoharan et al., Ann. N.Y. Acad. Sci. 1992, 660, 306-309; Manoharan et al., Bioorg. Med. Chem. Let. 1993, 3, 2765-2770), a thiocholesterol (Oberhauser et al., Nucl. Acids Res. 1992, 20, 533-538), an aliphatic chain, e.g., dodecandiol or undecyl residues (Saison-Behmoaras et al., EMBO J. 1991, 10, 1111-1118; Kabanov et al., FEBS Lett. 1990, 259, 327-330; Svinarchuk et al., Biochimie 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett. 1995, 36, 3651-3654; Shea et al., Nucl. Acids Res. 1990, 18, 3777-3783), a polyamine or a polyethylene glycol chain (Manoharan et al., Nucleosides & Nucleotides 1995, 14, 969-973), or adamantane acetic acid (Manoharan et al., Tetrahedron Lett. 1995, 36, 3651-3654), a palmityl moiety (Mishra et al., Biochim. Biophys. Acta 1995, 1264, 229-237), or an octadecylamine or hexylamino-carbonyl-oxycholesterol moiety (Crooke et al., J. Pharmacol. Exp. Ther. 1996, 277, 923-937).

Representative U.S. patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the skilled artisan. It is well known to use similar techniques to prepare oligonucleotides such as the phosphorothioates and 2'-alkoxy or 2'-alkoxyalkoxy derivatives, including 2'-O-methoxyethyl oligonucleotides (Martin, P., Helv. Chim. Acta 1995, 78, 486-504). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids. Pharmaceutically acceptable salts are physiologically and pharmaceutically acceptable salts of the nucleic acids of the invention: i.e., salts that retain the desired biological activity of the parent compound and do not impart undesired toxicological effects thereto (see, for example, Berge et al., "Pharmaceutical Salts," J. of Pharma Sci. 1977, 66, 1-19).

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention may be prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention (the antisense oligonucleotides and the siRNA molecules described below) may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., Critical Reviews in Therapeutic Drug Carrier Systems 1991, 8, 91-192; Muranishi, Critical Reviews in Therapeutic Drug Carrier Systems 1990, 7, 1-33). One or more penetration enhancers from one or more of these broad categories may be included. Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., Critical Reviews in Therapeutic Drug Carrier Systems 1991, page 92; Muranishi, Critical Reviews in Therapeutic Drug Carrier Systems 1990, 7, 1; El-Hariri et al., J. Pharm. Pharnacol. 1992 44, 651-654).

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations.

Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., Critical Reviews in Therapeutic Drug Carrier Systems 1991, page 92; Muranishi, Critical Reviews in Therapeutic Drug Carrier Systems 1990, 7, 1-33; Buur et al., J. Control Rel. 1990, 14, 43-51). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al., Critical Reviews in Therapeutic Drug Carrier Systems 1991, page 92); and perfluorochemical emulsions, such as FC-43 (Takahashi et al., J. Pharm. Pharmacol. 1988, 40, 252-257).

Non-surfactants include, for example, unsaturated cyclic ureas, 1-alkyl- and 1-alkenylazacyclo-alkanone derivatives (Lee et al., Critical Reviews in Therapeutic Drug Carrier Systems 1991, page 92); and non-steroidal anti-inflammatory agents such as diclofenac sodium, indomethacin and phenylbutazone (Yamashita et al., J. Pharm. Pharmacol. 1987, 39, 621-626).

As used herein, "carrier compound" as used in the context of the oligonucleotides of the present invention, refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 1995, 6, 698-708).

The pharmaceutical compositions of the present invention may be administered in a number of ways depending upon whether local or systemic treatment is desired and upon the area to be treated. Administration may be topical (including ophthalmic, vaginal, rectal, intranasal, epidermal, and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved.

Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ found to be effective in vitro and in in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

siRNA Therapy

In general terms, RNA interference (RNAi) is the process whereby the introduction of double stranded RNA into a cell inhibits the expression of a gene corresponding to its own sequence. RNAi is usually described as a post-transcriptional gene-silencing (PTGS) mechanism in which dsRNA triggers degradation of homologous messenger RNA in the cytoplasm. The mediators of RNA interference are 21- and 23-nucleotide small interfering RNAs (siRNA) (Elbashir, S. M. et al., (2001), Genes Dev. 15, 188-200; Elbashir, S. M. et al. (2001), Nature 411: 494498; Hutvagner, G. et al., (2001), Science 293:834-838). In a second step, siRNAs bind to a ribonuclease complex called RNA-induced silencing complex (RISC) that guides the small dsRNAs to its homologous mRNA target. Consequently, RISC cuts the mRNA approximately in the middle of the region paired with the antisense siRNA, after which the mRNA is further degraded. A ribonuclease im enzyme, dicer, is required for processing of long dsRNA into siRNA duplexes (Bernstein, E. et al. ((2001), Nature 409: 363-366).

Mechanism of RNAi

The only RNA molecules normally found in the cytoplasm of a cell are molecules of single-stranded mRNA. If the cell finds molecules of double-stranded RNA (dsRNA), it uses a ribonuclease III enzyme, dicer, for processing of long dsRNA into siRNA duplexes (Bernstein, E. et al. ((2001), Nature 409: 363-366) containing ~22 base pairs (~2 turns of a double helix). Dicer is a bidentate RNase III, which also contains an ATP-dependent RNA helicase domain and a PAZ domain, presumably important for dsRNA unwinding and mediation of protein-protein interactions, respectively ((Bernstein, E. et al. ((2001), Nature 409: 363-366). Dicer is evolutionarily conserved in worms, flies, plants, fungi and mammals, and has a second cellular function important for the development of these organisms (Grishok, A. (2001), Cell 106:23-34; Knight, S. W. et al. (2001), Science 293:2269-2271; Hutvagner, G. et al., (2001), Science 293:834-838). At present, it is uncertain whetherdicer activity in species other than *D. melanogaster* produces siRNAs of predominantly 21 nt in length. The estimates of siRNA size vary in the literature between 21 and 25 nt(Hamilton, A. J. et al. (1999), Science 286: 950-952; Zamore, P. D. et al. (2000), Cell 101: 25-33; Elbashir, S. M. et al., (2001), Genes Dev. 15, 188-200; Elbashir, S. M. et al. (2001), Nature 411: 494-498; Hammond, S. M. et al. (2000), Nature 404: 293-296; Hutvagner, G. et al., (2001), Science 293:834-838

The two strands of each fragment then separate enough to expose the antisense strand so that it can bind to the complementary sense sequence on a molecule of mRNA. In RNAi, a siRNA-containing endonuclease complex cleaves a single-stranded target RNA in the middle of the region complementary to the 21 nt guide siRNA of the siRNA duplex (Elbashir, S. M. et al., (2001), Genes Dev. 15, 188-200; Elbashir, S. M. et al. (2001), Nature 411: 494-498). This cleavage site is one helical turn displaced from the cleavage site that produced the siRNA from long dsRNA, suggesting dramatic conformational and/or compositional changes after processing of long dsRNA to 21 nt siRNA duplexes. The target RNA cleavage products are rapidly degraded because they either lack the stabilizing cap or poly(A) tail. A protein component of the ~500 kDa endonuclease or RNA-induced silencing complex (RISC) was recently identified and is a member of the argonaute family of proteins (Hammond, S. M. et al. (2001) Science 293: 1146-1150), however, it is currently unclear whether dicer is required for RISC activity. Thus, the cleavage of the mRNA destroys its ability to be translated into a polypeptide. Because of their action, these fragments of RNA have been named "short (or small) interfering RNA" (siRNA).

Introducing dsRNA corresponding to a particular gene will knock out the cell's own expression of that gene. This can be done in particular tissues at a chosen time. This often provides an advantage over conventional gene "knockouts" where the missing gene is carried in the germline and thus whose absence may kill the embryo before it can be studied.

Although it has been suggested that the one disadvantage of simply introducing dsRNA fragments into a cell is that gene expression is only temporarily reduced, it has recently been shown that the system can be manipulated using a DNA vector such that the siRNA molecule can be continuously synthesized for prolonged periods of time in order to continue in suppression of the desired gene (Brummelkamp et. al. 19 Apr. 2002, Science). After two months, the cells still failed to manufacture the protein whose gene had been turned off by RNAi. Effective siRNA molecules may be designed using the following guidelines:

In general, siRNA oligonucleotides should be about 21 nucleotides in length with 2 nucleotide overhangs, usually 3' TT.

Sequences located in the 5' or 3' UTR of the mRNA target and nearby the start codon should be avoided, as they may be richer in regulatory protein binding sites.

Search for a sequence AA(N19)TT or AA(N21) with approximately 50% G/C content.

Compare the selected siRNA nucleotide sequence against databases to ensure that only one gene will be targeted.

Target recognition is a highly sequence specific process, mediated by the siRNA complementary to the target. One or two base pair mismatches between the siRNA and the target gene will greatly reduce the silencing effect. It might be necessary to test several sequences since positional effects of siRNAs have been reported.

The 3'-most nucleotide of the guide siRNA does not contribute to the specificity of target recognition, while the penultimate nucleotide of the 3' overhang affects target RNA cleavage and a mismatch reduces RNAi 2- to 4-fold. The 5' end of the guide siRNA also appears more permissive for mismatched target RNA recognition when compared with the 3' end. Nucleotides in the center of the siRNA, located opposite to the target RNA cleavage site, are important specificity determinants and even single nucleotide changes reduce RNAi to undetectable levels. This suggests that siRNA duplexes may be able to discriminate mutant or polymorphic alleles in gene targeting experiments, which may become an important feature for future therapeutic developments.

Double-stranded RNA has been shown to attenuate specific gene expression in C. elegans, Drosophila and Trypanosoma brucei (M. Montgomery, et al., Proc. Natl. Acad. Sci. U.S.A. 95, 15502-15507 (1998); J. Kennerdell et al., Cell 95, 1017-1026 (1998); H. Ngo et al., Proc. Natl. Acad. Sci. U.S.A. 95, 14687-14692 (1998)). The types of genes attenuated in these invertebrates include some encoding transcription factors and others that encode growth factor receptors. There is also evidence that double-stranded RNA may effectively silence gene expression in plants (M. Wassenegger et al., Plant. Mol. Biol. 37, 349-362 (1998); P. Watergiyse et al., Proc. Natl. Acad. Sci. U.S.A. 95, 13959-13964 (1998)).

A definitive mechanism through which double-stranded RNA effects gene silencing remains has not been identified (M. Montgomery et al., Trends Genet. 14, 255-258 (1998)). Recently, Montgomery et al. reported that double-stranded RNA induces specific RNA degradation in nematodes (Proc. Natl. Acad. Sci. U.S.A. 95, 15502-15507 (1998)). This conclusion was based upon the fact that DNA sequences in the targeted regions of the gene were not altered and that 100% of the F2 generation reverted to the wild type phenotype. In addition, C. elegans has a unique genetic organization. Genes in this animal are organized in operons in which a single promoter controls expression of a number of genes. They showed that the double-stranded RNA affects only expression of the targeted gene. In contrast, however, others have observed heritable effects of double-stranded RNA on the expression of a number of genes in C. elegans, suggesting that more than one mechanism may be involved in double-stranded RNA-mediated inhibition of gene activity (H. Tahara, Science 28, 431432 (1998)).

The present invention provides a method for attenuating gene expression in a cell using gene-targeted double-stranded RNA (dsRNA). The dsRNA contains a nucleotide sequence that is essentially identical to the nucleotide sequence of at least a portion of the target gene, in the matter of the present invention, the shh or gli genes. The cell into which the dsRNA is introduced is preferably a tumor cell containing at least one gli gene to which the dsRNA is targeted. Gene expression can be attenuated in a whole organism, an organ or tissue of an organism, including a tissue explant, or in cell culture. Preferably, the cell is a mammalian cell, but the invention is not limited to mammals. Double-stranded RNA is introduced directly into the cell or, alternatively, into the extracellular environment from which it is taken up by the cell. Inhibition is specific for the targeted gene. Depending on the particular target gene and the dose of dsRNA delivered, the method may partially or completely inhibit expression of the gene in the cell. The expression of two or more genes can be attenuated concurrently by introducing two or more double stranded RNAs into the cell in amounts sufficient to attenuate expression of their respective target genes. Double stranded RNAs that are administered "concurrently" are administered, together or separately, so as to be effective at generally the same time.

In yet another aspect, the invention provides a method for attenuating the expression of a gli gene in a cell that includes annealing two complementary single stranded RNAs in the presence of potassium chloride to yield double stranded RNA; contacting the double stranded RNA with RNAse to purify the double stranded RNA by removing single stranded RNA; and introducing the purified double stranded RNA into the cell in an amount sufficient to attenuate expression of the target gene, e.g. at least one of the gli genes.

The invention further provides a method for treating or preventing a hyperproliferative condition or a cancerous condition in a mammal. Double stranded RNA is administered to the mammal in an amount sufficient to attenuate expression of the gli gene, the expression of which is associated with the cancerous condition. Concurrent inhibition of multiple genes is advantageous to treat diseases associated with multiple genes, or to treat two or more diseases or infections concurrently.

The present invention provides a method for gene silencing in organisms and cells, especially mammals, using gene-specific double-stranded RNA. The ability to use double-stranded RNA to specifically block expression of particular genes in a multicellular setting both in vivo and in vitro has broad implications for the study of numerous diseases, in the matter of the present invention, cancerous conditions.

The method of the present invention allows for attenuation of gene expression in a cell. "Attenuation of gene expression" can take the form of partial or complete inhibition of gene function. Mechanistically, gene function can be partially or completely inhibited by blocking transcription from the gene to mRNA, or by blocking translation of the mRNA to yield the protein encoded by the gene, although it should be understood that the invention is not limited to any particular mechanism of attenuation of gene expression. Inhibition of gene function is evidenced by a reduction or elimination, in the cell, of the activity associated with the protein encoded by the gene. Whether and to what extent gene function is inhibited can be determined using methods known in the art. For example, in many cases inhibition of gene function leads to a change in phenotype which is revealed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Attenuation of gene expression can be quantified, and the amount of attenuation of gene expression in a treated cell compared to a cell not treated according to the present invention can be determined. Lower doses dsRNA may result in inhibition in a smaller fraction of cells, or in partial inhibition in cells. In addition, attenuation of gene expression can be time-dependent; the longer the period of time since the administration of the dsRNA, the less gene expression may be attenuated. Attenuation of gene expression can occur at the level of transcription (i.e., accumulation of mRNA of the targeted gene), or translation (i.e., production of the protein encoded by the targeted gene). For example, mRNA from the targeted gene can be detected using a hybridization probe having a nucleotide sequence outside the region selected for the inhibitory double-stranded RNA, and translated polypeptide encoded by the target gene can be detected via Western blotting using an antibody raised against the polypeptide. It should be noted that the method of the invention is not limited to any particular mechanism for reducing or eliminating cellular protein activity; indeed, as noted above, it is not yet fully understood how the introduction of dsRNA into a cell causes attenuation of expression of the targeted gene, nor is it known whether single or multiple mechanisms are at work.

The attenuation of gene expression achieved by the method of the invention is specific for the gli genes, that is, gli1, gli2 or gli3. In other words, the dsRNA inhibits at least one of the target genes without manifest effects on other genes of the cell.

Double-Stranded RNA

The dsRNA is formed from one or more strands of polymerized ribonucleotide. When formed from only one strand, it takes the form of a self-complementary hairpin-type molecule that doubles back on itself to form a duplex. When formed from two strands, the two strands are complementary RNA strands. The dsRNA can include modifications to either the phosphate-sugar backbone or the nucleoside. For example, the phosphodiester linkages of natural RNA may be modified to include at least one of a nitrogen or sulfur heteroatom. Likewise, bases may be modified to block the activity of adenosine deaminase.

The nucleotide sequence of the dsRNA is defined by the nucleotide sequence of its targeted gene, ie. gli1, gli2 or gli3 (Seq ID NOs: 15, 17, and 19, respectively). The dsRNA contains a nucleotide sequence that is essentially identical to at least a portion of the target gene; preferably the dsRNA contains a nucleotide sequence that is completely identical to at least a portion of the target gene. It should be understood that in comparing an RNA sequence to a DNA sequence, an "identical" RNA sequence will contain ribonucleotides where the DNA sequence contains deoxyribonucleotides, and further that the RNA sequence will contain a uracil at positions where the DNA sequence contains thymidine. More preferably, the dsRNA that is completely identical to at least a portion of the target gene does not contain any additional nucleotides.

A dsRNA that is "essentially identical" to a least a portion of the target gene, e.g. gli, is a dsRNA wherein one of the two complementary stands (or, in the case of a self-complementary RNA, one of the two self-complementary portions) is either identical to the sequence of that portion of the target gene or contains one or more insertions, deletions or single point mutations relative to the nucleotide sequence of that portion of the target gene. The invention thus has the advantage of being able to tolerate sequence variations that might be expected due to genetic mutation, strain polymorphism, or evolutionary divergence. Alternatively, a dsRNA that is "essentially identical" to at least a portion of the target gene can be functionally as a dsRNA wherein one of the two complementary strands (or, in the case of a self-complementary RNA, one of the two self-complementary portions) is capable of hybridizing with a portion of the target gene transcript (e.g., under conditions including 400 mM NaCl, 40 mM PIPES pH 6.4, 1 mM EDTA, 50° C. or 70° C. hybridization for 12-16 hours; followed by washing).

The dsRNA nucleotide sequence that is essentially or completely identical to at least a portion of the target gene has a length of preferably at least about 5-10 bases, more preferably 10-30 bases, more preferably 10-50 bases. The dsRNA nucleotide sequence has a length of preferably less than about 400 bases, more preferably less than about 300 base, more preferably less than about 200 bases and most preferably less than about 100 bases. It will be understood that the length of the dsRNA, the degree of homology necessary to affect gene expression, and the most effective dosages can be optimized for each particular application using routine methods.

Synthesis of dsRNA

Single strands of RNA are synthesized in vitro. Preferably, single stranded RNA is enzymatically synthesized from the PCR products of a DNA template, preferably a cloned a cDNA template. Provided the sequence of the target gene is known, e.g. gli, a cloned cDNA template can be readily made from target cell RNA using reverse-transcriptase polymerase chain reaction (RT-PCR) to generate a cDNA fragment, following by cloning the cDNA fragment into a suitable vector. Preferably, the vector is designed to allow the generation of complementary forward and reverse PCR products. The vector pGEM-T (Promega, Madison Wis.) is well-suited for use in the method because it contains a cloning site positioned between oppositely oriented promoters (i.e., T7 and SP6 promoters; T3 promoter could also be used). After purification of the PCR products, complementary single stranded RNAs are synthesized, in separate reactions, from the DNA templates via RT-PCR using two different RNA polymerases (e.g., in the case of pGEM-T, T7 polymerase and SP6 polymerase). RNAse-free DNAse is added to remove the DNA template, then the single-stranded RNA is purified. Single strands of RNA can also be produced enzymatically or by partial/total organic synthesis. The use of in vitro enzymatic or organic synthesis allows the introduction of any desired modified ribonucleotide. The RNA strands may or may not be polyadenylated; and the RNA strands may or may not be capable of being translated into a polypeptide by a cell's translational apparatus. Preferably, purification of RNA is performed without the use of phenol or chloroform.

Double stranded RNA is formed in vitro by mixing complementary single stranded RNAs, preferably in a molar ratio of at least about 3:7, more preferably in a molar ratio of about 4:6, and most preferably in essentially equal molar amounts (i.e., a molar ratio of about 5:5). Preferably, the single stranded RNAs are denatured prior to annealing, and the buffer in which the annealing reaction takes place contains a salt, preferably potassium chloride. Prior to administration, the mixture containing the annealed (i.e., double stranded) RNA is preferably treated with an enzyme that is specific for single stranded RNA (for example, RNAse A or RNAse T) to confirm annealing and to degrade any remaining single stranded RNAs. Addition of the RNAse also serves to excise any overhanging ends on the dsRNA duplexes.

Delivery of dsRNA to a Cell

Double stranded RNA can be introduced into the cell in a number of different ways. For example, the dsRNA is conveniently administered by microinjection; other methods of introducing nucleic acids into a cell include bombardment by particles covered by the dsRNA, soaking the cell or organism in a solution of the dsRNA, electroporation of cell membranes in the presence of the dsRNA, liposome-mediated delivery of dsRNA and transfection mediated by chemicals such as calcium phosphate, viral infection, transformation, and the like. The dsRNA may be introduced along with components that enhance RNA uptake by the cell, stabilize the annealed strands, or otherwise increase inhibition of the target gene. In the case of a cell culture or tissue explant, the cells are conveniently incubated in a solution containing the dsRNA or lipid-mediated transfection; in the case of a whole animal or plant, the dsRNA is conveniently introduced by injection or perfusion into a cavity or interstitial space of an organism, or systemically via oral, topical, parenteral (including subcutaneous, intramuscular and intravenous administration), vaginal, rectal, intranasal, ophthalmic, or intraperitoneal administration. In addition, the dsRNA can be administered via and implantable extended release device. Methods for oral introduction include direct mixing of RNA with food of the organism, as well as engineered approaches in which a species that is used as food is engineered to express an RNA, then fed to the organism to be affected. The dsRNA may be sprayed onto a plant or a plant may be genetically engineered to express the RNA in an amount sufficient to kill some or all of a pathogen known to infect the plant.

Alternatively, dsRNA can be supplied to a cell indirectly by introducing one or more vectors that encode both single strands of a dsRNA (or, in the case of a self-complementary RNA, the single self-complementary strand) into the cell. Preferably, the vector contains 5' and 3' regulatory elements that facilitate transcription of the coding sequence. Single stranded RNA is transcribed inside the cell, and, presumably, double stranded RNA forms and attenuates expression of the target gene. Methods for supplying a cell with dsRNA by introducing a vector from which it can be transcribed are set forth in WO 99/32619 (Fire et al., published 1 Jul. 1999). A transgenic animal that expresses RNA from such a recombinant construct may be produced by introducing the construct into a zygote, an embryonic stem cell, or another multipotent cell derived from the appropriate organism. A viral construct packaged into a viral particle would accomplish both efficient introduction of an expression construct into the cell and transcription of RNA encoded by the expression construct.

The dsRNA is typically administered in an amount that allows delivery of at least one copy per cell. The amount of dsRNA administered to a cell, tissue, or organism depends on the nature of the cell, tissue, or organism, the nature of the target gene, and the nature of the dsRNA, and can readily be optimized to obtain the desired level of gene inhibition. To attenuate gene expression in a single cell embryo, for example, at least about $0.8 \times 10^6$ molecules of dsRNA are injected; more preferably, at least about $20 \times 10^6$ molecules of dsRNA are injected; most preferably, at least about $50 \times 10^6$ molecules of dsRNA are injected. The amount of dsRNA injected into a single cell embryo is, however, preferably at most about $1000 \times 10^6$ molecules; more preferably, it is at most about $500 \times 10^6$ molecules, most preferably, at most about $100 \times 10^6$ molecules. In the case of administration of dsRNA to a cell culture or to cells in tissue, by methods other than injection, for example by soaking, electroporation, or lipid-mediated transfection, the cells are preferably exposed to similar levels of dsRNA in the medium. For example, 8-10 μL of cell culture or tissue can be contacted with about $20 \times 10^6$ to about $2000 \times 10^6$ molecules of dsRNA, more preferably about $100 \times 10^6$ to about $500 \times 10^6$ molecules of dsRNA, for effective attenuation of gene expression.

Once the minimum effective length of the dsRNA has been determined, it is routine to determine the effects of dsRNA agents that are produced using synthesized oligoribonucleotides. The administration of the dsRNA can be by microinjection or by other means used to deliver nucleic acids to cells and tissues, including culturing the tissue in medium containing the dsRNA.

The siRNA molecules of the present invention may be used to introduce dsRNA into a cell for the treatment or prevention of disease. To treat or prevent a disease or other pathology, a target gene is selected which is required for initiation or maintenance of the disease/pathology. The dsRNA can be introduced into the organism using in vitro, ex vivo or by in vivo methods. In an in vitro method, the dsRNA is introduced into a cell, which may or may not be a cell of the organism, and the dsRNA-containing cell is then introduced into the organism. In an ex vivo method, cells of the organism are explanted, the dsRNA is introduced into the explanted cells, and the dsRNA-containing cells are implanted back into the host. In an in vivo method, dsRNA is administered directly to the organism. As noted above, the dsRNA can also be delivered to a cell using one or more vectors that encode the complementary RNAs (or self-complementary RNA), which are then transcribed inside the cell and annealed to yield the desired dsRNA.

In medical applications, the dsRNA may be introduced into a cancerous cell or tumor, and thereby inhibit expression of a gene required for maintenance of the carcinogenic/tumorigenic phenotype.

Lung Cancer: General Considerations

There are a number of different varieties of lung cancer in humans, including the following:

squamous cell carcinoma, cancer of the layered, squamous epithelium (surface cells) of the lungs or bronchi adenocarcinoma, cancer of the glandular tissue, or cancer in which the tumor cells form recognizable glandular patterns large cell carcinoma, cancer composed of large-sized cells that are anaplastic in nature and often arise in the bronchi broncho-alveolar carcinoma mixed and undifferentiated pulmonary carcinomas.

Because of various treatment concerns, most experts separate lung cancers into two groups: small cell lung carcinoma (SCLC) and non-small cell lung carcinoma (NSCLC). Small cell lung carcinoma often is widespread by the time of diagnosis, so that treatment is limited to chemotherapy and/or radiation therapy. By contrast, non-small cell carcinoma may not have spread at the time of diagnosis, so that surgical resection, or cutting away, of the tumor is possible.

Non-Small Cell Lung Carcinoma

Non-small cell lung carcinoma (NSCLC) includes squamous cell carcinoma, adenocarcinoma, and large cell carcinoma. Large cell carcinoma and adenocarcinoma usually are found on the periphery (outer edges) of the lungs and may occur as solitary nodules, masses, or scar cancer. By contrast, squamous cell carcinoma and small cell carcinoma often are centrally located and may appear to be pneumonia (inflammation of the lungs), atelectasis (collapsed lung), or pit-like masses. Squamous cell cancers frequently are slow growing and can take several years to progress from a confined tumor into invasive cancer. Adenocarcinoma tends to have a worse prognosis than squamous cell cancer in all stages. The prognosis of large cell cancer, an uncommon NSCLC, is similar to that of adenocarcinoma.

Small Cell Lung Carcinoma (SCLC)

Small cell lung carcinoma (SCLC) accounts for approximately 20% of all primary lung cancers, or about 30,000-35,000 cases per year. The histologic distinction between non-small cell lung cancer and small cell lung cancer is extremely important. There are substantial differences between the two groups in both treatment and prognosis. In general, small cell lung cancer tends to be more aggressive and spreads sooner to distant sites. Some studies suggest that 60% to 70% of patients with small cell lung cancer have evidence of distant spread at the time of initial diagnosis. Yet small cell lung cancer also is inclined to be more responsive to chemotherapy and chest radiotherapy. The treatment of small cell lung cancer is not based upon surgery; rather, most physicians employ a systemic approach that includes chemotherapy and local control with radiotherapy. Smoking is the major risk factor for the development of small cell lung carcinoma.

A person is assigned a clinical "stage" of lung cancer after undergoing a diagnostic work-up. Staging describes the extent of disease. It is based on a pathology (disease) report from tissue obtained during bronchoscopy, needle (or other) biopsy, blood work, and imaging studies to rule out distant metastases. Imaging studies include chest X-ray, abdominal ultrasound (images produced by high-frequency sound waves) of the liver, radionuclide (radioactive atom-based) bone scans, and CT or CAT scan (computer-assisted technique that produces cross-sectional images of the body) or magnetic resonance imaging (MRI) of the brain, chest, and abdomen. Staging is complete when a patient has undergone surgical pathology and imaging studies. The physician then uses all available information to determine the stage that best describes the patient's condition. The combined results of the above tests help the physician to assess the overall stage of the disease and also helps in determining the aggressiveness or invasiveness of the cancer. While current research is centered on developing a less invasive means for assessing the aggressiveness of a lung tumor, there are no current tests or biomarkers that allow an accurate diagnosis or prognosis of this condition. Accordingly, the need for such a test or biomarker still exists.

Pharmaceutical Compositions

In yet another aspect of the present invention, provided are pharmaceutical compositions of the above. Such pharmaceutical compositions may be for administration for nasal or other forms of administration. In general, comprehended by the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. (1990), Mack Publishing Co., Easton, Pa. 18042 pages 1435-1712 which are herein incorporated by reference. The compositions may be prepared in liquid form, or may be in dried powder, such as lyophilized form.

Nasal Delivery

Nasal delivery of an HH protein or derivative thereof is also contemplated. Nasal delivery allows the passage of the protein to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Liquid Aerosol Formulations

The present invention provides aerosol formulations and dosage forms. In general such dosage forms contain a pharmaceutical composition of the present invention in a pharmaceutically acceptable diluent. Pharmaceutically acceptable diluents include but are not limited to sterile water, saline, buffered saline, dextrose solution, and the like.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure.

Aerosol Dry Powder Formulations

It is also contemplated that the present aerosol formulation can be prepared as a dry powder formulation comprising a finely divided powder form of pharmaceutical composition of the present invention and a dispersant. Formulations for dispensing from a powder inhaler device will comprise a finely divided dry powder containing pharmaceutical composition of the present invention (or derivative) and may also include a bulking agent, such as lactose, sorbitol, sucrose, or mannitol in amounts which facilitate dispersal of the powder from the device, e.g., 50 to 90% by weight of the formulation. The pharmaceutical composition of the present invention (or derivative) should most advantageously be prepared in particulate form with an average particle size of less than 10 mm (or microns), most preferably 0.5 to 5 mm, for most effective delivery to the distal lung.

In a further aspect, recombinant cells that have been transformed with an hh gene or a gli gene, and that express high levels of the polypeptide can be transplanted in a subject in need of the HH or GLI protein. Preferably autologous cells transformed with HH or a GLI protein are transplanted to avoid rejection; alternatively, technology is available to shield non-autologous cells that produce soluble factors within a polymer matrix that prevents immune recognition and rejection.

Methods of Treatment, Methods of Preparing a Medicament

In yet another aspect of the present invention, methods of treatment and manufacture of a medicament are provided. Conditions alleviated or modulated by the administration of the present derivatives are those indicated above.

Dosages. For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing.

A subject in whom administration of HH or GLI or an antagonist thereto is an effective therapeutic regiment is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

Antibodies to GLI for Therapeutic or Diagnostic Use

According to the present invention, GLI, as produced by a recombinant source, or through chemical synthesis, or isolated from natural sources; and derivatives or analogs thereof, including fusion proteins, may be used as an immunogen to generate antibodies that recognize the GLI proteins, as exemplified below. Such antibodies include but are not limited to polyclonal, monoclonal, chimeric including humanized chimeric, single chain, Fab fragments, and a Fab expression library. The anti-GLI antibodies, for example, of the invention may be cross reactive, that is, they may recognize a GLI protein derived from a different source. Polyclonal antibodies have greater likelihood of cross reactivity. Alternatively, an antibody of the invention may be specific for a single form of GLI, such as the human GLI proteins, having the amino acid sequences of SEQ ID NOs: 16, 18 or 20, or a fragment of a human GLI protein.

Various procedures known in the art may be used for the production of polyclonal antibodies to GLI-or derivatives or analogs thereof. For the production of an antibody, various host animals can be immunized by injection with GLI, or a derivative (e.g., or fusion protein) thereof, including but not limited to rabbits, mice, rats, sheep, goats, etc. In one embodiment, GLI or a fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward GLI, or analog, or derivative thereof, any technique that provides for the production of antibody molecules by continuous cell lines in culture may be used. These include but are not limited to the hybridoma technique originally developed by Kohler and Milstein [*Nature*, 256:495-497 (1975)], as well as the trioma technique, the human B-cell hybridoma technique [Kozbor et al., *Immunology Today*, 4:72 (1983); Cote et al., *Proc. Natl. Acad. Sci. U.S.A.*, 80:2026-2030 (1983)], and the EBV-hybridoma technique to produce human monoclonal antibodies [Cole et al., in *Monoclonal Antibodies and Cancer Therapy*, Alan R. Liss, Inc., pp. 77-96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.*, 159:870 (1984); Neuberger et al., *Nature*, 312:604-608 (1984); Takeda et al., *Nature*, 314:452-454 (1985)] by splicing the genes from a mouse antibody molecule specific for GLI together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce e.g., GLI-specific single chain antibodies. An additional embodiment of the invention utilizes the techniques described for the construction of Fab expression libraries [Huse et al., *Science*, 246:1275-1281 (1989)] to allow rapid and easy identification of monoclonal Fab fragments with the desired specificity for a GLI, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of GLI, one may assay generated hybridomas for a product which binds to the GLI fragment containing such epitope and choose those which do not cross-react with GLI. For selection of an antibody specific to GLI from a particular source, one can select on the basis of positive binding with GLI expressed by or isolated from that specific source.

The foregoing antibodies can be used in methods known in the art relating to the localization and activity of the GLI, e.g., for Western blotting, imaging GLI in situ, measuring levels thereof in appropriate physiological samples, etc. using any of the detection techniques mentioned herein or known in the art. The standard techniques known in the art for immunoassays are described in "Methods in Immunodiagnosis", 2nd Edition, Rose and Bigazzi, eds. John Wiley & Sons, 1980; Campbell et al., "Methods and Immunology", W.A. Benjamin, Inc., 1964; and Oellerich, M. (1984) J. Clin. Chem. Clin. Biochem. 22:895-904.

In a specific embodiment, antibodies that agonize or antagonize the activity of GLI can be generated. Such antibodies can be tested using the assays described infra for identifying ligands.

One aspect of the invention provides a method of using an antibody against GLI to diagnose an invasive or aggressive form of cancer in a subject. Such antibodies may also be used therapeutically to inhibit the expression or activity of GLI. As GLI levels correlate with the invasiveness of a tumor as determined by the methods described herein, it provides a general bio marker for highly invasive tumors, and may be predictive of the invasiveness of other tumors that utilize the SHH-GLI signaling pathway. Thus, the antibody compositions and methods provided herein are particularly deemed useful for the diagnosis of invasive tumors including solid tumors such as lung tumors, as well as other tumors that utilize the SHH-GLI signaling pathway. More particularly, cancers that may be treated by the compositions and methods of the invention include, but are not limited to, Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma [squamous cell, undifferentiated small cell, undifferentiated large cell, adenocarcinoma], alveolar [bronchiolar] carcinoma, bronchial adenoma, sarcoma, lymphoma, chondromatous hamartoma, mesothelioma; Gastrointestinal: esophagus [squamous cell carcinoma, adenocarcinoma, leiomyosarcoma, lymphoma], stomach [carcinoma, lymphoma, leiomyosarcoma], pancreas [ductal adenocarcinoma, insulinoma, glucagonoma, gastrinoma, carcinoid tumors, VIPoma], small bowel [adenocarcinoma, lymphoma, carcinoid tumors, Kaposi's sarcoma, leiomyoma, hemangioma, lipoma, neurofibroma, fibroma], large bowel [adenocarcinoma, tubular adenoma, villous adenoma, hamartoma, leiomyoma]; Genitourinary tract: kidney [adenocarcinoma, Wilms tumor (nephroblastoma), lymphoma, leukemia], bladder and urethra [squamous cell carcinoma, transitional cell carcinoma, adenocarcinoma], prostate [adenocarcinoma, sarcoma], testis [seminoma, teratoma, embryonal carcinoma, teratocarcinoma, choriocarcinoma, sarcoma, Leydig cell tumor, fibroma, fibroadenoma, adenomatoid tumors, lipoma]; Liver: hepatocellular carcinoma, cholangiocarcinoma, hepatoblastoma, angiosarcoma, hepatocellular adenoma, hemangioma; Bone: osteogenic sarcoma [osteosarcoma], fibrosarcoma, malignant fibrous histiocytoma, chondrosarcoma, Ewing's sarcoma, malignant lymphoma [reticulum cell sarcoma], multiple myeloma, malignant giant cell tumor, chordoma, osteochondroma [osteocartilaginous exostoses], benign chondroma, chondroblastoma, chondromyxoid fibroma, osteoid osteoma and giant cell tumors; Nervous system: skull [osteoma, hemangioma, granuloma, xanthoma, Paget's disease of bone], meninges [meningioma, meningiosarcoma, gliomatosis], brain [astrocytoma, medulloblastoma, glioma, ependymoma, germinoma (pinealoma), glioblastoma multiforme, oligodendroglioma, schwannoma, retinoblastoma, congenital tumors], spinal cord [neurofibroma, meningioma, glioma, sarcoma]; Gynecological: uterus [endometrial carcinoma], cervix [cervical carcinoma, pre-invasive cervical dysplasia], ovaries [ovarian carcinoma (serous cystadenocarcinoma, mucinous cystadenocarcinoma, endometrioid carcinoma, clear cell adenocarcinoma, unclassified carcinoma), granulosa-theca cell tumors, Sertoli-Leydig cell tumors, dysgerminoma, malignant teratoma and other germ cell tumors], vulva [squamous cell carcinoma, intraepithelial carcinoma, adenocarcinoma, fibrosarcoma, melanoma], vagina [clear cell carcinoma, squamous cell carcinoma, sarcoma botryoides (embryonal rhabdomyosarcoma), fallopian tubes [carcinoma]; Hematologic: blood [myeloid leukemia (acute and chronic), acute lymphoblastic leukemia, chronic lymphocytic leukemia, myeloproliferative diseases, multiple myeloma, myelodysplastic syndrome], Hodgkin's disease, non-Hodgkin's lymphoma (malignant lymphoma); Skin: malignant melanoma, basal cell carcinoma, squamous cell carcinoma, Kaposi's sarcoma, nevi, dysplastic nevi, lipoma, angioma, dermatofibroma, keloids, psoriasis; and Adrenal glands: neuroblastoma.

The diagnostic method of the invention provides contacting a biological sample such as a biopsy sample, tissue, cell or fluid (e.g., whole blood, plasma, serum, or urine and cerebrospinal fluid) isolated from a subject with an antibody which binds GLI. The antibody is allowed to bind to the antigen to form an antibody-antigen complex. The conditions and time required to form the antibody-antigen complex may vary and are dependent on the biological sample being tested and the method of detection being used. Once non-specific interactions are removed by, for example, washing the sample, the antibody-antigen complex is detected using any one of the immunoassays described above as well a number of well-known immunoassays used to detect and/or quantitate antigens [see, for example, Harlow and Lane, Antibodies: A Laboratory Manual, Cold Spring Harbor Laboratory, New York (1988) 555-612]. Such well-known immunoassays include antibody capture assays, antigen capture assays, and two-antibody sandwich assays. In an antibody capture assay, the antigen is attached to solid support, and labeled antibody is allowed to bind. After washing, the assay is quantitated by measuring the amount of antibody retained on the solid support. In an antigen capture assay, the antibody is attached to a solid support, and labeled antigen is allowed to bind. The unbound proteins are removed by washing, and the assay is quantitated by measuring the amount of antigen that is bound. In a two-antibody sandwich assay, one antibody is bound to a solid support, and the antigen is allowed to bind to this first antibody. The assay is quantitated by measuring the amount of a labeled second antibody that binds to the antigen.

These immunoassays typically rely on labeled antigens, antibodies, or secondary reagents for detection. These proteins may be labeled with radioactive compounds, enzymes, biotin, or fluorochromes. Of these, radioactive labeling may be used for almost all types of assays. Enzyme-onjugated labels are particularly useful when radioactivity must be avoided or when quick results are needed. Biotin-coupled reagents usually are detected with labeled streptavidin. Streptavidin binds tightly and quickly to biotin and may be labeled with radioisotopes or enzymes. Fluorochromes, although requiring expensive equipment for their use, provide a very sensitive method of detection. Those of ordinary skill in the art will know of other suitable labels which may be employed in accordance with the present invention. The binding of these labels to antibodies or fragments thereof may be accomplished using standard techniques such as those described by Kennedy, et al. [(1976) Clin. Chim. Acta 70:1-31], and Schurs, et al. [(1977) Clin. Chim Acta 81:140].

In accordance with the diagnostic method of the invention, the presence or absence of the antibody-antigen complex is correlated with the presence or absence in the biological sample of the antigen, or a peptide fragment thereof. A biological sample containing elevated levels of said antigen is indicative of an invasive cancer in a subject from which the biological sample was obtained. Accordingly, the diagnostic method of the invention may be used as part of a routine screen in subjects suspected of having an invasive cancer or for subjects who may be predisposed to having an invasive cancer. Moreover, the diagnostic method of the invention may be used alone or in combination with other well-known diagnostic methods to confirm the presence of an invasive cancer.

The diagnostic method of the invention further provides that an antibody of the invention may be used to monitor the levels of GLI antigen in patient samples at various intervals of drug treatment to identify whether and to which degree the drug treatment is effective in reducing or inhibiting hyperproliferation of cells. Furthermore, antigen levels may be monitored using an antibody of the invention in studies evaluating efficacy of drug candidates in model systems and in clinical trials. The antigens provide for surrogate biomarkers in biological fluids to non-invasively assess the global status of tumor cell proliferation. For example, using an antibody of this invention, antigen levels may be monitored in biological samples of individuals treated with known or unknown therapeutic agents or toxins. This may be accomplished with cell lines in vitro or in model systems and clinical trials, depending on the cancer being investigated. Persistently increased total levels of GLI antigen in biological samples during or immediately after treatment with a drug candidate indicates that the drug candidate has little or no effect on cell proliferation. Likewise, the reduction in total levels of GLI antigen indicates that the drug candidate is effective in reducing or inhibiting tumor cell proliferation. This may provide valuable information at all stages of pre-clinical drug development, clinical drug trials as well as subsequent monitoring of patients undergoing drug treatment.

Antibody Labels

The GLI proteins of the present invention, antibodies to GLI proteins, nucleic acids that hybridize to SEQ ID NOs: 15, 17 or 19 (e.g. probes) etc. can all be labeled. Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^3H$, $^{14}C$, $^{32}P$, $^{35}S$, $^{36}Ci$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. Such labels may also be appropriate for the nucleic acid probes used in binding studies with GLI. In the instance where the label is an enzyme, detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. ultraviolet light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419-439 (1980) and in U.S. Pat. No. 4,857, 453.

Suitable enzymes include, but are not limited to, alkaline phosphatase and horseradish peroxidase.

In addition, GLI, a fragment thereof can be modified to contain a marker protein such as green fluorescent protein as described in U.S. Pat. No. 5,625,048 filed Apr. 29, 1997, WO 97/26333, published Jul. 24, 1997 and WO 99/64592 all of which are hereby incorporated by reference in their entireties.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459, 240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as [$^{35}S$]-methionine or [$^{32}P$]-orthophosphate. In addition to metabolic (or biosynthetic) labeling with [$^{35}S$]-methionine, the invention further contemplates labeling with [$^{14}C$]-amino acids and [$^3H$]-amino acids (with the tritium substituted at non-labile positions).

Therapeutic Uses of an Antibody That Blocks the SHH-GLI Pathway

Another aspect of the invention provides that an antibody, or a fragment thereof, which blocks signaling via the SHH-GLI pathway, may be administered to a human or other animal in an amount to decrease or inhibit cell proliferation, and tumorigenesis. As one may appreciate, any hyperproliferative disorder such as cancer, which may be diagnosed by an antibody of the invention, may also be treated using an antibody of the invention. A skilled clinician or physician would be able, by routine experimentation, to determine what an effective, non-toxic amount of antibody would be for the purpose of decreasing or inhibiting cell proliferation. Generally, however, an effective dosage will be in the range of about 0.05 to 100 milligrams per kilogram body weight per day.

Furthermore, an antibody of the invention may be administered to a human or other animal in a conventional dosage form prepared by combining an antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The antibodies of the present invention may also be used to target other chemotherapeutic agents to the site where needed. Alternatively, the antibodies can be used to target radioisotopes to the site where inhibtion of cellular proliferation is desirable. The antibodies may also be employed for diagnostic purposes to identify sites within the patient where the tumor burden is greatest. Furthermore, the antibodies may be used to assess the effectiveness of anti-tumor therapy for prognostic value.

The route of administration of an antibody, or fragment thereof, may be oral, parenteral, by inhalation or topical. The antibody may be delivered locally to the site of the cancer. The term parenteral as used herein includes intravenous, intramuscular, subcutaneous, rectal, vaginal or intraperitoneal administration. The subcutaneous and intramuscular forms of parenteral administration are generally preferred. The antibody may be delivered using a slow release formulation. It may be delivered in a liposome or a similar device.

The daily parenteral and oral dosage regimens for employing antibodies of the invention to therapeutically decrease cell proliferation will generally be in the range of about 0.05 to 100, but preferably about 0.5 to 10, milligrams per kilogram body weight per day.

An antibody of the invention may also be administered by inhalation. Inhalation, as used herein, includes intranasal and oral inhalation administration. Appropriate dosage forms for such administration, such as an aerosol formulation or a metered dose inhaler, may be prepared by conventional techniques. The preferred dosage amount of an antibody of the invention to be employed is generally within the range of about 10 to 100 milligrams.

An antibody of the invention may also be administered topically. By topical administration is meant non-systemic administration and includes the application of an antibody, or fragments thereof, externally to the epidermis, to the buccal cavity and instillation of such an antibody into the ear, eye and nose, and where it does not significantly enter the blood stream. In a particular topical formulation, the antibody may be effective in treatment of a hyperproliferative condition such as cancer. By systemic administration is meant oral, intravenous, intraperitoneal and intramuscular administration. The amount of an antibody required for therapeutic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

An alternate therapeutic approach for use of the antibodies of the present invention is via insertion of the gene encoding the antibody into a tumor cell whereby the intracellular expression of the antibody gene allows for modulation of the function of the protein for which the antibody is specific. Accordingly, this invention provides for methods and compositions for modulating SHH-GLI function in a cell involving intracellular expression of the antibody described herein. The invention is particularly applicable to inhibiting the SHH-GLI signaling in a cancer cell, thus inhibiting proliferation and survival of the cell.

To express an antibody homologue within a cell, a nucleic acid molecule encoding the antibody homologue, such as a recombinant expression vector encoding the antibody homologue, is introduced into the cell. Preferably, the antibody homologue used to modulate SHH-GLI signaling is a single chain Fv (scFv) fragment, although whole antibodies, or antigen binding fragments thereof (e.g., Fab fragments) may also be useful.

In a particularly preferred embodiment of the invention, an antibody homologue is expressed intracellularly in a cancerous mammalian cell to inhibit the cell proliferation function of SHH-GLI. The target cells of interest may be selected from any cell in which SHH-GLI plays a role in proliferation, such as cancer cells. A nucleic acid molecule encoding the antibody homologue can be introduced in vivo into cells of interest, by, for example, use of a recombinant viral vector or other vector system suitable for delivery of genes to cells in vivo.

To express an antibody homologue within a cell, a nucleic acid molecule(s) encoding the antibody homologue is prepared and introduced into the cell. An isolated nucleic acid molecule encoding an antibody homologue can be prepared according to standard molecular biology methods using nucleic acid sequences obtained from antibody genes. Isolated nucleic acid molecules encoding antibody chains (or relevant antigen binding portions thereof, such as $V_H$ or $V_L$ regions), specific for many different particular proteins have been described, and/or are available, in the art. Additionally, such nucleic acids can be isolated by standard techniques, for example, from a hybridoma that expresses a monoclonal antibody specific for a protein of interest, or by screening an immunoglobulin expression library (e.g., an immunoglobulin phage display library) with the protein of interest.

Monoclonal antibodies specific for an antigenic polypeptide of interest may be prepared, for example, using the technique of Kohler and Milstein, Eur. J. Immunol. 6:511-519, 1976, and improvements thereto. Briefly, these methods involve the preparation of immortal cell lines capable of producing antibodies having the desired specificity. Such cell lines may be produced, for example, from spleen cells obtained from an immunized animal. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction.

Alternatively, monoclonal antibodies can be prepared by constructing a recombinant immunoglobulin library, such as a scFv or Fab phage display library and nucleic acid encoding an antibody chain (or portion thereof) can be isolated therefrom. Immunoglobulin light chain and heavy chain first strand cDNAs can be prepared from mRNA derived from lymphocytes of a subject immunized with a protein of interest using primers specific for a constant region of the heavy chain and the constant region of each of the kappa and lambda light chains. Using primers specific for the variable and constant regions, the heavy and light chain cDNAs can then by amplified by PCR. The amplified DNA is then ligated into appropriate vectors for further manipulation in generating a library of display packages. Restriction endonuclease recognition sequences may also be incorporated into the primers to allow for the cloning of the amplified fragment into a vector in a predetermined reading frame for expression on the surface of the display package.

The immunoglobulin library is expressed by a population of display packages, preferably derived from filamentous phage, to form an antibody display library. In addition to commercially available kits for generating phage display libraries (e.g., the Pharmacia Recombinant Phage Antibody System, Catalog No. 27-9400-01; and the Stratagene SurfZAP™ Phage Display Kit, Catalog No. 240612), examples of methods and reagents particularly amenable for use in generating antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffiths et al. (1993) EMBO J 12:725-734; Hawkins et al. (1992) J Mol Biol 226:889-896; Clackson et al. (1991) Nature 352:624-628; Gram et al. (1992) Proc. Natl. Acad. Sci. USA 89:3576-3580; Garrad et al. (1991) Bio/Technology 2:1373-1377; Hoogenboom et al. (1991) Nuc Acid Res 19:4133-4137; and Barbas et al. (1991) Proc. Natl. Acad. Sci. USA 88:7978-7982. As generally described in McCafferty et al. Nature (1990) 348:552-554, complete VH and VL domains of an antibody, joined by a flexible (Gly$_4$-Ser)$_3$ linker, can be used to produce a single chain antibody expressed on the surface of a display package, such as a filamentous phage.

Once displayed on the surface of a display package (e.g., filamentous phage), the antibody library is screened with a protein of interest to identify and isolate packages that express an antibody that binds the protein of interest. Display packages expressing antibodies that bind immobilized protein can then be selected. Following screening and identification of a monoclonal antibody (e.g., a monoclonal scFv) specific for the protein of interest, nucleic acid encoding the selected antibody can be recovered from the display package (e.g., from the phage genome) by standard techniques. The nucleic acid so isolated can be further manipulated if desired (e.g., linked to other nucleic acid sequences) and subcloned into other expression vectors by standard recombinant DNA techniques.

Once isolated, nucleic acid molecules encoding antibody chains, or portions thereof, can be further manipulated using standard recombinant DNA techniques. For example, a single chain antibody gene can also be created by linking a VL coding region to a VH coding region via a nucleotide sequence encoding a flexible linker (e.g., (Gly$_4$-Ser)$_3$). Single chain antibodies can be engineered in accordance with the teachings of Bird et al. (1988) Science 242:423-426; Huston et al. (1988) Proc. Natl. Acad. Sci USA 85:5879-5883; Ladner, et al. International Publication Number WO 88/06630; and McCafferty, et al. International Publication No. WO 92/10147. A preferred single chain antibody for use in the invention blocks SHH-GLI signaling. A plasmid encoding a scFv antibody would be prepared using standard molecular biological techniques. Another manipulation that can be performed on isolated antibody genes is to link the antibody gene to a nucleotide sequence encoding an amino acid sequence that directs the antibody homologue to a particular intracellular compartment. A preferred nucleotide sequence to which an antibody gene is linked encodes a signal sequence (also referred to as a leader peptide). Signal sequences are art-recognized amino acid sequences that direct a protein containing the signal sequence at its amino-terminal end to the endoplasmic reticulum (ER). Typically, signal sequences comprise a number hydrophobic amino acid residues. Alternatively, an antibody homologue can be linked to an amino acid sequence that directs the antibody homologue to a different compartment of the cell. For example, a nuclear localization sequence (NLS) can be linked to the antibody homologue to direct the antibody homologue to the cell nucleus. Nuclear localization sequences are art-recognized targeting sequences. Typically, an NLS is composed of a number of basic amino acid residues.

Following isolation of antibody genes, as described above, and, if desired, further manipulation of the sequences, DNA encoding the antibody homologue can be inserted into an expression vector to facilitate transcription and translation of the antibody coding sequences in a host cell. Within the expression vector, the sequences encoding the antibody homologue are operatively linked to transcriptional and translational control sequences. These control sequences include promoters, enhancers and other expression control elements (e.g., polyadenylation signals). Such regulatory sequences are known to those skilled in the art and are described in Goeddel, Gene Expression Technology: Methods in Enzymology 185, Academic Press, San Diego, Calif. (1990). The expression vector and expression control sequences are chosen to be compatible with the host cell used. Expression vectors can be used to express one antibody chain (e.g., a single chain antibody) or two antibody chains (e.g., a Fab fragment). To express two antibody chains, typically the genes for both chains are inserted into the same expression vector but linked to separate control elements.

Expression of a nucleic acid in mammalian cells is accomplished using a mammalian expression vector. When used in mammalian cells, the expression vector's control functions are often provided by viral material. For example, commonly used promoters are derived from polyoma, Adenovirus 2, cytomegalovirus (CMV) and Simian Virus 40. An example of a suitable mammalian expression vector is pCDNA3 (commercially available from Invitrogen), which drives transcription via the CMV early intermediate promoter/enhancer and contains a neomycin resistance gene as a selective marker. Other examples of mammalian expression vectors include pCDM8 (Seed, B., (1987) Nature 329:840) and pMT2PC (Kaufman et al. (1987), EMBO J 6:187-195). Alternative to the use of constitutively active viral regulatory sequences, expression of an antibody homologue gene can be controlled by a tissue-specific regulatory element that directs expression of the nucleic acid preferentially in a particular cell type. Tissue-specific regulatory elements are known in the art.

In one embodiment, a recombinant expression vector of the invention is a plasmid vector. Plasmid DNA can be introduced into cells by a variety of techniques either as naked DNA or, more commonly, as DNA complexed with or combined with another substance. Alternatively, in another embodiment, the recombinant expression vector of the invention is a virus, or portion thereof, which allows for expression of a nucleic acid introduced into the viral nucleic acid. For example, replication defective retroviruses, adenoviruses and adeno-associated viruses can be used for recombinant expression of antibody homologue genes. Virally-mediated gene transfer into cells can be accomplished by infecting the target cell with the viral vector.

Non-limiting examples of techniques which can be used to introduce an expression vector encoding an antibody homologue into a host cell include:

Adenovirus-Polylysine DNA Complexes: Naked DNA can be introduced into cells by complexing the DNA to a cation, such as polylysine, which is then coupled to the exterior of an adenovirus virion (e.g., through an antibody bridge, wherein the antibody is specific for the adenovirus molecule and the polylysine is covalently coupled to the antibody) (see Curiel, D. T., et al. (1992) Human Gene Therapy 3:147-154). Entry of the DNA into cells exploits the viral entry function, including natural disruption of endosomes to allow release of the DNA intracellularly. A particularly advantageous feature of this approach is the flexibility in the size and design of heterologous DNA that can be transferred to cells.

Receptor-Mediated DNA Uptake: Naked DNA can also be introduced into cells by complexing the DNA to a cation, such as polylysine, which is coupled to a ligand for a cell-surface receptor (see for example Wu, G. and Wu, C. H. (1988) J. Biol. Chem. 263:14621; Wilson et al. (1992) J Biol. Chem. 267:963-967; and U.S. Pat. No. 5,166,320). Binding of the DNA-ligand complex to the receptor facilitates uptake of the DNA by receptor-mediated endocytosis. Receptors to which a DNA-ligand complex have targeted include the transferrin receptor and the asialoglycoprotein receptor. Additionally, a DNA-ligand complex can be linked to adenovirus capsids which naturally disrupt endosomes, thereby promoting release of the DNA material into the cytoplasm and avoiding degradation of the complex by intracellular lysosomes (see for example Curiel et al. (1991) Proc. Natl. Acad. Sci. USA 88:8850; and Cotten, M. et al. (1992) Proc. Natl. Acad. Sci. USA 89:6094-6098; Wagner, E. et al. (1992) Proc. Natl. Acad. Sci. USA 89:6099-6103). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Liposome-Mediated transfection ("lipofection"): Naked DNA can be introduced into cells by mixing the DNA with a liposome suspension containing cationic lipids. The DNA/liposome complex is then incubated with cells. Liposome mediated transfection can be used to stably (or transiently) transfect cells in culture in vitro. Protocols can be found in Current Protocols in Molecular Biology, Ausubel, F. M. et al. (eds.) Greene Publishing Associates, (1989), Section 9.4 and other standard laboratory manuals. Additionally, gene delivery in vivo has been accomplished using liposomes. See for example Nicolau et al. (1987) Meth. Enz. 149:157-176; Wang and Huang (1987) Proc. Natl. Acad. Sci. USA 84:7851-7855; Brigham et al. (1989) Am. J Med. Sci. 298:278; and Gould-Fogerite et al. (1989) Gene 84:429-438.

Direct Injection: Naked DNA can be introduced into cells by directly injecting the DNA into the cells. For an in vitro culture of cells, DNA can be introduced by microinjection, although this not practical for large numbers of cells. Direct injection has also been used to introduce naked DNA into cells in vivo (see e.g., Acsadi et al. (1991) Nature 332:815-818; Wolff et al. (1990) Science 247:1465-1468). A delivery apparatus (e.g., a "gene gun") for injecting DNA into cells in vivo can be used. Such an apparatus is commercially available (e.g., from BioRad).

Retroviral Mediated Gene Transfer: Defective retroviruses are well characterized for use in gene transfer for gene therapy purposes (for a review see Miller, A. D. (1990) Blood 76:271). A recombinant retrovirus can be constructed having a nucleic acid encoding a gene of interest (e.g., an antibody homologue) inserted into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art.

Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Furthermore, if the inhibitory molecule specific for GLI is an antisense nucleic acid or a small interfering RNA molecule (siRNA), the vectors may be selected from a retrovirus such as for example, a human immunodeficiency virus type 1-derived lentivirus vector. While any retrovirus may be utilized, the lentivirus approach allows for delivery to a broad variety of cellular targets, both ex vivo (cell lines, primary cells including stem cells, fertilized oocytes, and blastocysts) and in vivo (e.g., brain, lung, liver). The lentivirus vector-mediated delivery of siRNAs allows for the controllable suppression of cellular genes both with a high degree of efficacy and without significant leakiness.

Adenoviral Mediated Gene Transfer: The genome of an adenovirus can be manipulated such that it encodes and expresses a gene product of interest (e.g., an antibody homologue) but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl.

Acad. Sci. USA 89:6482-6486), hepatocytes (Herz and Gerard (1993) Proc. Natl. Acad. Sci. USA 90:2812-2816) and muscle cells (Quantin et al. (1992) Proc. Natl. Acad. Sci. USA 89:2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to many other gene delivery vectors (Berkner et al. cited supra; Haj-Ahmand and Graham (1986) J Virol. 57:267). Most replication-defective adenoviral vectors currently in use are deleted for all or parts of the viral E1 and E3 genes but retain as much as 80% of the adenoviral genetic material.

Adeno-Associated Viral Mediated Gene Transfer: Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol. (1992) 158:97-129). It is also one of the few viruses that may integrate its DNA into non-dividing cells, and exhibits a high frequency of stable integration (see for example Flotte et al. (1992) Am. J Respir. Cell. Mol. Biol. 7:349-356; Samulski et al. (1989) J Virol. 63:3822-3828; and McLaughlin et al. (1989) J Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J Virol. 51:611-619; and Flotte et al. (1993) J Biol. Chem. 268:3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of the introduced DNA can be detected, for example, by Northern blotting, RNase protection or reverse transcriptase-polymerase chain reaction (RT-PCR). Expression of the introduced gene product (e.g., the antibody homologue) in the cell can be detected by an appropriate assay for detecting proteins, for example by immunohistochemistry.

As will be appreciated by those skilled in the art, the choice of expression vector system will depend, at least in part, on the host cell targeted for introduction of the nucleic acid. For example, nucleic acid encoding an antibody homologue which blocks SHH-GLI signaling is preferably introduced into tumor cells showing enhanced proliferative capacity and highly invasive characteristics. Tumor cells that are responsive to treatment with the blocking antibodies of the present invention include prostate cancer, lung cancer (small cell and non small cell lung cancer), basal cell carcinoma, melanoma, glioblastoma, medulloblastoma, PNETs, other brian tumors, stomach, GI tract including colon, pancreas, rhabdomyosarcomas, and soft tissue sarcomas. Preferred expression vectors and delivery systems for introducing nucleic acid into malignant cells include transfection with adenoviral-polylysine DNA complexes and adenoviral vector-mediated gene transfer. These delivery systems are suitable for introduction of nucleic acid into cells in vitro, or more preferably for tumor cells, in vivo.

The functional outcome of intracellular antibody expression, on the subsequent expression and/or function of the protein targeted for antibody binding (referred to as the target protein,) can be assessed by suitable assays that monitor the expression and/or function of the target protein, including standard immunohistochemistry or immunoelectron microscopy techniques.

Alternatively, cell proliferation can be measured using commercially available cell proliferation assays. The functional outcome of intracellular antibody homologue expression targeting SHH-GLI on tumor cell growth and survival, or on the expansion of immunocompetent cells with unwanted specificity in a mammal can be assessed in vivo using animal model systems that may be predictive of therapeutic efficacy in humans. For example, the antibody genes may be inserted into a human cancer cell known to have the SHH-GLI signaling pathway. These cells may be implanted into athymic nude mice, and tumor growth may be monitored visually over time.

Other Diagnostic Means of Determining Levels of Gli

Cell-based Reporters and Instrumentation

Cellular screening techniques can be broadly classified into two groups: semi-biochemical approaches that involve the analysis of cell lysates, or live cell assays. Whole cell assay methodologies vary with respect to assay principle, but have largely in common a form of luminescence or fluorescence for detection. Luminescence is a phenomenon in which energy is specifically channeled to a molecule to produce an excited state. Luminescence includes fluorescence, phosphorescence, chemiluminescence and bioluminescence.

An ever-increasing list of fluorescent proteins include the widely-used GFP derived from Aequorea Victoria and spectral variants thereof. The list includes a variety of fluorescent proteins derived from other marine organisms; bacteria; fungi; algae; dinoflagellates; and certain terrestrial species. These reporters have the advantage of not requiring any exogenous substrates or co-factors for the generation of a signal but do require an external source of radiation for excitation of the intrinsic fluorophore. In addition, the increasing availability of genes encoding a broad spectrum of fluorescent reporter proteins enables the construction of assays tailored for specific applications, cell types, and detection systems.

Different classes of luminescent proteins, luciferases, have been have been discovered in bacteria and eukaryotes. Luciferases are proteins that catalyze the conversion of a natural substrate into a product that emits light in the visible spectrum and thus require no external radiation source. Monomeric forms of luciferase have been cloned from firefly, Renilla, and other organisms. Firefly luciferase is the most common of the bioluminescent reporters and is a 61 kDa monomeric enzyme that catalyzes a two-step oxidation reaction to yield light. Renilla luciferase is a 31 kDa monomeric enzyme that catalyzes the oxidation of coelenterazine to yield coelenteramide and blue light of 480 nm. Substrates for luciferase are widely available from commercial suppliers such as Promega Corporation and Invitrogen Molecular Probes.

A variety of useful enzymatic reporters are enzymes that either generate a fluorescent signal or are capable of binding small molecules that can be tagged with a fluorescent moiety to serve as a fluorescent probe. For example, dihydrofolate reductase (DHFR) is capable of binding methotrexate with high affinity; a methotrexate-fluorophore conjugate can serve as a quantitative fluorescent reagent for the measurement of the amount of DHFR within a cell. By tagging methotrexate with any of a number of fluorescent molecules such as fluorescein, rhodamine, Texas Red, BODIPY and other commercially available molecules (such as those available from Molecular Probes/Invitrogen and other suppliers) a range variety of fluorescent readouts can be generated. The wide range of techniques of immunohistochemistry and immunocytochemistry can be applied to whole cells. For example, ligands and other probes can be tagged directly with fluorescein or another fluorophore for detection of binding to cellular proteins; or can be tagged with enzymes such as alkaline phosphatase or horseradish peroxidase to enable indirect detection and localization of signal.

Many other enzymes can be used to generate a fluorescent signal in live cells by using specific, cell-permeable substrate that either becomes fluorescent or shifts its fluorescence spectrum upon enzymatic cleavage. For example, substrates for beta-lactamase exist whose fluorescence emission properties change in a measurable way upon cleavage of a beta-lactam core moiety to which fluorophores are attached. Changes include, shifts in fluorophore absorption or emission wavelengths, or cleavage of a covalent assembly of emmision-absorption-mathched fluorophore pairs that in the covalently-assembled form sustain resonance energy transfer between the two fluorophores that is lost when the two are separated. Membrane-permeant, fluorescent BLA substrates such as the widely-used CCF2/AM allow the measurement of gene expression in live mammalian cells in the absence or presence of compounds from a biologically active chemical library.

Luminescent, fluorescent or bioluminescent signals are easily detected and quantified with any one of a variety of automated and/or high-throughput instrumentation systems including fluorescence multi-well plate readers, fluorescence activated cell sorters (FACS) and automated cell-based imaging systems that provide spatial resolution of the signal. A variety of instrumentation systems have been developed to automate HCS including the automated fluorescence imaging and automated microscopy systems developed by Cellomics, Amersham, TTP, Q3DM, Evotec, Universal Imaging and Zeiss. Fluorescence recovery after photobleaching (FRAP) and time lapse fluorescence microscopy have also been used to study protein mobility in living cells. Although the optical instrumentation and hardware have advanced to the point that any bioluminescent signal can be detected with high sensitivity and high throughput, the existing assay choices are limited either with respect to their range of application, format, biological relevance, or ease of use.

Transcriptional Reporter Assays

Cell-based reporters are often used to construct transcriptional reporter assays, which allow monitoring of the cellular events associated with signal transduction and gene expression. Reporter gene assays couple the biological activity of a target to the expression of a readily detected enzyme or protein reporter. Based upon the fusion of transcriptional control elements to a variety of reporter genes, these systems "report" the effects of a cascade of signaling events on gene expression inside cells. Synthetic repeats of a particular response element can be inserted upstream of the reporter gene to regulate its expression in response to signaling molecules generated by activation of a specific pathway in a live cell. The variety of transcriptional reporter genes and their application is very broad and includes drug screening systems based on beta-galactosidase (beta-gal), luciferase, alkaline phosphatase (luminescent assay), GFP, aequorin, and a variety of newer bioluminescent or fluorescent reporters.

In general, transcription reporter assays have the capacity to provide information on the response of a pathway to natural or synthetic chemical agents on one or more biochemical pathways, however they only indirectly measure the effect of an agent on a pathway by measuring the consequence of pathway activation or inhibition, and not the site of action of the compound. For this reason, mammalian cell-based methods have been sought to directly quantitate protein-protein interactions that comprise the functional elements of cellular biochemical pathways and to develop assays for drug discovery based on these pathways.

Cellular Assays for Individual Proteins Tagged with Fluorophores or Luminophores.

Subcellular compartmentalization of signaling proteins is an important phenomenon not only in defining how a biochemical pathway is activated but also in influencing the desired physiological consequence of pathway activation. This aspect of drug discovery has seen a major advance as a result of the cloning and availability of a variety of intrinsically fluorescent proteins with distinct molecular properties.

High-content (also known as high-context) screening (HCS) is a live cell assay approach that relies upon image-based analysis of cells to detect the subcellular location and redistribution of proteins in response to stimuli or inhibitors of cellular processes. Fluorescent probes can be used in HCS; for example, receptor internalization can be measured using a fluorescently-labeled ligand that binds to the transferrin receptor. Often, individual proteins are either expressed as fusion proteins, where the protein of interest is fused to a detectable moiety such as GFP, or are detected by immunocytochemistry after fixation, such as by the use of an antibody conjugated to Cy3 or another suitable dye. In this way, the subcellular location of a protein can be imaged and tracked in real time. One of the largest areas of development is in applications of GFP color-shifted mutants and other more recently isolated new fluorescent proteins, which allow the development of increasingly advanced live cell assays such as multicolor assays. A range of GFP assays have been developed to analyze key intracellular signaling pathways by following the redistribution of GFP fusion proteins in live cells. For drug screening by HCS the objective is to identify therapeutic compounds that block disease pathways by inhibiting the movement of key signaling proteins to their site of action within the cell.

Tagging a protein with a fluorophore or a luminophore enables tracking of that particular protein in response to cell stimuli or inhibitors. For example, the activation of cell signaling by TNF can be detected by expressing the p65 subunit of the NFkB transcription complex as a GFP fusion and then following the redistribution of fluorescence from the cytosolic compartment to the nuclear compartment of the cell within minutes after TNF stimulation of live cells (J A Schmid et al., 2000, Dynamics of NFkB and IkBa studied with green fluorescent protein (GFP) fusion proteins, J. Biol. Chem. 275: 17035-17042). What has been unique about these approaches is the ability to allow monitoring of the dynamics of individual protein movements in living cells, thus addressing both the spatial and temporal aspects of signaling.

Specific Embodiments

As shown below the inventors have not only examined the role of GLI proteins in carcinogenesis, in particular lung, but have explored the effects of Gli1 on apoptosis induced by various chemotherapeutic agents. The inventors have provided evidence to support a role for GLI in tumorigenesis and more importantly from a clinical point of view, in resistance to cell killing by cancer chemotherapeutic agents.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

SHH-GLI Signaling and Tumorigenesis

Animals

Swiss-Webster mice were used unless otherwise specified. The Shh (Chiang et al., (1996) Nature 383, 407-413), Gli1 (Park et al., (2000) Development 127, 1593-1605) and Gli2 (Mo et al., (1997) Development 124, 113-123.) mutants from our colony were in this background. Cortical explants were prepared as previously described (Dahmane et al., (2001) Development 128, 5201-5212) and treated for 48 h. Anti-SHH antibodies were used at 4 µg/ml (University of Iowa Hybridoma Bank). Octyl-modified SHH-N protein was a kind gift from Ontogeny/Curis Inc. Human tumor samples were derived from the operating room or from the NYU tumor banks. Brain tumor cell lines were obtained from ATCC and grown according to its specifications. GL261 was a kind gift of Dr D. Zagzag. Frog (*Xenopus laevis*) embryos were obtained, reared and staged by standard methods. Tadpoles were ~2 days old. All statistical analyses were carried out using the Student's t test and deviations are shown as s.e.m.

In Vivo Cyclopainine Treatment

Cyclopamine (Toronto Research Biochemicals) was used at 1 mg/ml conjugated with 2-Hydropropyl-β-Cyclodextrin (HBC (Sigma); prepared as a 45% solution in PBS). Five to ten week-old inbred C57B16/j mice were injected intraperitoneally for one week with HBC alone as control or cyc at 10 mg/kg/day. The day following the last injection, the mice were pulsed for 2 h with BrdU (20 mg/kg, IP injection). Immunofluorescence of cryostat sections was as described (Dahmane et al., (2001 Development 128, 5201-5212). The stainings were digitally recorded using a cooled CCD camera-equiped Axiophot (Zeiss) and the BrdU$^+$/DAPI$^+$ nuclei counted within the lateral wall of the lateral ventricles. For the in vivo treatment followed by the preparation of nsps, pregnant mothers (E12.5) or P4 pups were injected for 5 days with HBC alone or cyc at 10 mg/kg/day and cortical nsp from E17.5 embryos or SVZ nsp from P9 animals were made, respectively.

Cell Culture and siRNAs Transfections

U87 glioblastoma cells were cultured in MEM with 10% fetal bovine serum (FBS), and glioblastoma primary cultures were cultured in DMEM/F12 with 10% FBS. For transfection of siRNAs, cells were plated the day before the treatment in p16 well plates, at a 70% cell density. 24 h later cells were transfected using the Oligofectamine reagent from Gibco (cat#12252-011) following the specifications of the manufacturer. The final concentration of siRNA was 200 nM. Three hours after, the transfection media was changed to normal growing media (10% FBS) and the cells were kept growing for another 48 h (or 24 h where indicated) before processing. The following sequences were used for the siRNA experiments:

| | | | |
|---|---|---|---|
| human | GLI1 | AACTCCACAGGCATACAGGAT | (SEQ ID NO: 21) |
| human/mouse | GLI2 | AAGATCTGGACAGGGATGACT | (SEQ ID NO: 22) |
| mouse | GLI2 | AATGATCTCTGCCGCCAGGGG | (SEQ ID NO: 23) |
| human/mouse | GLI3 | AATGAGGATGAAAGTCCTGGA | (SEQ ID NO: 24) |

Proliferation Assay

BrdU (6 kg/ml) incorporation was done for 2 h in U87 glioblastoma cells and for 14 h in the primary glioblastoma cells. After that the cells were fixed for 5 minutes in paraformaldehide (PFA) 4%. Inmunocytochemistry was performed with an anti-BrdU antibody (Becton-Dickinson) and fluorescein-conjugated secondary antibodies (Boehringer Mannheim). The measurement was done by counting percentage of BrdU positive cells per field, counting at least 8 fields per point.

Explants, Dissociated Cells, Cell Treatments and Chemicals

Neocortical or tectal explants from embryonic day (E) 17.5 to postnatal-day (P) 3 mice were taken from the parietal region, or adjacent to the dorsal midline in the prospective superior and inferior colliculi, respectively. After removal of the meninges, the explants were grown on floating filters in serum-free media. After 12 hours in culture, SHH was added and incubation continued for a further 48 hours. Explants for RNA preparation were directly collected in Trizol (Gibco-BRL). For dissociated cells, parietal cortical pieces of P3 brains were pooled (~10 explants per experiment) and treated with trypsin for 10 minutes (0.25 mg/ml at room temperature). Tissue was triturated manually in DNase (0.5 mg/ml), and cells were centrifuged, resuspended in supplemented serum-free media and plated at a density of ~400 cells/mm$^2$ in poly-L-lysine-coated 16- or 8-well slides. After 12 hours the media were replaced and SHH protein added if required. Cells were cultured for a further 48 hours and processed for immunocytochemistry after fixation in 4% paraformaldehyde for 1 minute. Primary gliomas from the operating room were dissociated with papain and plated in U118 media containing 10% fetal calf serum (FCS) or in DMEM:F12 serum-free media supplemented with BIT-9500 (Stem Cell Technologies) and 20 ng/ml of each of FGF2, EGF and PDGF. After two to three passages, the cells had a homogenous appearance and were then tested. Recombinant N-SHH was a kind gift from Ontogeny and was used at 5 nM. For blocking experiments, anti-SHH mAb 5E1 was used at 20 Ag/ml (obtained from the University of Iowa Hybridoma Bank). Cyclopamine (a kind gift from the Poisonous Plant Laboratory or purchased from Toronto Research Chemicals) was used at 0.5-5 µM for 48 hours before assaying. Cell lines were plated at 60% confluency the night before cyclopamine treatment. FK and ddFK (Sigma) were used at 50 µM.

Microinjection, RNAs and Antisense Oligonucleotides

Injection of synthetic RNAs into frog embryos was performed into one cell at the two-cell stage, targeting the future CNS and epidermis. Frog or human Gli1 RNAs were injected at 2 ng/10 nl/embryo. The N-terminal Myc-epitope tag in the frog Gli1 and Gli2 proteins was used to monitor protein distribution. lacZ RNA was co-injected at 0.2 ng/10 nl/embryo and was used as a lineage tracer through X-gal staining, yielding an insoluble blue precipitate. Morpholino antisense oligonucleotides were purchased from Gene Tools and used at 0.5 mM. These were frog Gli1, 5'CGGGCGGACACTG-GCGGGACGC3' (SEQ ID NO: 33); frog Gli2, 5'GCACA-GAACGCAGGTAATGCTCCAT3' (SEQ ID NO: 25); and frog Shh, 5'GAGATTCGAGTTCGCAACCAGCATC3' (Seq ID NO: 26). In all cases, the oligonucleotides were designed to be complementary to regions near the initiation ATG codon and are predicted to inhibit translation.

RT-PCR and In Situ Hybridization

In situ hybridization on serial ~20 μm cryostat sections with digoxigenin-labeled antisense RNA probes and full-length frog, mouse or human Gli1 cDNA clones and histology were as previously described (Dahmane et al. (1997), Nature 389:876-881). Visualization of the low levels of GLI1 and PTCH1 expression in CNS tumors and mouse brains older than E17 required long (2 days at room temperature) chromogenic development of the in situ hybridization reactions. Specificity was confirmed using sense RNA probes. RT-PCR of human tumors or cell lines was performed for 27, 32 and 37 cycles to determine the linear amplification range. PCR primers and specific reaction conditions are available upon request. A probe for DDR1 was made as described (Weiner et al. (2000), Neurosurgery 47: 1400-1409). A 0.6 kb RT-PCR clone was used as a template for probe production for mouse Pdgfrα (platelet-derived growth factor receptor α).

Immunocytochemistry

BrdU incorporation in explants and dissociated cells was for 2 hours at 6 μg/ml. Primary tumor cultures were labelled with BrdU for 14 hours. Pregnant mice were injected intraperitoneally with a single dose of 50 μl of 10 mg/ml BrdU and embryos dissected 2 hours afterwards. For tadpoles, one 20 nl injection of 10 mg/ml BrdU into the lumen of the CNS and one into the endoderm were performed 1 hour before fixation. Sections of embryos or explants (14-20 μm) were prepared using a cryostat. Immunocytochemistry with monoclonal anti-BrdU antibody (Becton-Dickinson), monoclonal anti-vimentin antibody (Santa Cruz), monoclonal anti-neuronal tubulin Tuj1 antibody (Babco), rat monoclonal anti-Nestin antibody (University of Iowa Hybridoma Bank) or O4 monoclonal antibody (Chemicon, also a kind gift of Bob Miller) was performed on frozen sections and cells using fluorescein-conjugated secondary antibodies (Boehringer Mannheim).

GLI Gene Expression in Primary Brain Tumors and Brain Tumor Cell Lines

Our findings in normal development raise the possibility that inappropriate activation or maintenance of the SHH-GLI pathway could lead to hyperproliferation, the basis of tumorigenesis. To test this idea, sporadic human brain tumors were analyzed for the consistent expression of the GLI genes. We tested by RT-PCR seven glial tumors and primitive neuroectodermal tumors (PNETs), including those from the cerebellum (medulloblastomas), because the latter have been shown previously to harbor PTCH1 mutations, suggesting the activation of the SHH-GLI pathway. We found that all the tumors tested expressed GLI1, although at different levels (data not shown). Additional analyses for a total of 22 tumors showed that all samples contained the three GLI transcripts. Expression of PTCH1 followed the expression of GLI1/2, while that of SHH was not consistently detected.

In situ hybridization analyses of 22 independent brain tumors showed that GLI1 was expressed in neuronal and in glial tumors, including glioblastoma multiforme and low grade glioma. GLI1 and PTCH1 mRNAs were detected in the regions containing tumor cells and not in surrounding normal tissues.

Analyses of human brain tumor cell lines, including seven glioblastoma (U87MG, U118MG, U138MG, A172, T98G, M059K, M059J), two glioma (Hs683, mouse GL261), one neuroglioma (H4), three astrocytoma (CCF-STTG1, SW 1088, SW 1783), three medulloblastoma (Daoy, D283, D341) and two neuroblastoma (SK-N-AS, IMR32) lines, showed that all brain tumor cell lines co-expressed GLI1, GLI2 and PTCH1. GLI3 was expressed by all but one (D341) and only a subset (U87MG, U138MG, Daoy, M059K, SW1783) expressed SHH (not shown).

As a control, a panel of unrelated sporadic human tumors was also tested by RT-PCR and found that GLI1 was expressed consistently in prostate carcinomas (9/11 cases) but not in those from the breast (1/7), suggesting that prostate cancer may also result from deregulated SHH-GLI signaling.

Cyclopamine Modulates the Proliferation of a Subset of Brain Tumor Cells

Expression of the GLI and PTCH1 by glioma cells raised the possibility that these harbor mutations that activate the pathway at different levels. Indeed, we expected that only a fraction of these possible mutations would affect the PTCH-SMO receptor complex. To address this possibility we have tested the effects of cyclopamine, a drug that inhibits the function of oncogenic Smoothened forms. The glioblastoma/glioma lines U87, U118, U138, M059K, Hs683, C6, GL261, astrocytoma lines, SW1088 and SW1783, and the medulloblastoma line Daoy were tested and four responded to cyclopamine treatment by decreasing BrdU incorporation by ~25-50%. These are the glioma lines U87, U118 and U138, and the medulloblastoma line Daoy: untreated U87, $22.5\pm1.4\%$ BrdU-positive cells/field; $0.5$ μM cyclopamine treated, $16.5\pm0.9\%$ BrdU-positive cells/field, $P<0.005$; and 5 μM cyclopamine-treated, $13.2\pm1.2\%$ BrdU-positive cells/field, $P<0.001$; untreated U118, $12.9\pm1.3\%$ BrdU-positive cells/field; $0.5$ μM cyclopamine treated, $6.7\pm0.8\%$ BrdU-positive cells/field, $P=0.001$; and 5 μM cyclopamine treated, $7.1\pm1.1\%$ BrdU-positive cells/field, $P<0.005$; untreated U138, $13.3\pm0.7\%$ BrdU-positive cells/field; $0.5$ μM cyclopamine treated, $9.5\pm0.6\%$ BrdU-positive cells/field, $P<0.005$; and 5 μM cyclopamine-treated, $7.5\pm1.2\%$ BrdU-positive cells/field, $P=0.001$; untreated Daoy, $37.9\pm2\%$ BrdU-positive cells/field; $0.5$ μM cyclopamine treated, $27.7\pm1.5\%$ BrdU-positive cells/field, $P=0.001$; and 5 μM cyclopamine-treated, $27.1\pm1.7\%$ BrdU-positive cells/field, $P=0.001$. While it is unclear why these four lines respond differently, these results show that their proliferation is modulated by cyclopamine-sensitive targets. Non-responsive cells could have mutations that affect the activation of the pathway downstream of the receptor complex.

Cyclopamine was also tested in three primary cortical gliomas that were dissociated and cultured in vitro. Dividing cells from all three tumors expressed vimentin (not shown), which marks neural precursors in culture among other cell types. These cells also expressed GLI1 and GLI2 but not Shh. Treatment with 5 μM cyclopamine resulted in the inhibition of BrdU incorporation in one of them by 60% (untreated tumor 3, $11.4\pm1.5\%$ BrdU-positive cells/field; cyclopamine treated, $3.6\pm0.5\%$ BrdU-positive cells/field, $P<0.001$), while the other two were unresponsive (untreated tumor 4, $4.5\pm0.5\%$ BrdU-positive cells/field; treated, $4.6\pm0.5\%$ BrdU-positive cells/field, P>0.9; and untreated tumor 5, 2.4±0.7% BrdU-positive cells/field; treated, 3.2±0.3% BrdU-positive cells/field, P=0.3).

Deregulated GLI1 Function is Sufficient to Induce Hyperproliferation of CNS Cells with Precursor Character The results with brain tumors and cell lines suggest that the deregulated SHH-GLI pathway may be involved in abnormal proliferation. To directly test this idea, we have misexpressed Gli1 in the CNS of the developing frog embryo. Tadpoles expressing Gli1 after unilateral injections developed ipsilateral neural tube hyperplasias (24/36 embryos), first detected at tailbud stages, that expressed the β-gal lineage tracer (15/15 embryos). Most hyperplasias appeared in the hindbrain and spinal cord, consistent with the more frequent distribution of the injected materials in these areas, and showed an increase in the number of BrdU-positive cells (more than fivefold: 19±1 BrdU-positive cells on average per control neural tube side in three sections counted of independent control embryos and 91±5.6 BrdU-positive cells per injected neural tube side in three sections of independent Gli1-injected tadpoles; P<0.005) when compared with the normal, uninjected contralateral side where BrdU-positive cells were confined to the vz zone. As expected, abnormal tissue contained HNF-3β-positive floor plate cells and neurons but a large proportion of the hyperplastic masses had an undifferentiated appearance. In cases where the injected Gli1 RNA localized to the epidermis, the resulting skin hyperplasias or BCC-like tumors also showed a marked increase in the number of BrdU-positive cells (not shown) over that seen in the normal, contralateral epidermis. Gli2 or Gli3 did not have these effects because they induced ectopic mesoderm earlier).

The expression of Gli1 in glial tumors, together with the involvement of the SHH-GLI pathway in the development of glial lineages, raised the possibility that Gli1-induced hyperplasias could contain glial precursors. Pdgfrα labels oligodendrocyte and other precursors) and is a marker of gliomas). In tadpoles, Pdgfrα is first expressed within the CNS in a small group of bilateral cells of the central vz of the diencephalon, overlapping Gli1 expression (not shown). Gli1-injected tadpoles showed ectopic expression of Pdgfrα within the hyperplasias 20/45). Control uninjected tadpoles (0/60) failed to show ectopic expression of Pdgfrα.

To test if these hyperplasias include precursor cells with vz character, we have used the expression of endogenous Gli1 as a marker, as this gene is only transiently expressed in vz cells in normal development. Sectioning human GLI1 RNA-injected embryos after in situ hybridization with a frog Gli1 probe (which does not cross-hybridize with the injected, exogenous human RNA under the conditions used) showed that the majority (12/16 embryos) had unilateral hyperplasias ectopically expressing endogenous Gli1.

Activation of Endogenous Gli1 Function is Required for Hyperproliferation

The expression of endogenous GLI1 in tumors and in induced tadpole hyperplasias raised the possibility that its function is required in tumor formation. This could be consistent with the observation that abnormal growths in the CNS or epidermis were first detected towards the late neurula-early tailbud stages, when most of the injected material had already been degraded. To test if endogenous Gli1 is required for tumor development, we injected human GLI1 RNA along with a morpholino antisense oligonucleotide specific for the endogenous frog Gli1 mRNA that does not recognize the injected human GLI1 RNA. Injection of human GLI1 and lacZ RNAs resulted in the development of both CNS and skin hyperplasias (35/36). By contrast, co-injection of these same RNAs plus morpholino anti-frog Gli1 resulted in normal development without tumor formation. This effect is specific, as morpholino anti-frog Gli2 (n=47/52), morpholino anti-frog Shh (n=48/50) or a control unrelated morpholino (n=49/49) did not prevent tumor development by co-injected human GLI1 (not shown).

Summary of Results

The results showed that both the U87 glioblastoma cells, as well as the primary glioblastoma cells, when transfected with small inhibitory RNA molecules specific for Gli1, showed significant inhibition in proliferative capacity, as compared to control cells.

Shh-producing cells are located in the neocortical and tectal plates, in the dentate gyrus, in the Purkinje (PL) layer and at the lower levels in germinative zones. Responding cells are located in the ventricular/subventricular zones (VZ/SVZ) of the neocortex and tectum, in the external germinal layer (EGL) of the cerebellum and the subgranular layer of the hippocampus.

FIG. 1 shows the SHH-GLI pathway and the potential sites for therapeutic agents blocking its activity. Inhibitors of the pathway with potential therapeutic value include agents that inhibit the action of SMO (Smoothened) in the receptor complex, such as plant alkaloid cyclopamine, agents that inhibit specific aspects of the transduction of the signal, including the nuclear inport or activation of Gli proteins, and agents that specifically inhibit Gli function.

Figure 2:
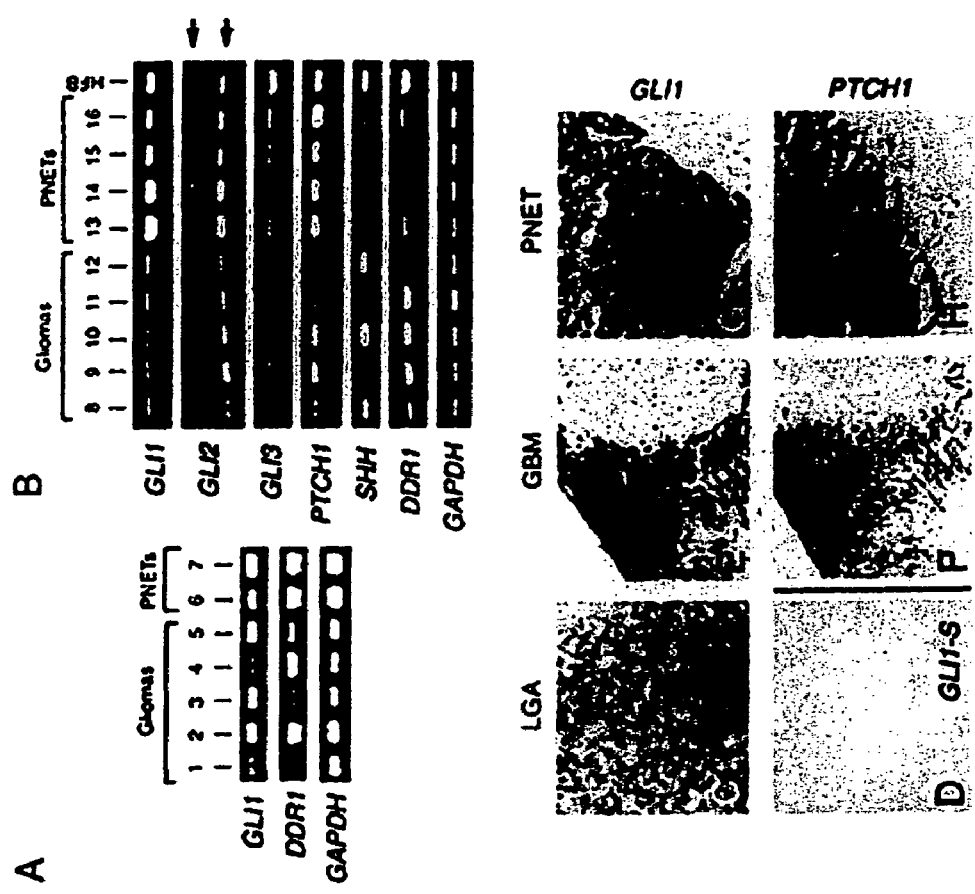

Gli genes are consistently expressed in primary brain tumors (FIG. 2) (A,B) RT-PCR analyses of independent brain tumor samples, in particular, in PNET: primitive neuroectodermal tumors; (C-H) In situ hybridization of two cortical gliomas (GBM, glioblastoma multiforme (C,D); LGA, low grade astrocytoma (E,F) and a cerebellar PNET, medulloblastoma.

Figure 3:
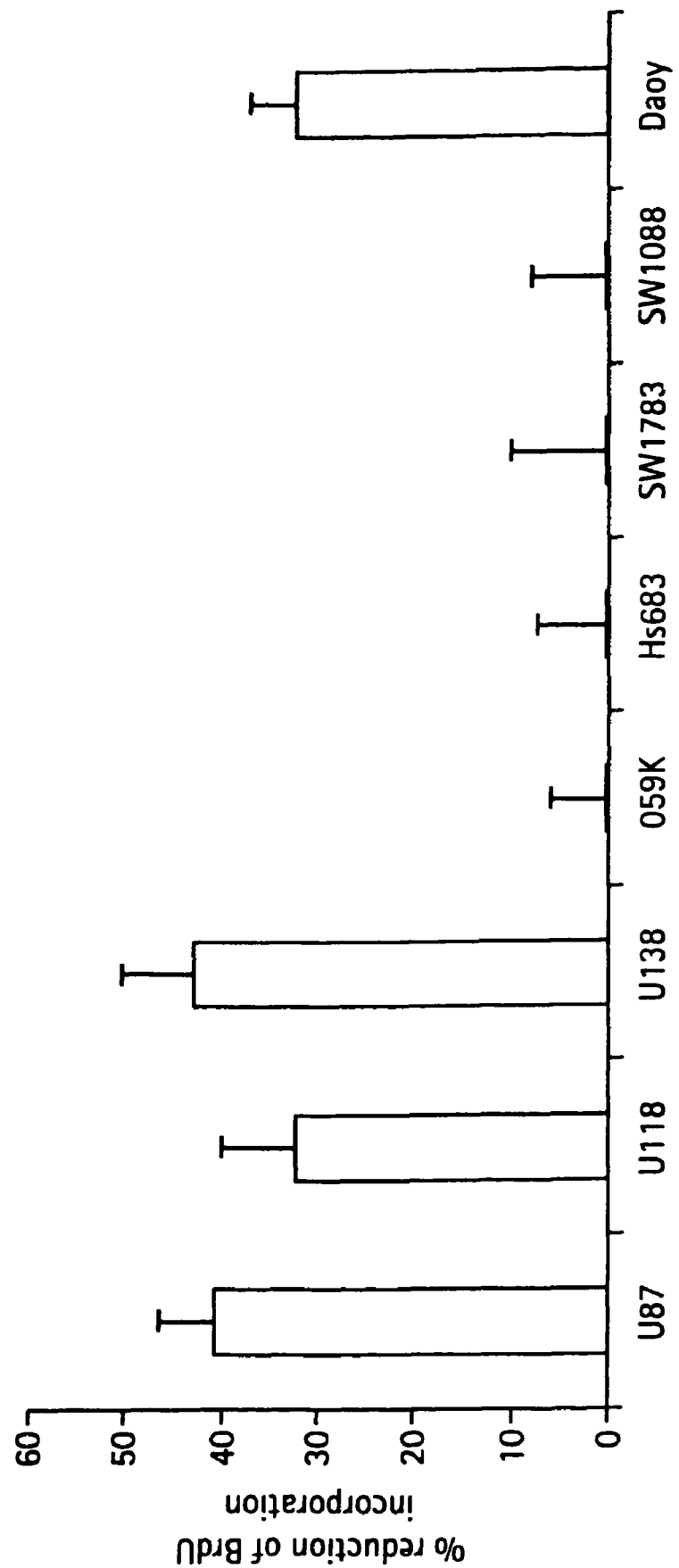

Furthermore, cyclopamine, a drug that inhibits the response to Shh signaling, modulates the proliferation of a subset of brain tumor cell lines at a concentration of 10 μM in 2.5% serum, as measured by a decrease in BrdU incorporation compared to carrier treated cells, in Glioblastoma multiforme: U87, U118, U138, 059K; in Glioma: Hs683, SW1783, SW1088; and in Medulloblastoma Daoy (FIG. 3).

Figure 4:
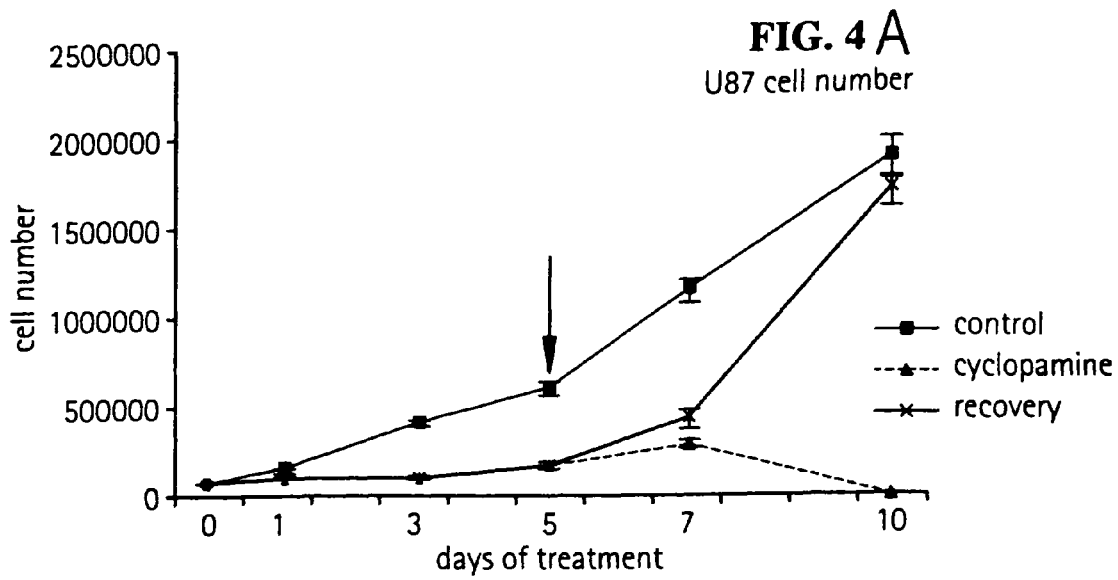
Figure 4:
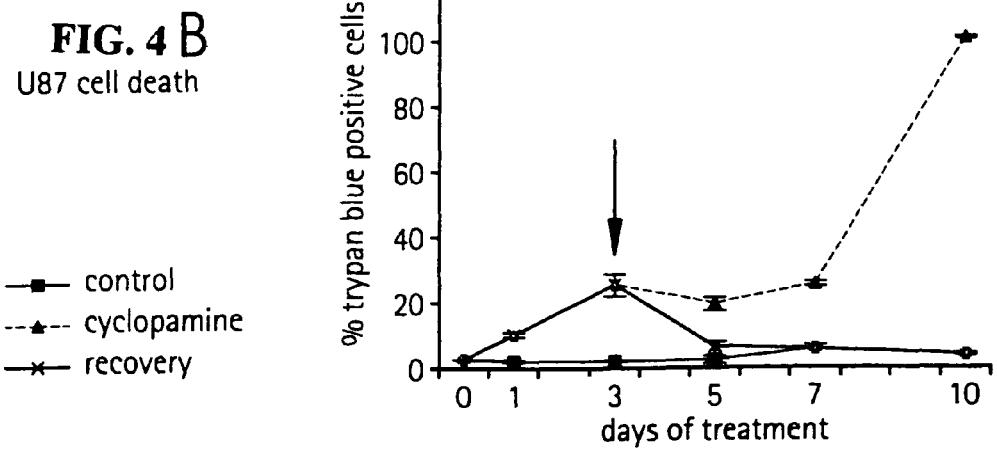
Figure 4:
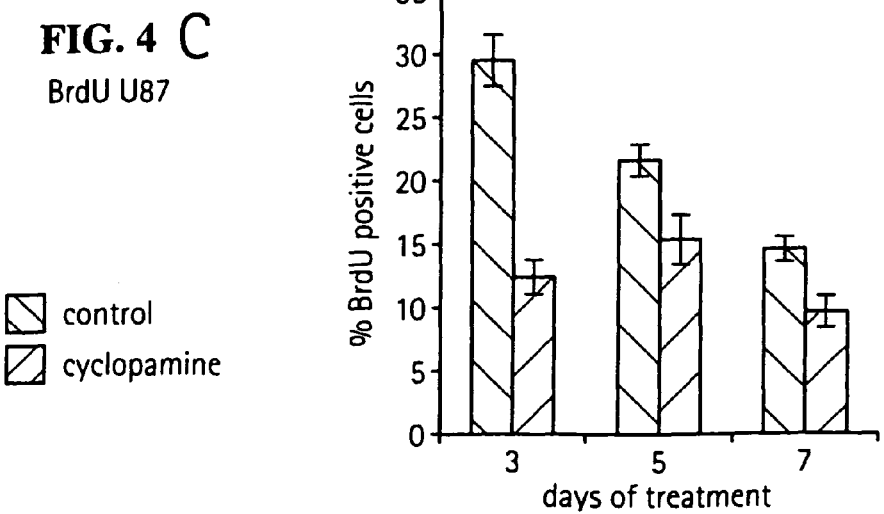

In addition, FIG. 4 demonstrates the effect of cyclopamine in long-term treatment of a glioblastoma cell line (U87) in vitro. Shh-Gli pathway controls the proliferation and viability of brain tumor cells. (A, C) shows that the proliferation of the U87 (glioblastoma) cell line is inhibited by treatment with cyclopamine (20 μM) in the presence of 10% serum (note that serum partially inhibits cyclopamine action). The cells recover upon retirement of the drug (indicated by the bar) showing that the drug is not cytotoxic. (B) A long term treatment of U87 induces death of 100% of the cells in culture.

Figure 5:
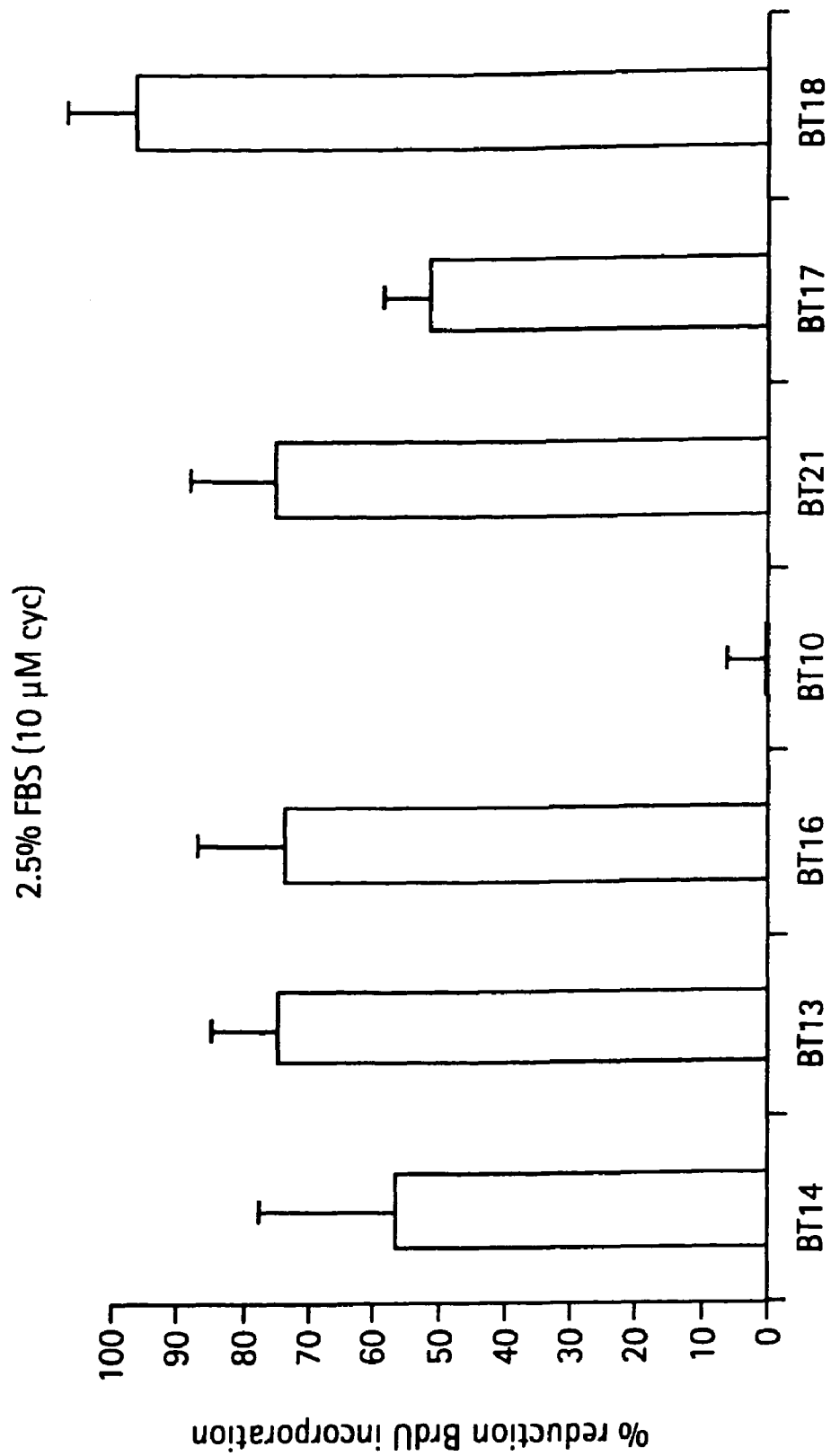

Furthermore, FIG. 5 demonstrates that cyclopamine modulates the proliferation of primary cortical gliomas that are dissociated and cultured in vitro. Inhibition of primary cortical gliomas treated with 10 μM of cyclopamine (in 2.5% serum) was measured by a decrease in BrdU incorporation in the carrier treated cells.

Figure 6:
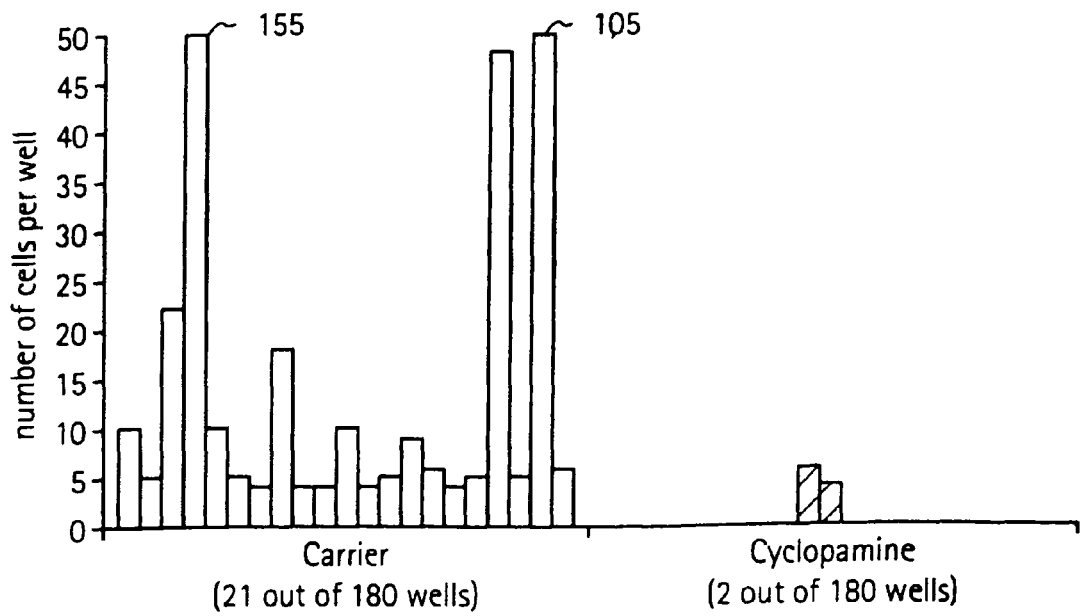
Figure 6:
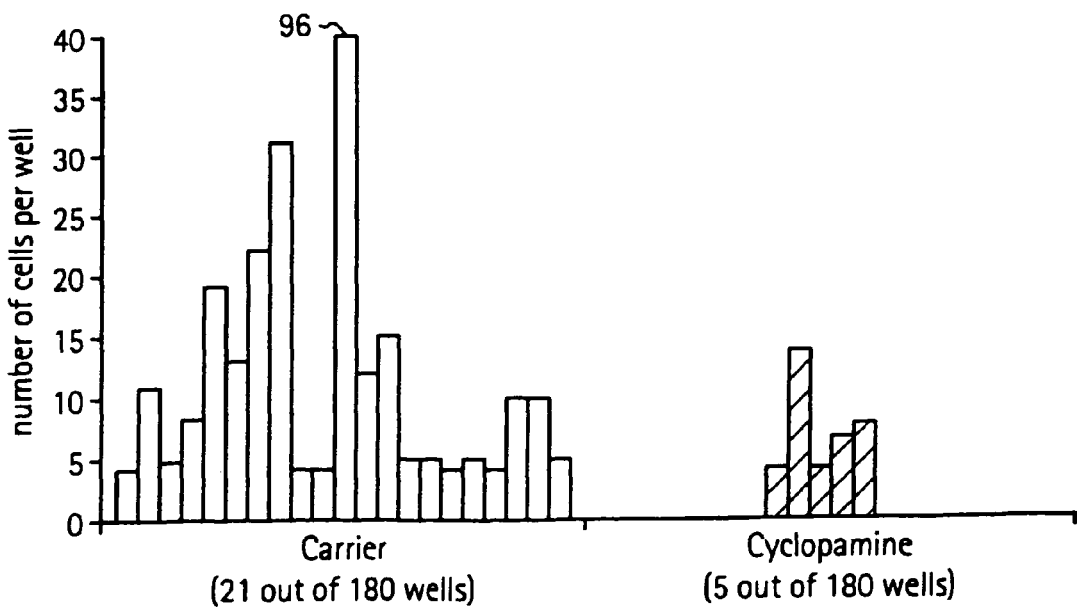

In addition, FIG. 6 demonstrates that only a subset of cells from primary brain tumors, dissociated and cultured in vitro, have stem-like properties, and their proliferation is inhibited by the presence of cyclopamine. In particular, a small number of cells from two primary brain gliomas , BT 18 (top panel) and BT22 (bottom panel) are able to produce clones when plated at a density of 1 cell per well. The size and the percentage of clones are inhibited in the presence of 10 μM of cyclopamine (in 10% serum). The graphs represent the number of cells per well after 2 weeks of culture.

Figure 7:
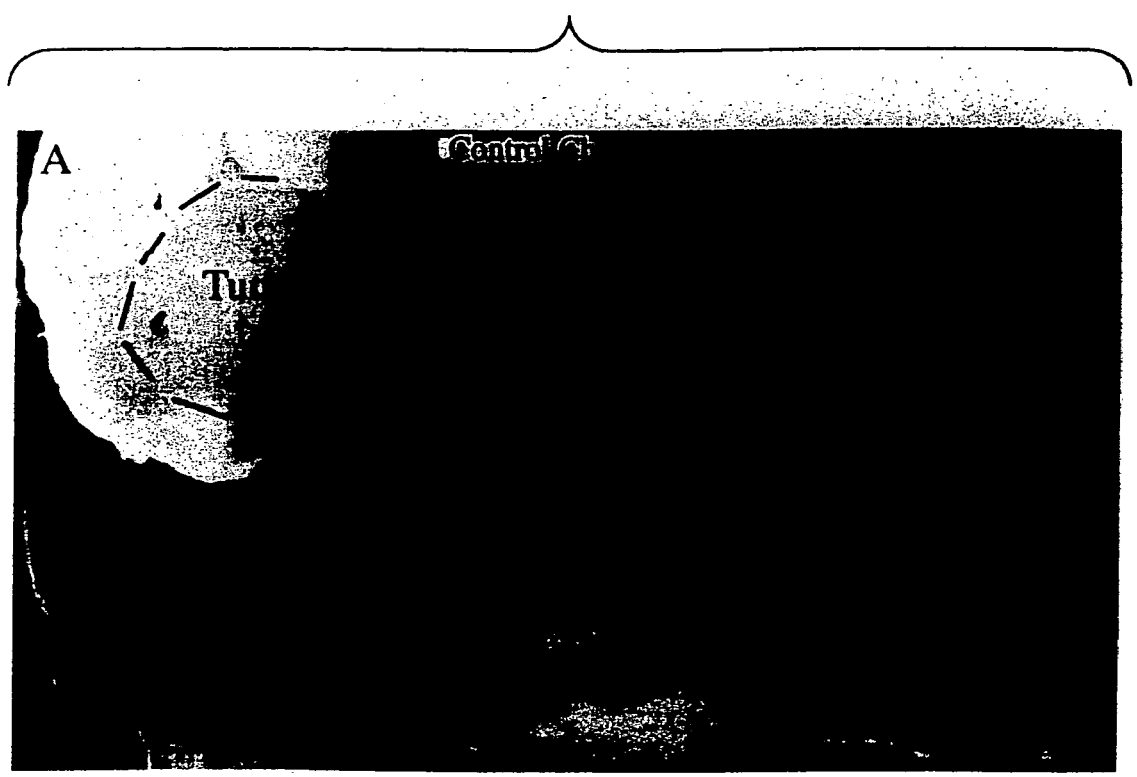

FIG. 7 demonstrates that in vivo cyclopamine treatment reduces the size of medulloblastomas of Ptch+/−, p53−/− mice. Animals were treated for a month with either cyclodextrin (carrier) (A) or cyclopamine (B). At two months of age the animals were sacrificed and the brains analyzed. (C) Sagital views of dissected cerebella. The tumors are demarcated by dashed lines.

Figure 8:
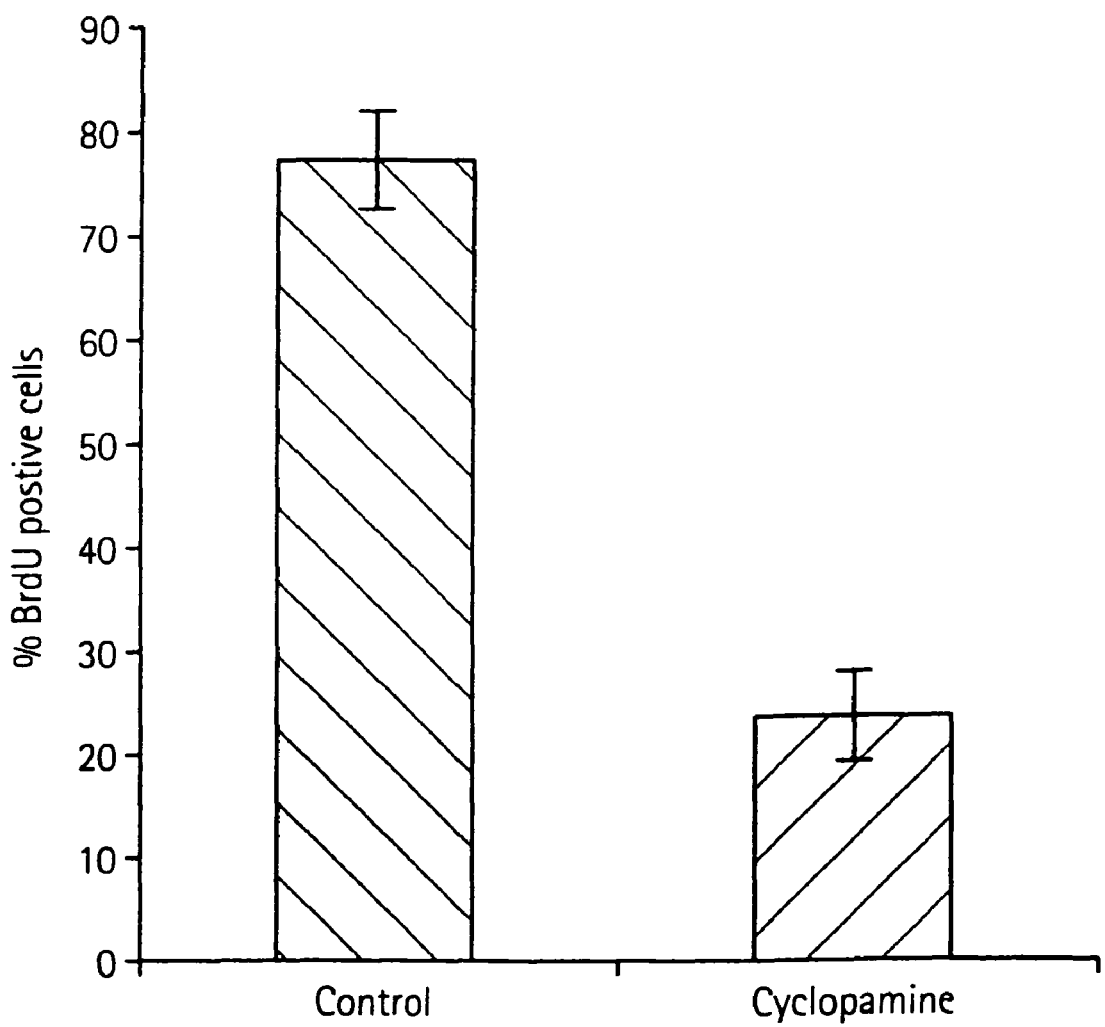

Medulloblastomas were dissected from affected mice and the cells plated for culture after dissection. FIG. 8 shows the percentage of BrdU incorporation in the presence of absence of 5 µM cyclopamine (with no serum). As shown in the figure, cyclopamine treatment resulted in a significant decrease in BrdU incorporation.

Figure 9:
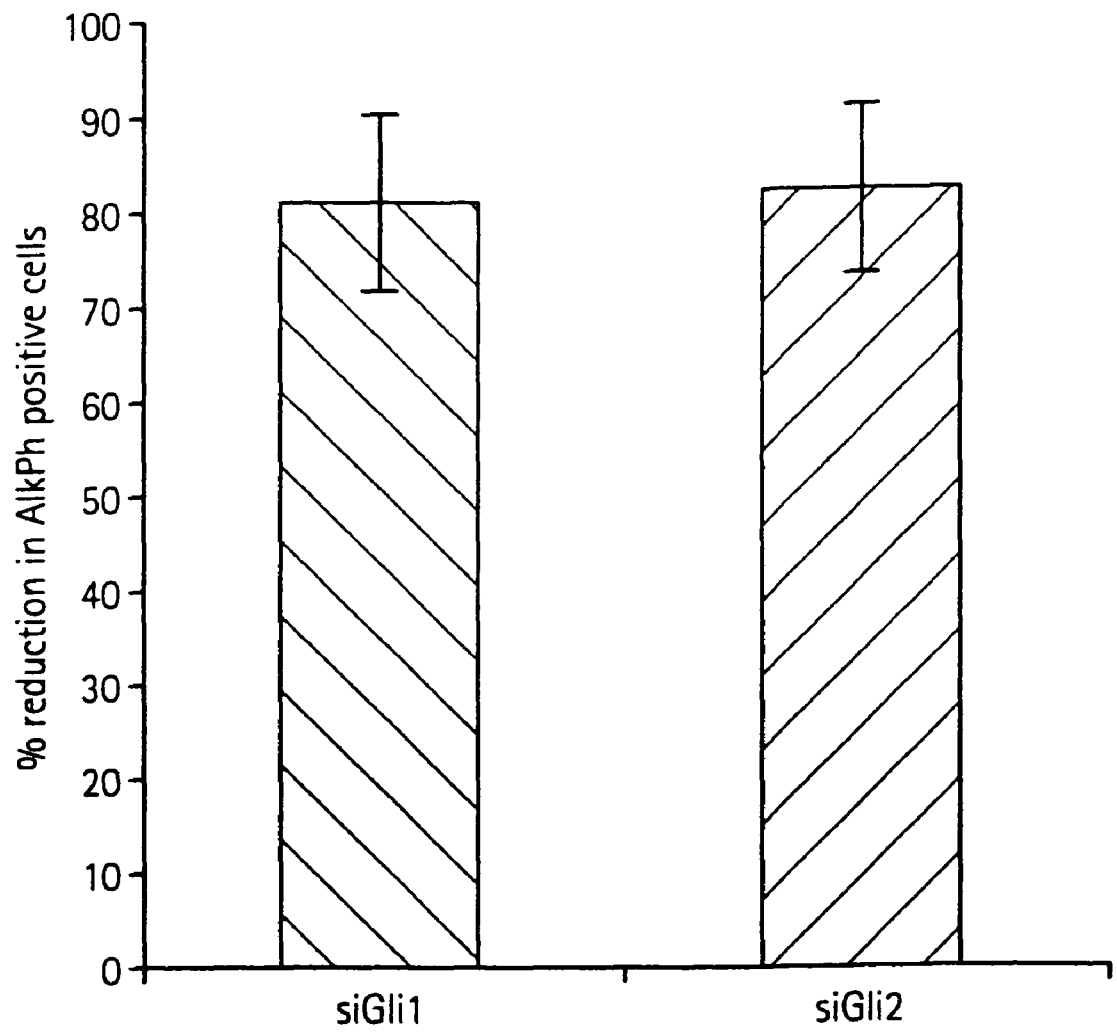

FIG. 9 demonstrates that siRNAs for Gli1 and Gli2 block Shh responses in 10T1/2 cells. In particular, Shh induces alkaline phosphatase expression in 10T1/2 cells. The results show about 80% reduction in-inhibition of alkaline phosphatase expression in the presence of siRNAs for Gli1 or Gli2 vs controls.

Figure 10:
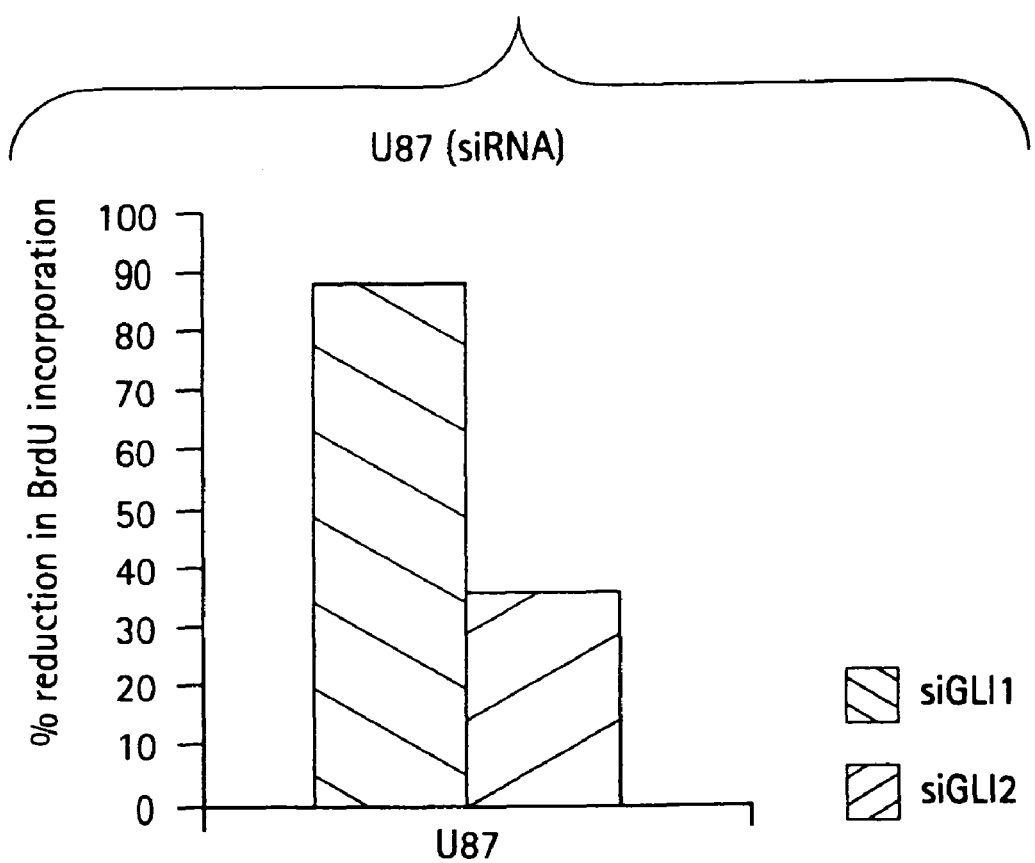
Figure 10:
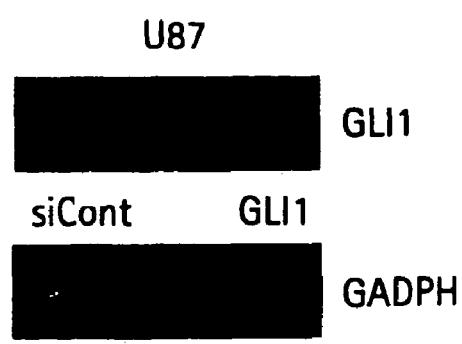

In addition, FIG. 10 shows that downregulation of Gli1 and Gli2 inhibits U87 glioma cell proliferation. In particular, BrdU incorporation in U87 cells was measured in cells that were transfected with either siControl, siGli1 or siGli2. The left panel shows the percentage of inhibition of cell growth in the cells treated with siGli1/2 vs the control. The right panel shows the decrease in Gli1 messenger after siGli transfection (measured by RT-PCR).

Figure 11:
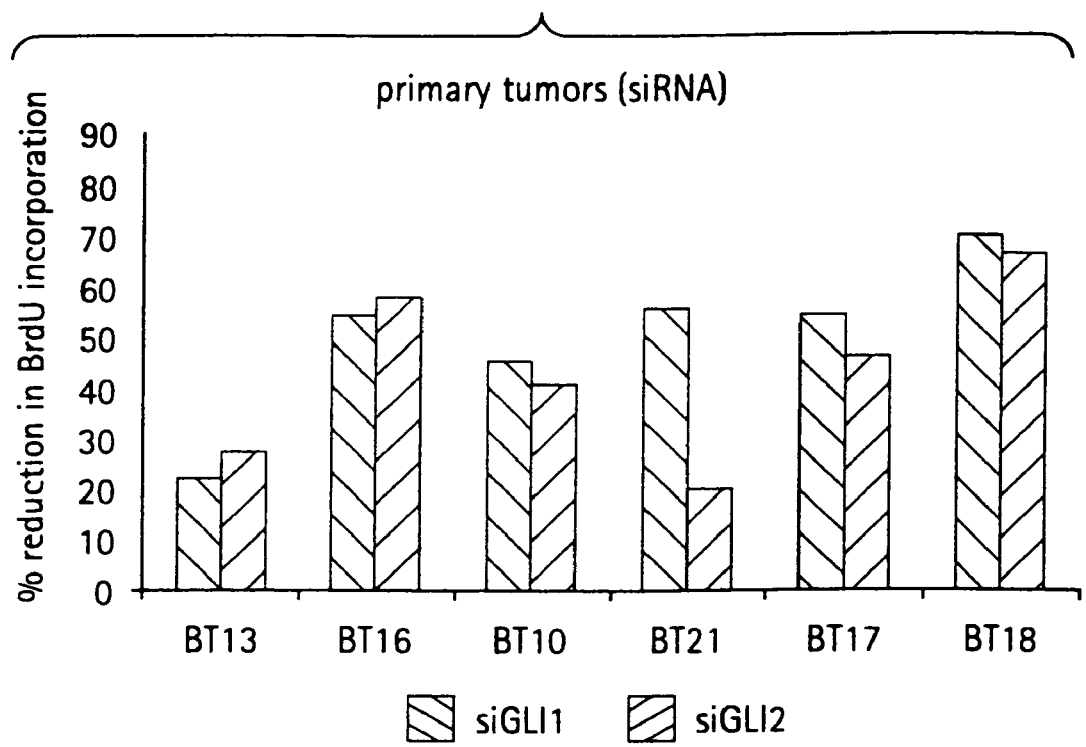
Figure 11:

FIG. 11 shows that the proliferation of primary brain tumor cells is inhibited by blocking Gli1 and Gli2. The top panel shows the percentage of inhibition of proliferation (measured by BrdU incorporation) of several primary brain tumor cells in the presence of RNA interference for Gli1 or Gli2 vs the control. The bottom panel shows the decrease in Gli1 messenger which reflects the inhibition of the SHH-Gli1 pathway after transfection of Gli1 or Gli2 siRNAs.

Example 2

Prevalent Expression of GLI1 in Lung Cancer and Increased Resistance to Apoptosis The inventors have examined the role of GLI1 in lung carcinogenesis and apoptosis. As shown below, the inventors provide evidence to support a role for GLI1 in lung tumorigenesis and more importantly from a clinical point of view, in resistance to cell killing by cancer chemotherapeutic agents.

Materials and Methods

Chemicals and Reagents

Staurosporine and etoposide were obtained from Sigma Chemical Co. (Saint Louis, Mo.) or ALEXIS Co. (San Diego, Calif.) and dissolved in DMSO (Sigma). All cell culture supplies were from Mediatech, Inc. (Herndon, Va.).

Tissue Specimens and Cell Culture

Matched primary lung cancer and normal lung tissues were obtained after approved by New York University School of Medicine Human Subjects Institutional Review Board. After surgery, tumor samples and the corresponding normal lung tissues were snap-frozen in liquid $N_2$, and stored at −80° C. Table 1 summarizes the key demographic data of the 15 cases of human lung cancers used in the study. Human lung adenocarcinoma H441 cells and epidermoid carcinoma Calu-1 cells were obtained from the American Type Culture Collection (Manassas, Va.). Mouse embryo PW fibroblasts were obtained from Dr. Costa M. H441 cells were maintained in RPMI-1640 medium, Calu-1 in McCoy's 5a medium, PW cells in Dulbecco's Modified Eagle Medium (DMEM) (Huang et al., 2001; Zhang et al., 2003) supplemented with 10% heat-inactivated fetal bovine serum, 100 units/ml of penicillin, and 100 µg/ml streptomycin. For experiments, cells were harvested from subconfluent cultures using trypsin and resuspended in fresh medium before plating.

Construction of GLI1 Expression Vector and Stable Transfection

The full-length human GLI1 gene (GenBank accession number, NM-005269) was cloned into the mammalian expression vector pcDNA3 (Invitrogen). For stable transfection, FuGene 6 reagent (Roche) was used and 1 µg of pcDNA or pcDNA-GLI1 DNA per sample was added. G418 was used at 400 µg/ml at 48 h posttransfection.

RT-PCR and Real-time PCR

Total RNA were isolated from human lung tissue samples, lung cell lines, and transfectants of PW or H441 cells by using RNeasy Mini Kit (QIAGEN Inc. Valencia, Calif.) and reverse-transcribed into cDNA by using 1st Strand cDNA Synthesis Kit for RT-PCR (AMV) (Roche). Real-time PCR was performed on ABI PRISM 7000 Sequence Detection System (Applied Biosystems) by 40 cycles at 95° C. for 15 sec and 60° C. for 60 sec using SYBR Green PCR Master Mix (Applied Biosystems). The dissociation curve was run to ensure the single product amplification during the PCR assay. The expression of GLI1 for each sample was normalized to the β-actin expression level in the same sample. The primers and conditions for human GLI1, GLI2, GLI3, SHH and GAPDH were as described (Dahmane et al., (2001), 128: 5201-5212). Primers for human β-actin were:

5'-TCACCCACACTGTGCCCATCTACGA-3'   (SEQ ID NO: 27)
and
5'-CAGCGGAACCGCTCATTGCCAATGG-3'.  (SEQ ID NO: 28)

Cell Viability Assay

Cell viability after staurosporine or etoposide treatment was assessed using CellTiter 96 Aqueous Non-Radioactive Cell Proliferation Assay kit (Promega). It is to measure the amount of 490 nm absorbance of MTS (3-(4,5-dimethylthiazol-2-yl)-5-(3-carboxymethoxyphenyl)-2-(4-sulfophenyl)-2H-tetrazolium) bioreduced product formazan which is directly proportional to the number of viable cells in culture. Briefly, $10^4$ transfectants of H441 cells or 4000 transfectants of PW cells were seeded onto each well of 96-well microplates overnight to allow cells to attach to the growth surface. 0, 0.01, 0.05, 0.1, 0.5, 1, 5, 10 µM (for H441 transfectants) or 0, 0.001, 0.005, 0.01, 0.05, 0.1, 0.5, 1 µM (for PW transfectants) of staurosporine, or 0, 50, 100, 250, 500 µM (for H441 transfectants) or 0, 1, 5, 10, 50, 100 µM (for PW transfectants) of etoposide was added to a final volume of 100 µl medium per well. After 24 h or 48 h treatment, 20 µl of the combined MTS/PMS solution was pipetted directly into each well of the 96-well assay plate containing 100 µl of cells in culture medium. The absorbance at 490 nm was recorded using an EL 800 universal microplate reader (Bio-Tek, Winooski, Vt.) after 2-3 hours incubation. The wells that only contain 100 µl of medium but without cells were used as blank. And the wells with cells but without staurosporine or etoposide treatment were used as control.

Measurement of Caspase 3 (-like) Activity

Caspase 3 (-like) activity was performed by using Caspase-3/CPP32 Colorimetric Assay Kit (BioVision Research Products). The assay is based on spectrophotometric detection of the chromophore ρ-nitroanilide (ρ-NA) after cleavage from the DEVD-ρ-NA by caspase 3. Briefly, $1.5 \times 10^6$ transfectants of PW cells or $3 \times 10^6$ transfectants of H441 cells were seeded in a 100-mm culture dish overnight. For time-response assay, cells were treated with 1 μM (for H441 transfectants) or 100 nM (for PW transfectants) of staurosporine for 1, 3, 6, 16, 24 h. For dose-response assay, cells were treated by 0.1, 0.5, 1, 5, 10 μM (for H441 transfectants) or 0.001, 0.01, 0.1, 1 μM (for PW transfectants) of staurosporine for 6 h. Cells treated with drug vehicle (DMSO) alone were used as control. After treatment, total cells were collected by combination of the attached cells and the floating cells. Protein concentrations were assayed by using the Bio-Rad Protein Assay. For each assay, 100 μg protein from PW transfectants or 200 μg protein from H441 transfectants was used. Absorbances at 405 nm were measured using an EL 800 universal microplate reader (Bio-Tek). The wells that contained all reagents except proteins were used as blanks.

DNA Fragmentation Assay $1 \times 10^6$ transfectants of H441 cells were seeded in a 60-mm culture dish and cultured overnight. After 1, 2, 3, 4, 5 μM of staurosporine treatment for 24 hours, cells still attached on the culture surface were collected by trypsinization and cells floating in the medium were collected by centrifugation. The control cells were treated with drug vehicle (DMSO) alone. Combined cells after twice ice-cold PBS washing were used to perform the genomic DNA extraction by standard techniques (White M K, Baireddy V and Strayer D S. (2001). *Exp. Cell Res.*, 263, 183-192).

Results

Expression of GLI1, GLIi2, GLI3 and SHH in Human Lung Cancer

RNA from fresh snap-frozen lung cancer and adjacent normal lung tissues from resections of the same patients was tested for the presence of GLI1 transcripts by real-time PCR and RT-PCR. The fold change of GLI1 expression relative to β-actin expression in the lung cancer (C) of 15 patients as compared to the matched normal lung tissues (N), i.e., C/N ratio, ranged from 0.81 to 44.81 (Table 3). 11/15 cases (73.3%) showed >2-fold and 6/15 (40%) showed >4-fold higher GLI1 expression in the cancer samples than in matched normal lung tissues. Expression of GLI1 in lung cancer tissues was significant higher than that in normal lung tissues (p<0.05). However, its expression was not obviously correlated with age, gender, or pathological diagnosis (Table 1).

TABLE 1

| Diagnosis | Grade | GLI1 (C/N fold) | Metastasis | Gender | Age |
|---|---|---|---|---|---|
| Adenocarcinoma | I | 2.63 | – | M | 63 |
| Adenocarcinoma | I | 2.23 | – | F | 66 |
| Adenocarcinoma | II | 0.81 | – | M | 70 |
| Adenocarcinoma | II | 1.89 | – | M | 79 |
| Adenocarcinoma | II | 1.51 | – | M | 72 |
| Adenocarcinoma | II/III | 2.40 | + | F | 76 |
| Adenocarcinoma | III | 44.81 | – | F | 41 |
| Adenocarcinoma | III | 3.12 | + | M | 74 |
| Bronchiolo-alveolar carcinoma | I | 0.88 | – | M | 81 |
| Carcinoid tumor | I | 23.55 | – | F | 71 |
| Pulmonary carcinoid tumor | II | 4.48 | – | M | 75 |
| Squamous cell carcinoma | I | 3.88 | + | M | 74 |
| Squamous cell carcinoma | II | 8.38 | – | F | 76 |
| Squamous cell carcinoma | II | 30.23 | – | F | 63 |
| Squamous cell carcinoma | II/III | 6.65 | – | M | 62 |

Figure 12:
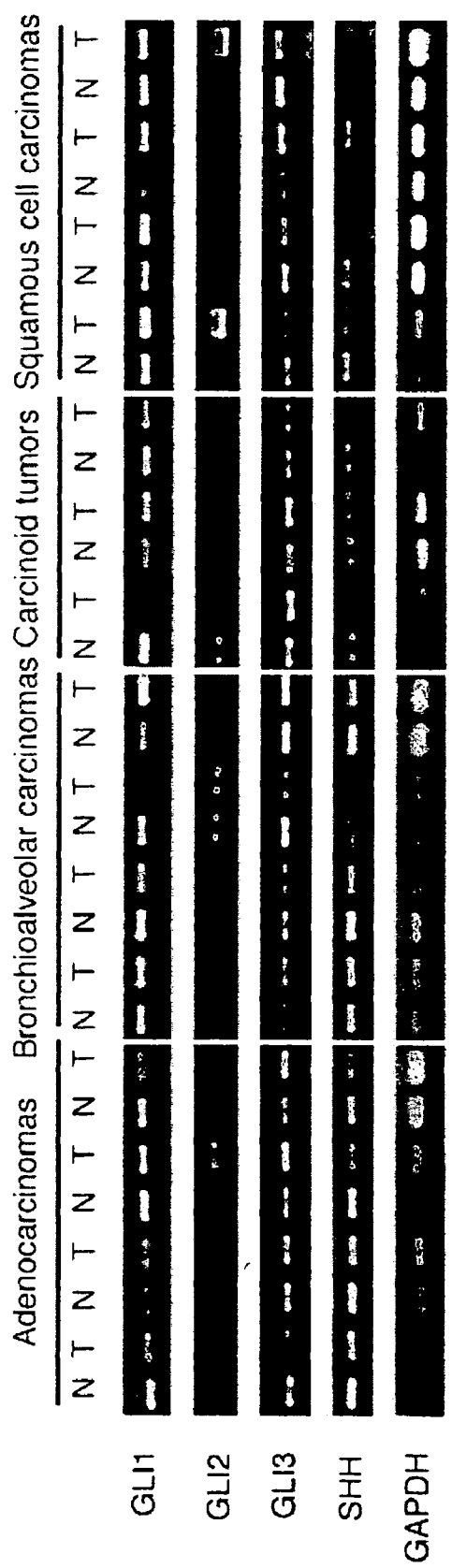
FIG. 12 Expression of GLI1, GLI2 and GLI3 and SHH in human lung cancer and matched normal lung tissues. T, lung cancer; N, matched normal lung tissue. The levels of expression of GAPDH are used as control.

RT-PCR analyses showed variable levels of GLI1 in tumor samples as compared with their matched normal lung tissues (FIG. 12), with 5 cases showing clear upregulation of GLI1. Three of these were squamous cell carcinomas (FIG. 12). GLI2 was not expressed in most normal or tumor samples and of those 4 cases showed upregulation in cancer tissues. Two of these were squamous cell carcinomas (FIG. 12). In contrast to GLI2, GLI3 expression was found in all samples and of these six showed varying levels of downregulation (FIG. 12). SHH expression was detected in most samples at varying levels but without a clear trend in tumor versus normal samples. Expression of GLI1 and SHH was not found in the H441 or Calu-1 lung cancer cell lines (data not shown).

Increased Resistance to Staurosporine-induced Apoptosis by GLI1 Overexpression

Figure 13:
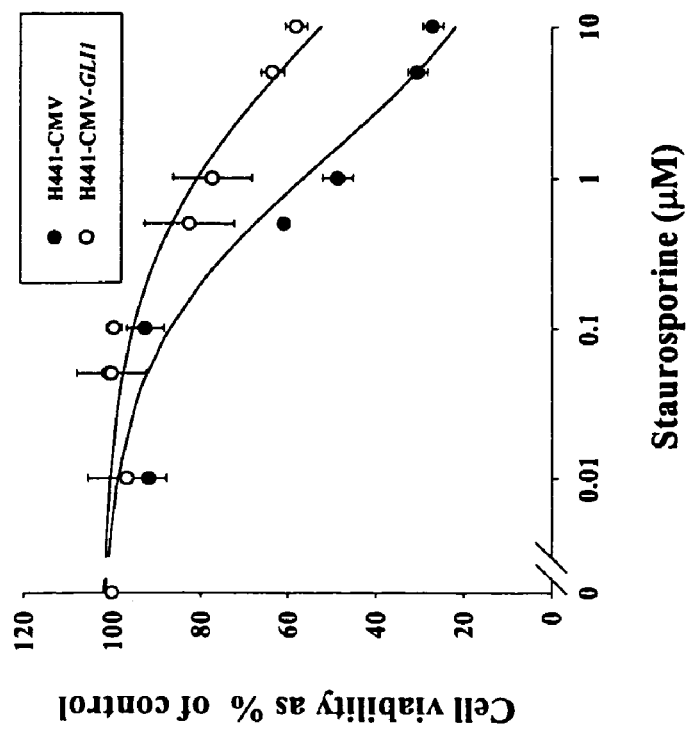
FIG. 13 Overexpression of GLI1 in H441 cells, resistance to staurosporine-induced apoptosis and effects on DNA laddering. (a) Expression of GLI1 was measured by real-time PCR in H441 cells transfected with the pcDNA3 vector control (H441-CMV) or pcDNA3-CMV-GLI1 (H441-CMV-GLI1). The expression of GLI1 was normalized by the expression of β-actin and the results are mean ±SD of three experiments. (b) MTS assay of cell viability after treatment with staurosporine. Transfectants of H441 cells were treated with indicated concentration of staurosporine for 24 h. Cell viability was measured by MTS assay and the data were mean ±SD of three experiments with triplicates in each experiment and expressed as a percentage of the DMSO vehicle-treated control. (c) GLI1 protects cells from staurosporine-induced apoptosis by DNA fragmentation assay. Transfectants of H441 cells were treated by indicated concentration of staurosporine for 24 hours. Genomic DNA was extracted and visualized in 2% agarose gel with ethidium bromide. M, 100 bp DNA ladder (Promega).
Figure 13:
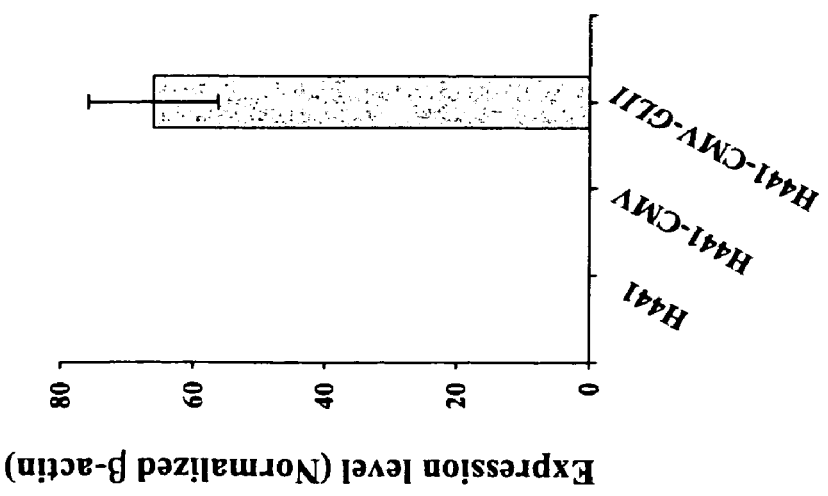

To examine the effects of GLI1 overexpression in apoptosis, GLI1-negative H441 lung adenocarcinoma cells were transfected with pcDNA3-GLI1 or the pcDNA3 vector as control. Following G418 selection, six clones expressing similar levels of GLI1 were pooled and the expression of GLI1 was measured (FIG. 13a).

The protein kinase inhibitor staurosporine has been reported to induced apoptosis, including DNA laddering, in H441 cells (White M K, Baireddy V and Strayer D S. (2001). *Exp. Cell Res.*, 263, 183-192). To ascertain the role of GLI1 in apoptosis, H441 vector control and H441 GLI1-expressing cells were treated with increasing doses of staurosporine and cell viability was measured by the MTS assay. Cell toxicity increased with increasing doses of staurosporine at 24 h after treatment (FIG. 13b). Interestingly, H441 GLI1-expressing cells were more resistant to staurosporine-induced cell death as compared to the vector control cells (FIG. 13b). The $IC_{50}$ in GLI1-expressing H441 cells was 9.76±2.09 μM compared to 1.25±0.25 μM in vector control cells (p <0.05).

Figure 13C:
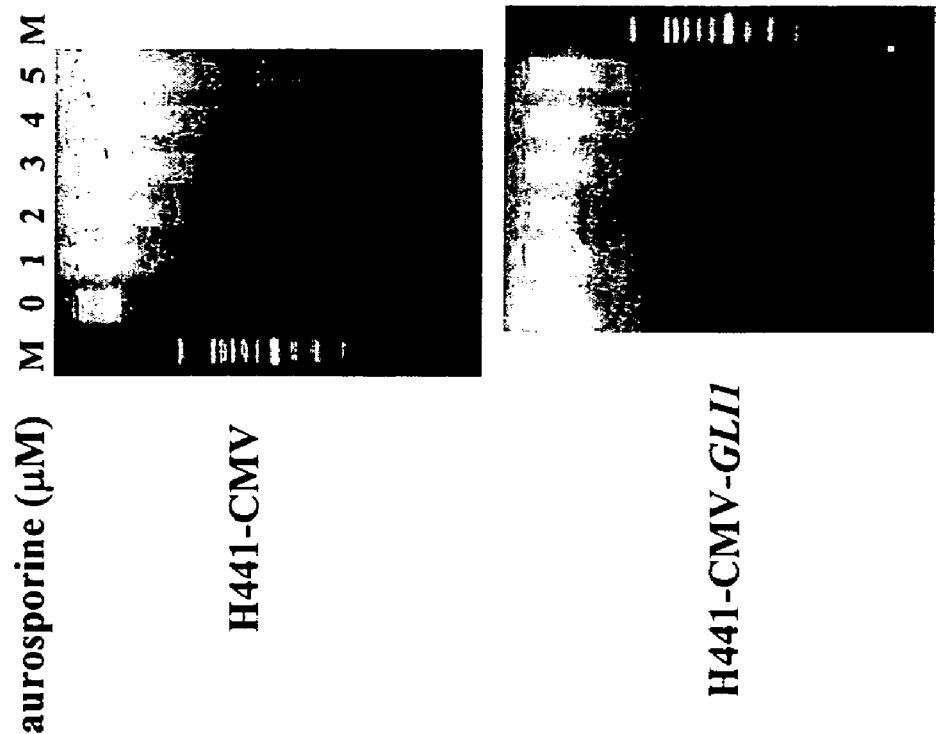

Apoptosis, assessed by a DNA fragmentation assay (FIG. 13c), was observed in H441 vector control cells treated with low doses of staurosporine. In contrast, higher doses of staurosporine were needed to induce similar DNA laddering in H441 GLI1-expressing cells. This result is consistent with a GLI1-induced increased resistance to staurosporine-induced cell toxicity as measured by the MTS assay (FIG. 13b).

Figure 14:
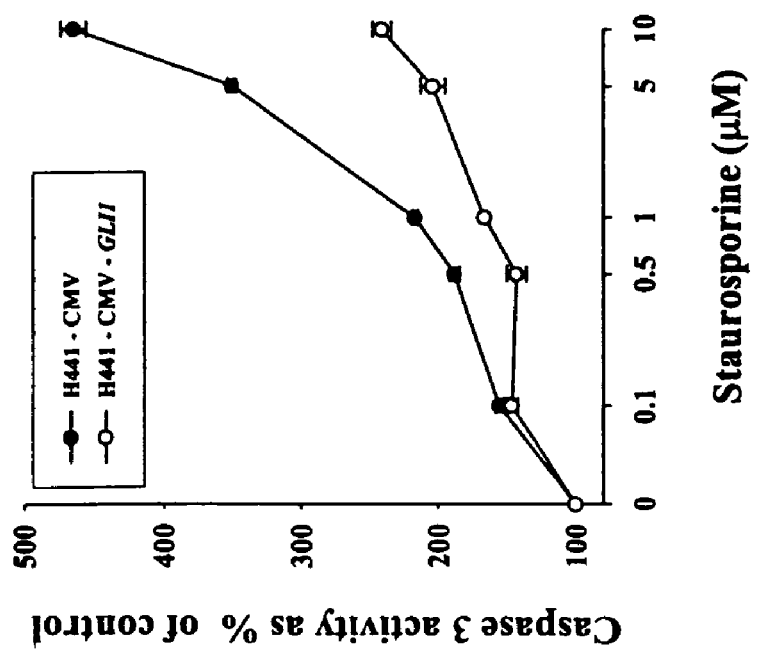
FIG. 14 GLI1 protects H441 cells from staurosporine-induced caspase 3 activation. (a) Caspase 3 activity in H441 vector control cells induced by staurosporine was measured by calorimetric assay. H441 vector control cells were treated with 1 μM staurosporine and caspase 3 activity was measured at different timepoints after treatment. (b) H441 vector control (H441-CMV) and GLI1 expressing cells (H441-CMV-GLI1) were treated with increasing doses of staurosporine and caspase 3 activity was measured at 6 h after treatment. The results are expressed as a percentage of the DMSO vehicle-treated control. Data are mean±SD of three experiments.
Figure 14:
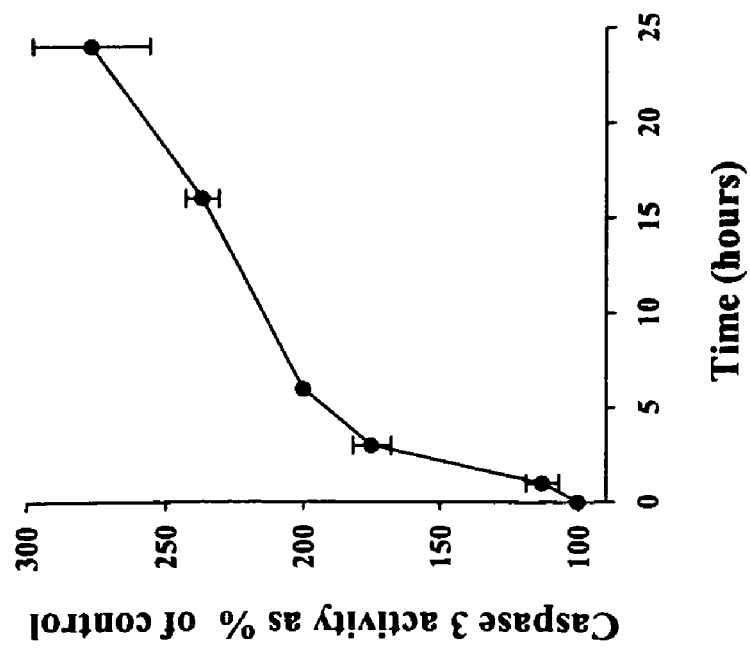

GLI1 expression suppresses caspase 3 activity induced by staurosporine in H441 lung cancer cells. Caspase 3 (CPP32) is a key effector of apoptosis. To ascertain if staurosporine-induced apoptosis is mediated by this caspase, its activity was first assayed over a time course. Since the $IC_{50}$ in H441 vector control cells was ~1.25 μM, H441 vector control cells were treated with 1 μM staurosporine to ascertain the kinetics of caspase 3 activation. Caspase 3 activity was induced by staurosporine and increased over a 24 h period (FIG. 14a). Consistent with increased resistance to staurosporine-induced apoptosis in GLI1-expressing cells, caspase 3 activity was consistently lower in H441 GLI1-expressing cells than that in vector control cells at all doses of staurosporine tested (FIG. 14b).

Figure 15A:
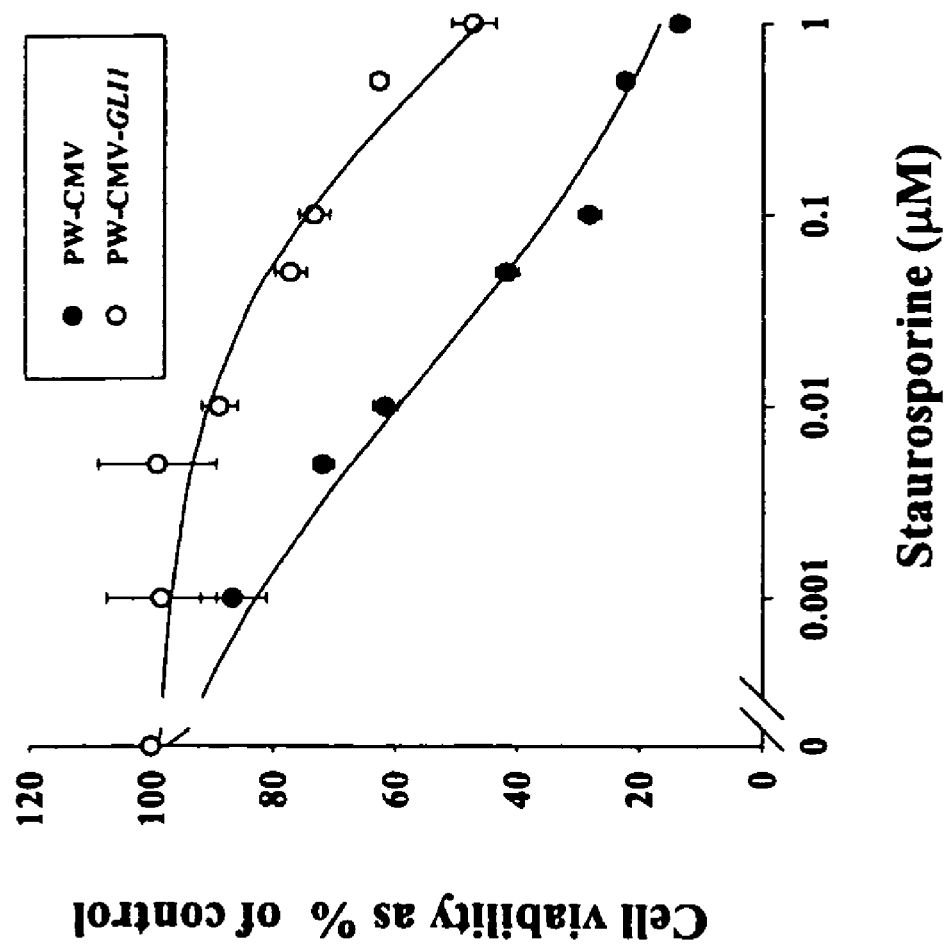
FIG. 15 Expression of GLI1 in PW embryo fibroblast increased resistance to staurosporine-induced apoptosis and inhibition of caspase 3 activation. (a) Transfectants of PW vector control cells (PW-CMV) and GLI1-expressing PW-C18 (PW-CMV-GLI1) were treated with indicated concentration of staurosporine and cell viability was measured by MTS assay at 24 h after treatment. The data were mean ±SD of three experiments with triplicates in each experiment and expressed as a percentage of the DMSO vehicle-treated control. (b) Caspase 3 activity in PW vector control cells induced by staurosporine was measured by calorimetric assay. Cells were treated with 100 nM staurosporine and caspase 3 activity was measured at different timepoints after treatment. (c) PW vector control (PW-CMV) and GLI1-expressing PW-C18 cells (PW-CMV-GLI1) were treated with increasing doses of staurosporine and caspase 3 activity was measured at 6 h after treatment. The results in b and c are expressed as a percentage of the DMSO vehicle-treated control. Data are mean ±SD of three experiments.
Figure 15B:
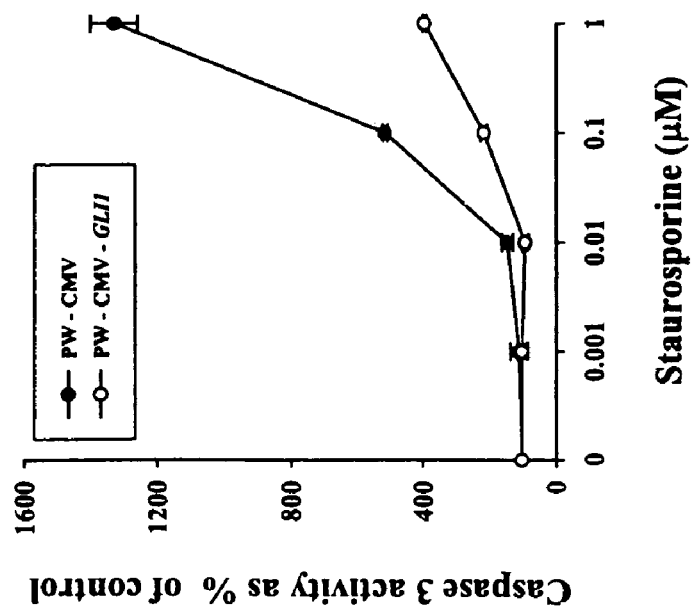
Figure 15C:
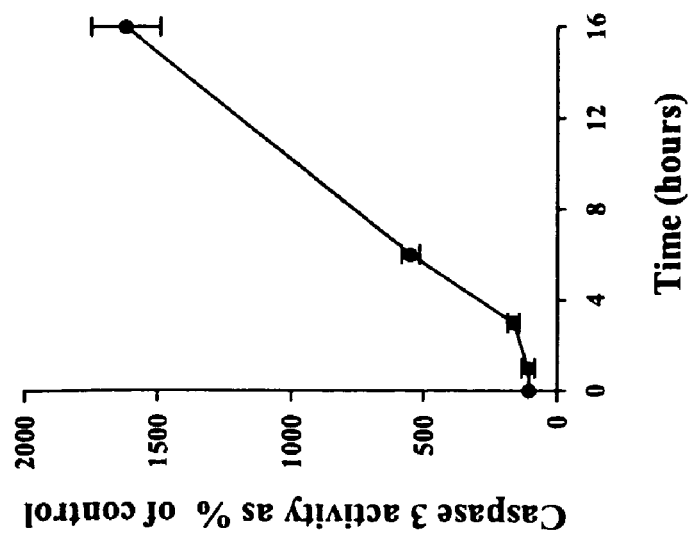

GLI1 induced increased resistance to staurosporine-induced apoptosis may be a general phenomenon. To determine if increased resistance to staurosporine-induced apoptosis by GLI1 expression might be a general effect of GLI1, we transfected mouse embryo PW fibroblasts with GLI1 and selected for G418 resistance. Cell viability of PW vector control cells and GLI1-expressing clone 18 (PW-C18; a clone expressing high levels of GLI1) cells was compared after treatment with increasing doses of staurosporine (FIG. 15a). The $IC_{50}$ was 0.876±0.218 µM for PW-C18 cells which was significantly higher than that for vector control cells (0.064±0.009 µM, $p<0.001$) after 24 h staurosporine treatment. Similar to that in H441 control cells, staurosporine in PW vector control cells increased over time (FIG. 15b). Caspase 3 activity was 1.6-fold, 2.4-fold, and 3.4-fold lower in GLI1-expressing PW cells as compared to that in the vector control cells after treatment with 0.01 µM, 0.1 µM, and 1 µM staurosporine, respectively (FIG. 15c).

Figure 16:
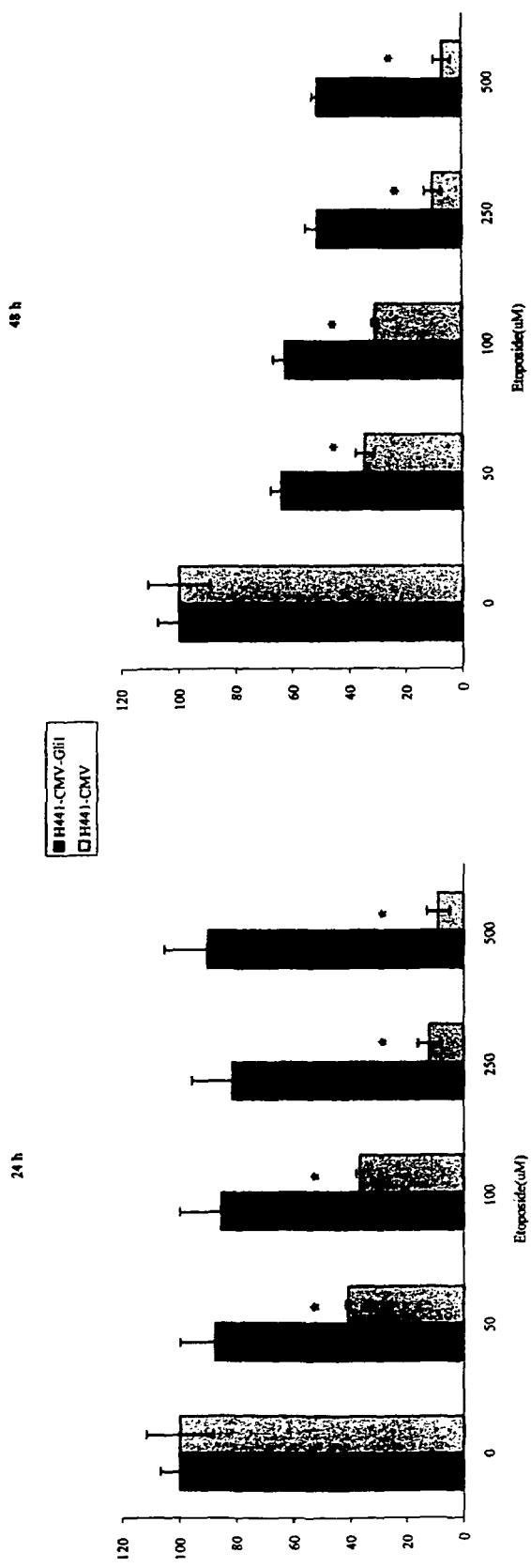
FIG. 16 GLI1 protects H441 cells from etoposide-induced cell death. MTS assay of cell viability after treatment of H441 or PW vector control cells (H441-CMV or PW-CMV) and GLI1-expressing cells (H441-CMV-GLI1 or PW-CMV-GLI1) with increasing doses of etoposide. The data were expressed as a percentage of the DMSO vehicle-treated control at 24 h and 48 h posttreatment. Data are mean±SD of three experiments.
Figure 16:
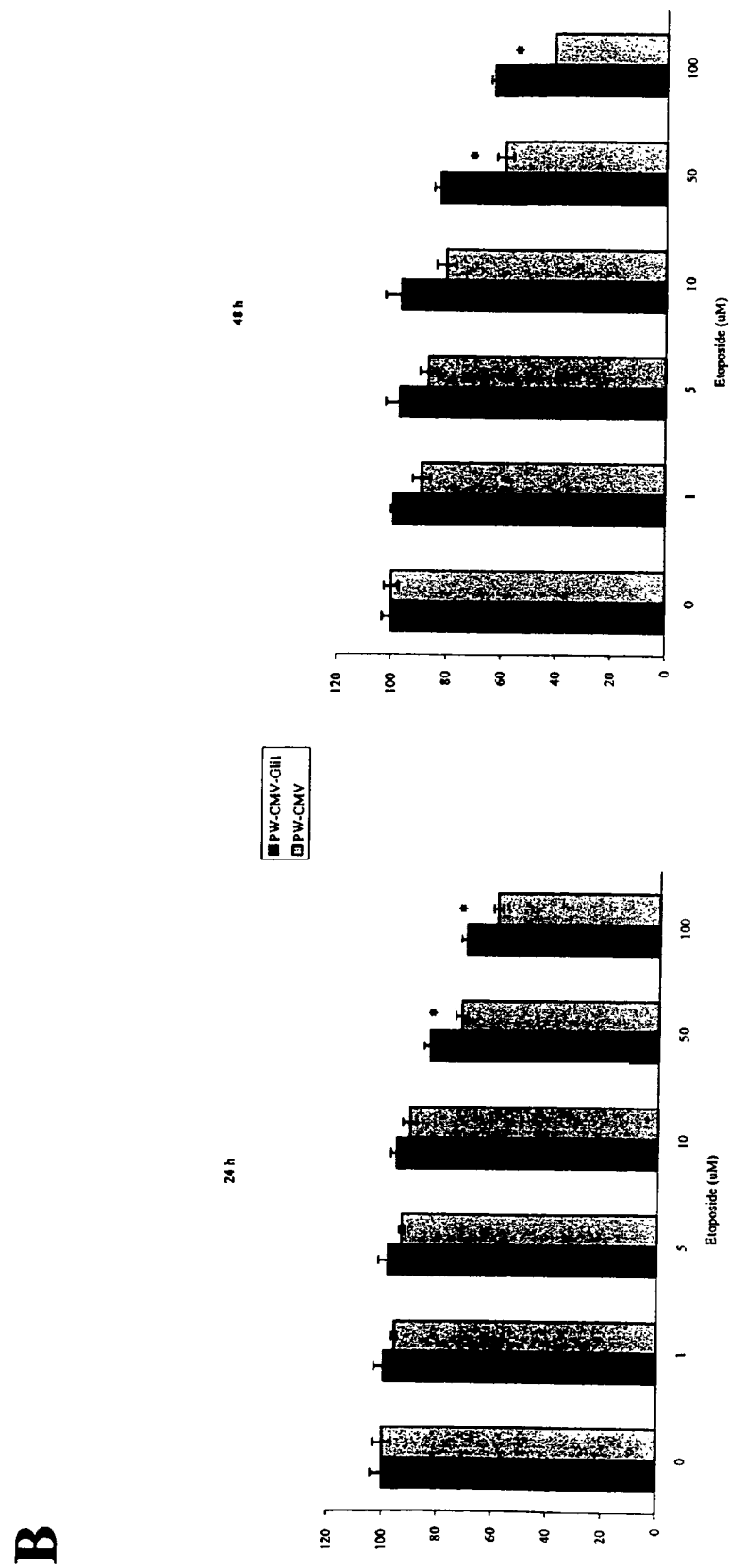

Overexpression of GLI1 increased resistance to etoposide-induced cell death Impaired apoptosis is a significant impediment to effective chemotherapy for lung cancer. The inventors examined the effects of GLI1 expression on the resistance to the cytotoxic effects of etoposide, a widely used chemotherapeutic agent for lung cancer. H441 vector control cells and GLI1-expressing cells were treated with increasing doses of etoposide and cell viability was measured by the MTS assay. GLI1-expressing cells were found to be more resistant to cell death induced by all doses of etoposide at both 24 h and 48 h post treatment (FIG. 16a).

Resistance to death by etoposide by GLI1 overexpression was also measured in PW mouse fibroblast cells. GLI1 expressing cells were found to be more resistant to cell death induced by higher doses of etoposide at both 24 h and 48 h post treatment (FIG. 16b). This result is consistent with a GLI1-induced increased resistance to etoposide-induced cell toxicity as measured by the MTS assay.

Summary

The inventors have demonstrated that GLI1 is consistently expressed, and often overexpressed, in a variety of non-small cell lung cancers. Moreover, the inventors show that GLI1 plays a role in regulating apoptosis and resistance to chemotherapy. The inventors have found consistent expression of GLI1 and SHH in adenocarcinomas, brochioalveolar carcinomas, carcinoid tumor and squamous cell carcinomas. We find that GLI1 protects cells from caspase-induced apoptosis and from chemotherapeutic agent damage, suggesting a new role for GLI1 in cancer, in addition to the control of proliferation. The inventors have also found that GLI1 protects cells from caspase-induced apoptosis and from chemotherapeutic agent damage, suggesting a new role for GLI1 in cancer.

Defects in apoptosis are implicated in both tumorigenesis and drug resistance in chemotherapy (Shivapurkar N, Reddy J, Chaudhary P M and Gazdar A F. (2003). *J. Cell Biochem.,* 88, 885-898.). It is therefore important to understand the molecular events that contribute to drug-induced apoptosis and the underlying mechanisms of how tumors evade apoptotic death. Here the inventors have examined if GLI1 affects the cytotoxic effects of staurosporine and etoposide. Staurosporine has been shown to induce apoptosis in a variety of cell lines, including various cancer cells. Stable expression of GLI1 inhibited caspase 3 activity and prevented both human lung adenocarcinoma H441 and mouse embryo fibroblast PW cells from apoptotic cell death induced by staurosporine, suggesting decreased apoptosis may be an important consequence of GLI1 expression during lung carcinogenesis but possibly also in other cancers that express GLI1, such as basal cell carcinomas, medulloblastomas, rhabdomyosarcomas and pancreatic cancer. It remains possible that such anti-apoptotic effect of GLI1 normally counteracts the caspase 3 mediated apoptosis induced by Ptc 1, this acting as a ligand-dependent death receptor. SHH-Gli signaling may thus insure the viability of expressing cells, which is a critical step in cancer. In addition, a normal role of GLI1 in preventing apoptosis could be found in maintaining a healthy proliferative status of stem cells and early precursors.

Etoposide, which is one of the DNA topoisomerase II inhibitors, is initially effective in the treatment of lung cancer. DNA damage induced by cytotoxic topoisomerase II inhibitors such as etoposide is a consequence of the interruption of the enzymecatalytic cycle. Etoposide acts within the DNA-enzyme complex to stabilize a covalent intermediate, termed the 'cleavable complex', initiating a sequence of events leading to cell death. Exposure to etoposide induces a prominent G2 delay, particularly in p53 dysfunctional cells, with evidence that S phase progression may also be affected at higher dose levels. Of clinical relevance is that overexpression of GLI1 in H441 lung carcinoma cells also increased resistance to the cytotoxic effects of etoposide is raising the possibility that GLI1 plays a role in chemoresistance to anti-cancer drugs. Hence, lung cancers that express high levels of GLI1 may be more chemoresistant than those that do not express or express low levels of GLI1, suggesting that GLI1 may represent a novel target for cancer drug screening. Active compounds that induce apoptosis independent of GLI1 overexpression and/or inhibit GLI1 activity and function may have efficacy singly or as adjuvant therapy in the chemotherapy of lung cancer.

What is claimed is:

1. A method of inducing apoptosis in an in vitro tumor cell that expresses a GLI protein comprising administering an siRNA molecule comprising SEQ ID NO: 29 to the tumor cell, wherein said administering results in tumor cell death.

2. The method of claim 1, wherein said tumor cell is selected from the group consisting of gliomas, medulloblastomas, primitive neuroectodermal tumors (PNETS), basal cell carcinoma, small cell lung cancers, non-small cell lung cancers, tumors of the gastrointestinal tract, rhabdomyosarcomas, soft tissue sarcomas, pancreatic tumors and prostate tumors.

3. A method of inhibiting tumor cell growth or proliferation of a tumor cell in vitro, wherein said tumor cell expresses a GLI protein, said method comprising administering an siRNA molecule comprising SEQ ID NO: 29 to the tumor cell, wherein said administering results in induction of apoptosis in said tumor cell and an increased sensitivity to chemotherapeutic agents.

4. The method of claim 3, wherein siRNA molecule is SEQ ID NO:

* * * * *